(12) United States Patent
Rommens et al.

(10) Patent No.: US 8,158,414 B2
(45) Date of Patent: *Apr. 17, 2012

(54) GENE SILENCING

(75) Inventors: Caius Rommens, Boise, ID (US); Hua Yan, Boise, ID (US); Oleg Bougri, Boise, ID (US); Kathy M. M. Swords, Boise, ID (US)

(73) Assignee: J.R. Simplot Company, Boise, ID (US)

( * ) Notice: Subject to any disclaimer, the term of this patent is extended or adjusted under 35 U.S.C. 154(b) by 900 days.

This patent is subject to a terminal disclaimer.

(21) Appl. No.: 11/662,872

(22) PCT Filed: Sep. 23, 2005

(86) PCT No.: PCT/US2005/033992
§ 371 (c)(1),
(2), (4) Date: Oct. 15, 2007

(87) PCT Pub. No.: WO2006/036739
PCT Pub. Date: Apr. 6, 2006

(65) Prior Publication Data
US 2009/0100548 A1 Apr. 16, 2009

Related U.S. Application Data

(60) Provisional application No. 60/612,638, filed on Sep. 24, 2004, provisional application No. 60/619,959, filed on Oct. 20, 2004, provisional application No. 60/653,609, filed on Feb. 16, 2005, provisional application No. 60/668,071, filed on Apr. 5, 2005.

(51) Int. Cl.
*C12N 15/82* (2006.01)
*C12N 15/63* (2006.01)
*C07H 21/04* (2006.01)

(52) U.S. Cl. ............ 435/320.1; 536/24.5; 536/24.1

(58) Field of Classification Search .................. None
See application file for complete search history.

(56) References Cited

U.S. PATENT DOCUMENTS

| | | | |
|---|---|---|---|
| 5,107,065 A | 4/1992 | Shewmaker et al. | |
| 5,231,020 A | 7/1993 | Jorgensen et al. | |
| 5,283,184 A | 2/1994 | Jorgensen et al. | |
| 5,759,829 A | 6/1998 | Shewmaker et al. | |
| 5,998,701 A | 12/1999 | Kawchuk et al. | |
| 6,160,204 A | 12/2000 | Steffens | |
| 6,521,816 B1 | 2/2003 | Frohberg | |
| 7,005,423 B1 | 2/2006 | Plaetinck et al. | |
| 7,250,554 B2 | 7/2007 | Rommens et al. | |
| 7,534,934 B2 | 5/2009 | Rommens et al. | |
| 7,663,023 B2 | 2/2010 | Dixon et al. | |
| 7,713,735 B2 * | 5/2010 | Rommens et al. | ........ 435/320.1 |
| 2002/0019998 A1 | 2/2002 | Sonnewald | |
| 2002/0069430 A1 | 6/2002 | Kisaka et al. | |
| 2002/0182223 A1 | 12/2002 | LaCount | |
| 2003/0221213 A1 | 11/2003 | Rommens et al. | |
| 2004/0003434 A1 | 1/2004 | Weeks et al. | |
| 2004/0018541 A1 | 1/2004 | Allen et al. | |
| 2004/0107455 A1 | 6/2004 | Rommens et al. | |
| 2004/0132042 A1 * | 7/2004 | Frankard et al. | ................. 435/6 |
| 2004/0166580 A1 | 8/2004 | Plaetinck et al. | |
| 2005/0034188 A1 | 2/2005 | Weeks et al. | |
| 2006/0005280 A1 | 1/2006 | Stoop et al. | |
| 2006/0041957 A1 | 2/2006 | McGonigle et al. | |
| 2006/0156428 A1 | 7/2006 | Rommens et al. | |
| 2006/0233930 A1 | 10/2006 | Soyka et al. | |
| 2007/0074304 A1 | 3/2007 | Rommens | |
| 2007/0174932 A1 | 7/2007 | Uwer et al. | |
| 2009/0123626 A1 | 5/2009 | Rommens et al. | |

FOREIGN PATENT DOCUMENTS

| | | |
|---|---|---|
| WO | WO 97/40707 | 11/1997 |
| WO | WO 99/53050 A1 | 10/1999 |
| WO | WO 03/069980 A2 | 8/2003 |
| WO | WO 03/079765 A2 | 10/2003 |
| WO | WO 2004/009794 A | 1/2004 |
| WO | WO 2005/002994 A1 | 1/2005 |
| WO | WO 2005/004585 A2 | 1/2005 |
| WO | WO 2005/029944 A2 | 4/2005 |
| WO | WO 2005/121347 A | 12/2005 |
| WO | WO 2006/036739 A2 | 4/2006 |
| WO | WO 2007/035752 A2 | 3/2007 |

OTHER PUBLICATIONS

Thomas et al. 2001, The Plant Journal 25(4):417-425.*
Bieri et al., "Geminivirus sequences as bidirectional transcription termination/polyadenylation signals for economic construction of stably expressed transgenes", *Kluwer Academic Publishers*, (2002), pp. 107-117, vol. 10, The Netherlands.
Tran et al., Expressing Functional siRNAs in Mammalian Cells Using Convergent Transcription, *BMC Biotechnology*, Nov. 6, 2003, vol. 3, No. 21, pp. 1-9.
PCT International Search Report (mailing date: Sep. 24, 2008).
"Acrylamide in foods: a health risk to be taken seriously", (http://www.bgvv.de), Aug. 30, 2002, 3 pages, Abstract.
"Action value; a first step in the direction of drastic reduction of acrylamide in foods", (http://www.bgvv.de), Aug. 14, 2002, 2 pages, Abstract.
Amrein et al., "Potential of Acrylamide Formation, Sugars, and Free Asparagine in Potatoes: A Comparison of cultivars and Farming Systems", *J. Agric. Food Chem.*, (2003), pp. 5556-5560, vol. 51, The American Chemical Society.
"Baden-Württemberg food monitoring with new research results", www.mlr.baden-wuerttemberg.de/), Oct. 1, 2002, 2 pages, Abstract.
Becalski et al., "Acrylamide in French Fries: Influence of Free Amino Adds and Sugars", *J. Agric. Food Chem.*, (2004), pp. 3801-3806, vol. 52, American Chemical Society.

(Continued)

*Primary Examiner* — Li Zheng
(74) *Attorney, Agent, or Firm* — Foley & Lardner LLP

(57) ABSTRACT

The present invention relates to unique strategies and constructs for producing a nucleic acid product that down-regulates or prevents expression of a desired target polynucleotide. Such construct may include an expressing cassette having two convergently-oriented promoters each operably linked to a polynucleotide, but not to a terminator. The two polynucleotides are fully identical in sequence over at least 23 nucleotides.

16 Claims, 13 Drawing Sheets

OTHER PUBLICATIONS

Bevan, Michael, "Binary *Agrobacterium* vectors for plant transformation", *Nucleic Acids Research*, (1984), pp. 8711-8721, vol. 12, No. 22.

"BgVV—Expert discussion on the occurrence of acrylamide in foods", (http://www.bgvv.de), May 17, 2002, 1 page, Abstract.

Biedermann et al., "Experiments on Acrylamide Formation and Possibilities to Decrease the Potential of Acrylamide Formation in Potatoes", *Mitt. Lebensm. Hyg.*, Jun. 2002, pp. 668-687, vol. 93, BAG OFSP UFSP SFOPH.

Blank et al., "Mechanism of Acrylamide Formation", *Chemistry and Safety of Acrylamid in Food*, (2005), pp. 171-189, Springer Science+Business Media, Inc.

"FDA plans to identify and reduce acrylamides in food", *OncoLink—Reuters Health*. Sep. 30, 2002, 2 pages, http://www.oncolink.com/custom_tags/pring_article.cfm?Page=2&id=8896&Section=Reu....

Foot et al., "Acrylamide in fried and roasted potato products: A review on progress in mitigation", *Food Additives and Contaminants., Supplement 1*, (2007), pp. 37-46, vol. 24, No. S1, Taylor & Francis.

Friedman et al., "Review of Methods for the Reduction of Dietary Content and toxicity of Acrylamide", *J. Agric. Food Chem.*, (2008), pp. 6113-6140, vol. 56, American Chemical Society.

Friedman, M., "Chemistry, Biochemistry, and Safety of Acrylamide. A Review", *J. Agric. Food Chem.*, (2003), pp. 4504-4526, vol. 51, The American Chemical Society.

Genbank accession V00090, Apr. 18, 2005.

Halford et al., "Genetic and agronomic approaches to decreasing acrylamide precursors in crop plants", *Food Additives and Contaminants., Supplement 1*, (2007), pp. 26-36, vol. 24, No. S1 , Taylor & Francis.

Hanley et al., "Acryiamide Reduction in Processed Foods", *Chemistry and Safety of Acrylamid in Food*, (2005), pp. 387-392, Springer Science+Business Media, Inc.

Heilersig et al., "Efficiency of transcriptional gene silencing of GBSSI in potato depends on the promoter region that is used in an inverted repeat", *Mol. Gen. Genomics*, (2006), pp. 437-449, vol. 275, Springer-Verlag.

Ishihara et al., "Formation of Acrylamide in a Processed Food Model System, and Examination of Inhibitory Conditions", *J. Food Hyg, Soc. Japan*, Apr. 2005, pp, 33-39, vol. 46, No. 2, Shokuhin Eiseigaku Zasshi.

Knol et al., "Toward a Kinetic Model for Acrylamide Formation in a Glucose—Asparagine Reaction System", *J. Agric. Food Chem.*, (2005), pp. 6133-6139, vol. 53, American Chemical Society.

Lam et al., "Metabolic Regulation of the Gene Encoding Glutamine-Dependent Asparagine Synthetase in *Arabidopsis thaliana*", *Plant Physiol.*, (1994), pp. 1347-1357, vol. 106.

Lorberth et al., "Inhibition of a starch-granule-bound protein leads to modified starch and repression of cold sweetening", *Nature Biotechnology*, May 1998, pp. 1-6, vol. 16.

Matthäus et al., "Factors affecting the concentration of acrylamide during deep-fat frying of potatoes", *European Journal of Lipid Science and Technology*, Nov. 18, 2004, 1 page, vol. 106, issue 11, Wiley-VCH Verlag GmbH & Co.

Mestdagh et al., "Role of Water Upon the Formation of Acrylamide in a Potato Model System", *J. Agric. Food Chem.*, (2006), pp. 9092-9098, vol. 54, American Chemical Society.

Mottram et al., "Acrylamide is formed in the Maillard reaction", *Nature*, Oct. 3, 2002, 1 page, vol. 419, Nature Publishing Group.

Muttucumaru et al., "Reducing Acrylamide Precursors in Raw Materials Derived from Wheat and Potato", *J. Agric. Food Chem.*, (2008), pp. 6167-6172, vol. 56, American Chemical Society.

Nair et al., "Evidence for *de novo* Synthesis of Asparagine Synthetase in Gamma Irradiated Potatoes", *Indian Journal of Biochemistry & Biophysics*, Dec. 1971, pp. 204-209, vol. 8, The Council of Scientific & Industrial Research, New Delhi.

Palazoglu et al., "Reduction of Acrylamide Level in French Fries by Employing a Temperature Program during Frying", *J. Agric. Food Chem.*, (2008), pp. 6162-6166, vol. 56, American Chemical Society.

Palevitz, B. A., "Acrylamide in French Fries", *Scientist*, Oct. 14, 2002, 2 pages, vol. 16, No. 20.

Park et al., "Controlling Acrylamide in French Fry and Potato Chip Models and a Mathematical Model of Acrylamide Formation", *Chemistry and Safety of Acrylamid in Food*, (2005), pp. 343-356, Springer Science+Business Media, Inc.

Pollien, et al., "Proton Transfer Reaction Mass Spectrometry, a Tool for On-Line Monitoring of Acrylamide Formation in the Headspace of Maillard Reaction Systems and Processed Food", *Analytical Chemistry*, Oct. 15, 2003, pp. 5488-5494, vol. 75, No. 20, American Chemical Society.

Presse—Archive 2002 (original German language abstracts available online at www.archive.org. English translations are submitted herein under "Baden-Württemberg food monitoring with new research results", "Acrylamide in foods: a health risk to be taken seriously", "Action value: a first step in the direction of drastic reduction of acrylamide in foods", "SCF publishes scientific evaluation of acrylamide in foods", "BgVV—Expert discussion on the occurrence of acrylamide in foods", and "Sweden detects acrylamide in foods", 17 pages. Abstracts.

Raloff, J., "Hot Spuds—Golden Path to acrylamide in food", *Science News This Week*, Oct. 5, 2002, 3 pages, www.sciencenews.org.

Robert et al., "Acrylamide Formation from Asparagine under Low-Moisture Maillard Reaction Conditions. 1. Physical and Chemical Aspects in Crystalline Model Systems", *J. Agric. Food Chem.*, (2004), pp. 6837-6842, vol. 52, American Chemical Society.

Rommens et al., "Low-acrylamide French fries and potato chips", *Plant Biotechnology Journal*, (2008), pp. 843-853, vol. 6, Blackwell Publishing Ltd.

Rosén et al., "Analysis of acrylamide in cooked foods by liquid chromatography tandem mass spectrometry", *Analyst*, (2002), pp. 880-882, vol. 127, The Royal Society of Chemistry 2002.

Rosen. J.D., "Acrylamide in Food: Is It a Real Threat to Public Health?", *American Council on Science and Health*, Dec. 2002, 17 pages.

"SCF publishes scientific evaluation of acrylamide in foods", (http://www.europa.eu.int), Jul. 8, 2002, 1 page, Abstract.

"Scientists Look for clues to Perils Lurking in Foods", *The New York Times*, Oct. 1, 2002, 2 pages, http://www.nytimes.com/2002/10/01/science/scientists-look-for-clues-to-perils-lerking-in....

Serpen et al., "Modeling of acrylamide formation and browning ration in potato chips by artificial neural network", *Mol. Nutr. Food Res.*, (2007), pp. 383-389, vol. 51, Wiley-VCH Verlag GmbH &Co. KGaA, Weinheim.

Sharp, D., "Acrylamide in Food", *The Lancet*, Feb. 1, 2003, pp. 361-362, vol. 361, No. 9355, Elsevier Ltd.

Silva et al., "Genetic, Physiological, and Environmental Factors Affecting Acrylamide Concentration in Fried Potato Products", *Chemistry and Safety of Acrylamid in Food*, (2005), pp. 371-386, Springer Science+Business Media, Inc.

Stadler et al., "Acrylamide from Maillard reaction products", *Nature*, Oct. 3, 2002, 2 pages, vol. 419, Nature Publishing Group.

Stadler et al., "in-Depth Mechanistic Study on the Formation of Acrylamide and Other Vinylogous Compounds by the Maillard Reaction", *J. Agric. Food Chem.*, (2004), pp. 5550-5558, vol. 52, American Chemical Society.

Stadler, R. H., "Acrylamide Formation in Different Foods and Potential Strategies for Reduction", *Chemistry and Safety of Acryiamid in Food*, (2005), pp. 157-169, Springer Science+Business Media, Inc.

Starck, P., "Update 3-Crisps, french fries, bread may cause cancer-study" , *Reuters*, Apr. 24, 2002, 8 pages, http://curezone.com/art/read.asp?ID=42&db=6&C0=17.

"Sweden detects acrylamide in foods", (http://www.bgvv.de), Apr. 25, 2002, 1 page, Abstract.

Taeymans et al., "A Review of Acrylamide: An industry Perspective on Research, Analysis, Formation, and Control", *Critical Reviews in Food Science and Nutrition*, (2004), pp. 323-347, vol. 44, Taylor & Francis, Inc.

Takada et al., "Change in Content of Sugars and Free Amino Acids in Potato Tubers under Short-Term Storage at Low Temperature and the Effect on Acrylamide Level After Frying", *Biosci. Biotechnol. Biochem.*, (2005), pp. 1232-1238, vol. 69, No. 7, Japan Society for Bioscience Biotechnology and Agrochemistry.

Taubert et al., "Influence of Processing Parameters on Acrylamide Formation during frying of Potatoes", *J. Agric. Food Chem.*, (2004), pp. 2735-2739, vol. 52, American Chemical Society.

Van Montagu et al., "The Interaction of *Agrobacterium* Ti-Plasmid DNA and Plant Cells", *Proc R Soc Lond B Biol Sci*, Nov. 19, 1980, pp. 351-365, vol. 210, No. 1180, Great Britain.

Weisshaar et al., "Formation of Acrylamide in Heated Potato Products—Model Experiments Pointing to Asparagine as Precursor", *Deutsch Lebensmittel-Rundschau*. Oct. 3. 2002, pp. 397-400, vol. 98, No. 11, Behr's Verlag, Hamburg, Germany.

Williams, J. S. E., "Influence of variety and processing conditions on acrylamide levels in fried potato crisps", *Food Chemistry*, (2005), pp. 875-881, vol. 90, Elsevier Ltd.

Yarnell, A., "Acrylamide Mystery Solved—Heating asparagine with sugar yields chemical found in cooked foods", *Chemical & Engineering News*, Oct. 7, 2002, 2 pages, vol. 80, No. 40, http://pubs.acs.org/cen.

Yaylayan et al., "Why asparagine needs carbohydrates to generate acrylamide", *J. Agric. Food Chem.*, Mar. 12, 2003, vol. 51, No. 6, 2 pages, http://www.ncbi.nlm.nih.gov/pubmed/12617619.

Yoshida et al., "Acrylamide in Japanese Processed Foods and Factors Affecting Acrylamide Level in Potato Chips and Tea", *Chemistry and Safety of Acrylamid in Food*, (2005), pp. 405-413, Springer Science+Business Media, Inc.

Zhang et al., "Occurrence and analytical methods of acrylamide in heat-treated foods Review and recent developments", *Journal of Chromatography A*, (2005), pp. 1-21, vol. 1075, Elsevier B. V.

Kanno et al., "Scientific Report—A SNF2-Like Protein Facilitates Dynamic Control of DNA Methylation", *EMBO Reports*, 2005, pp. 649-655, vol. 6, No. 7, European Molecular Biology Organization.

Kanno et al., "Involvement of Putative SNF2 Chromatin Remodeling Protein DRD1 in RNA-Directed DNA Methylation", *Current Biology*, May 4, 2004, pp. 801-805, vol. 14, Elsevier Ltd.

Shi et al., "Genetic Interference in *Trypanosoma brucei* by beritable and inducible double-stranded RNA", *RNA Society*, (2000), pp. 1069-1076, Cambridge University Press, USA.

Casas-Flores, et al., "Three Decades of Fungal Transformation: Novel Technologies," *Methods Mol. Biol.*, 2004, vol. 267, pp. 315-325.

De Buck et al., "Transgene Silencing of Invertedly Repeated Transgenes is Released Upon Deletion of One of The Transgenes Involved", *Plant Molecular Biology*, 2001, vol. 46:, pp. 433-445.

Dodo et al., "A Genetic Engineering Strategy to Eliminate Peanut Allergy", *Current Science Inc.*, 2005, vol. 5, pp. 67-73.

Genbank Accession M21375, 2000.

Genbank Accession Z11669, 2005.

Genbank Accession CQ889094, 2004.

Gillissen et al., "Silencing the Major Apple Allergen Mal d 1 by Using the RNA Interference Approach," *J Allergy Clin Immunol*, Feb. 2005, vol. 115, No. 2, pp. 364-369.

Herman et al., "Genetic Modification Removes an Immunodominant Allergen From Soybean," *Plant Physiology*, May 2003, vol. 132, pp. 36-43.

Kunik, et al., "Genetic Transformation of HeLa Cells by Agrobacterium," *Proc. Natl. Acad. Sci.*, 2001, pp. 1871-1876, vol. 98, No. 4, USA.

Liu et al., "High Stearic and High Oleic Cottonseed Oils Produced by Hairpin RNA-Mediated Post-Transcriptional Gene Silencing," *Plant Physiology*, Aug. 2002, vol. 129, pp. 1732-1743.

Meister et al., "Mechanisms of Gene Silencing by Double-Stranded RNA", *Nature*, 2004, vol. 431, pp. 343-349.

Mette et al., "Production of aberrant Promoter Transcripts Contributes to Methylation and Silencing of Unlinked Homologous Promoters *in trans*", *The EMBO Journal*, 1999, pp. 241-248, vol. 18, No. 1.

Mette et al., "Transcriptional Silencing and Promoter Methylation Triggered by Double-Stranded RNA", *The EMBO Journal*, 2000, pp. 5194-5201, vol. 19, No. 19.

Smith et al., "Gene Expression: Total Silencing by Intron-Spliced Hairpin RNAs", *Nature*, Sep. 21, 2000, vol. 407, pp. 319-320.

Thomas et al., "Size Contraints for Targeting Post-Transcriptional Gene Silencing and for RNA-Directed Methylation in Nicotiana Benthamiana Using a Potato Virus X Vector", *The Plant Journal*, 2001, vol. 25 No. 4, pp. 417-425.

USDA, ARS, National Genetic Resources Program, *Germplasm Resources Information Network—(GRIN)*. [Online Database] National Germplasm Resources Laboratory, Beltsville, Maryland. Available: http://www.ars-grin.gov/cgi-bin/npgs/acc/display.pl?1392998 (Aug. 15, 2007).

Kawai et al., Isolation and Analysis of cinnamic Acid 4-hydroxylase Homologous Genes from Hybrid Aspen, Populus Kitakamiensis, Biosci, Biotechnol. Biochem, (1996), 60(10), pp. 1586-1597.

Sijen et al., "Transcriptional and Posttranscriptional Gene Silencing are Mechanistically Related", Brief Communication—Curr. Biol., (2001), pp. 436-440, vol. 11, No. 6, Elsevier Science Ltd.

Sijen et al.. "Supplemental Material", Curr. Biol., (2001), pp. S1-S2, vol. 11, Elsevier Science Ltd.

\* cited by examiner

Figure 9

Part of P1 promoter that facilitates gene silencing
CAAGTGGGGAACAAAATAACGTGGAAAAGAGCTGTCCTGACAGCCCACTCACTAATGCGTATGACGAACGCAGTGAC
GACCACAAAAGA (SEQ ID NO: 60)

774

775

787

1111

1120

789

SEQUENCE LISTING

<160> NUMBER OF SEQ ID NOS: 60

<210> SEQ ID NO 1
<211> LENGTH: 581
<212> TYPE: DNA
<213> ORGANISM: Figwort mosaic virus

<400> SEQUENCE: 1

```
atttagcagc attccagatt gggttcaatc aacaaggtac gagccatatc actttattca      60
aattggtatc gccaaaacca agaaggaact cccatcctca aaggtttgta aggaagaatt     120
ctcagtccaa agcctcaaca aggtcagggt acagagtctc caaaccatta gccaaaagct     180
acaggagatc aatgaagaat cttcaatcaa agtaaactac tgttccagca catgcatcat     240
ggtcagtaag tttcagaaaa agacatccac cgaagactta agttagtgg gcatctttga      300 aagtaatctt gtcaacatcg agcagctggc ttgtggggac cagacaaaaa aggaatggtg     360
cagaattgtt aggcgcacct accaaaagca tctttgcctt tattgcaaag ataaagcaga     420
```

```
ttcctctagt acaagtgggg aacaaaataa cgtggaaaag agctgtcctg acagcccact    480
cactaatgcg tatgacgaac gcagtgacga ccacaaaaga attccctcta tataagaagg    540
cattcattcc catttgaagg atcatcagat actcaaccaa t                        581
```

<210> SEQ ID NO 2
<211> LENGTH: 304
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2

```
caacgcgtaa actcgacccg acgcgtccga tcacctgcgt caatgtaatg ttctgcgacg    60
ctcacaccga taccatcagc gatctctttg atgtgctgtg cctgaaccgt tattacggat   120
ggtatgtcca aagcggcgat ttggaaacgg cagagaaggt actggaaaaa gaacttctgg   180
cctggcagga gaaactgcat cagccgatta tcatcaccga atacggcgtg gatacgttag   240
ccgggctgca ctcaatgtac accgacatgt ggagtgaaga gtatcagtgt gcatggctgg   300
atat                                                                304
```

<210> SEQ ID NO 3
<211> LENGTH: 253
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3

```
cgttcaaaca tttggcaata aagtttctta agattgaatc ctgttgccgg tcttgcgatg    60
attatcatat aatttctgtt gaattacgtt aagcatgtaa taattaacat gtaatgcatg   120
acgttattta tgagatgggt ttttatgatt agagtcccgc aattatacat ttaatacgcg   180
atagaaaaca aaatatagcg cgcaaactag gataaattat cgcgcgcggt gtcatctatg   240
ttactagatc ggg                                                      253
```

<210> SEQ ID NO 4
<211> LENGTH: 244
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 4

```
gtggtaactt ttactcatct cctccaatta tttctgattt catgcatgtt tccctacatt    60
ctattatgaa tcgtgttatg gtgtataaac gttgtttcat atctcatctc atctattctg   120
attttgattc tcttgcctac tgaatttgac cctactgtaa tcggtgataa atgtgaatgc   180
ttcctcttct tcttcttctt ctcagaaatc aatttctgtt ttgttttgt tcatctgtag   240 cttg                                                                244
```

<210> SEQ ID NO 5
<211> LENGTH: 545
<212> TYPE: DNA
<213> ORGANISM: Cauliflower mosaic virus

<400> SEQUENCE: 5

```
tagcttcatg gagtcaaaga ttcaaataga ggacctaaca gaactcgccg taaagactgg    60
```

-continued

```
cgaacagttc atacagagtc tcttacgact caatgacaag aagaaaatct tcgtcaacat      120
ggtggagcac gacacacttg tctactccaa aaatatcaaa gatacagtct cagaagacca      180
aagggcaatt gagactttc aacaaagggt aatatccgga aacctcctcg gattccattg       240
cccagctatc tgtcacttta ttgtgaagat agtggaaaag gaaggtggct cctacaaatg      300
ccatcattgc gataaaggaa aggccatcgt tgaagatgcc tctgccgaca gtggtcccaa      360
agatggaccc ccacccacga ggagcatcgt ggaaaaagaa gacgttccaa ccacgtcttc      420
aaagcaagtg gattgatgtg atatctccac tgacgtaagg gatgacgcac aatcccacta      480
tccttcgcaa gacccttcct ctatataagg aagttcattt catttggaga gaacacgggg      540
gactc                                                                  545

<210> SEQ ID NO 6
<211> LENGTH: 1024
<212> TYPE: DNA
<213> ORGANISM: Solanum tuberosum

<400> SEQUENCE: 6
tcgagcacat tgattgagtt ttatatgcaa tatagtaata ataataatat ttcttataaa       60
gcaagaggtc aattttttt tattatacca acgtcactaa attatatttg ataatgtaaa      120
acaattcaat tttacttaaa tatcatgaaa taaactattt ttataaccaa attactaaat      180
ttttccaata aaaaaagtc attaagaaga cataaaataa atttgagtaa aaagagtgaa      240
gtcgactgac ttttttttt ttatcataag aaaataaatt attaacttta acctaataaa      300
acactaatat aatttcatgg aatctaatac ttacctctta gaaataagaa aaagtgtttc      360
taatagaccc tcaatttaca ttaaatattt tcaatcaaat ttaaataaca aatatcaata      420
tgaggtcaat aacaatatca aaataatatg aaaaaagagc aatacataat ataagaaaga      480
agatttaagt gcgattatca aggtagtatt atatcctaat ttgctaatat ttaaactctt      540
atatttaagg tcatgttcat gataaacttg aaatgcgcta tattagagca tatattaaaa      600
taaaaaaata cctaaaataa aattaagtta ttttagtat atattttttt acatgaccta      660 cattttctg ggttttcta aaggagcgtg taagtgtcga cctcattctc ctaattttcc       720
ccaccacata aaaattaaaa aggaaaggta gcttttgcgt gttgttttgg tacactacac      780
ctcattatta cacgtgtcct catataattg gttaaccta tgaggcggtt tcgtctagag      840
tcggccatgc catctataaa atgaagcttt ctgcacctca tttttttcat cttctatctg      900
atttctatta taatttctct caattgcctt caaatttctc tttaaggtta gaaatcttct      960
ctattttggg tttttgtctg tttagattct cgaattagct aatcaggtgc tgttatagcc     1020
ctta                                                                  1024

<210> SEQ ID NO 7
<211> LENGTH: 175
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
ccttcacccg gttgccagag gtgcggattc accacttgca aagtcccgct agtgccttgt       60
ccagttgcaa ccacctgttg atccgcatca cgcagttcaa cgctgacatc accattggcc      120
accacctgcc agtcaacaga cgcgtggtta cagtcttgcg cgacatgcgt cacca           175
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caacgcgtaa actcgacccg acgcgtc                                        27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttgtttttgt tcatctgtag cttctgc                                        27

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggaggagat gagtaaaagt taccacg                                        27

<210> SEQ ID NO 11
<211> LENGTH: 300
<212> TYPE: DNA
<213> ORGANISM: Figwort mosaic virus

<400> SEQUENCE: 11
atttagcagc attccagatt gggttcaatc aacaaggtac gagccatatc actttattca    60
aattggtatc gccaaaacca agaaggaact cccatcctca aaggtttgta aggaagaatt    120
ctcagtccaa agcctcaaca aggtcagggt acagagtctc caaaccatta gccaaaagct    180
acaggagatc aatgaagaat cttcaatcaa agtaaactac tgttccagca catgcatcat    240
ggtcagtaag tttcagaaaa agacatccac cgaagactta agttagtgg catctttga    300

<210> SEQ ID NO 12
<211> LENGTH: 658
<212> TYPE: DNA
<213> ORGANISM: Solanum tuberosum

<400> SEQUENCE: 12
gaaccatgca tctcaatctt aatactaaaa aatgcaacaa aattctagtg gagggaccag    60
taccagtaca ttagatatta tcttttatta ctataataat attttaatta acacgagaca    120
taggaatgtc aagtggtagc ggtaggaggg agttggttca gttttttaga tactaggaga    180
cagaaccgga ggggcccatt gcaaggccca agttgaagtc cagccgtgaa tcaacaaaga    240
gagggcccat aatactgtcg atgagcattt ccctataata cagtgtccac agttgccttc    300
cgctaaggga tagccacccg ctattctctt gacacgtgtc actgaaacct gctacaaata    360
aggcaggcac ctcctcattc tcacactcac tcactcacac agctcaacaa gtggtaactt    420
ttactcatct cctccaatta tttctgattt catgcatgtt tccctacatt ctattatgaa    480

```
tcgtgttatg gtgtataaac gttgtttcat atctcatctc atctattctg attttgattc    540
tcttgcctac tgaatttgac cctactgtaa tcggtgataa atgtgaatgc ttcctcttct    600
tcttcttctt ctcagaaatc aatttctgtt ttgttttttgt tcatctgtag cttggtag    658
```

<210> SEQ ID NO 13
<211> LENGTH: 1024
<212> TYPE: DNA
<213> ORGANISM: Solanum tuberosum

<400> SEQUENCE: 13

```
ccgcagtgtg ccagggctgt cggcagatgg acataaatgg cacaccgctc ggctcgtgga     60
aagagtatgg tcagtttcat tgataagtat ttactcgtat tcggtgttta catcaagtta    120
atatgttcaa acacatgtga tatcatacat ccattagtta agtataaatg ccaacttttt    180
acttgaatcg ccgaataaat ttacttacgt ccaatattta gttttgtgtg tcaaacatat    240
catgcactat ttgattaaga ataaataaac gatgtgtaat ttgaaaacca attagaaaag    300
aagtatgacg ggattgatgt tctgtgaaat cactggtaaa ttggacggac gatgaaattt    360
gatcgtccat ttaagcatag caacatgggt ctttagtcat catcattatg ttataattat    420
tttcttgaaa cttgatacac caactttcat tgggaaagtg acagcatagt ataaactata    480
atatcaattc tggcaatttc gaattattcc aaatctcttt tgtcatttca tttcctcccc    540
tatgtctgca agtaccaatt atttaagtac aaaaaatctt gattaaacaa tttatttttct   600 cactaataat cacatttaat catcaacggt tcatacacgt ctgtcactct ttttttattc    660
tctcaagcgc atgtgatcat accaattatt taaatacaaa aatcttgat taaacaattc     720 agttctcac taataatcac atttaatcat caacggttca tacacatccg tcactctttt      780
tttattctct caagcgcatg tgatcatacc aattatttaa atacaaaaaa tcttgattaa    840
acaattcatt ttctcactaa taatcacatt taatcatcaa cggtttatac acgtccgcca    900 ctctttttt attctctcaa gcgtatgtga tcatatctaa ctctcgtgca aacaagtgaa      960
atgacgttca ctaataaata atcttttgaa tactttgttc agtttaattt atttaatttg   1020
ataa                                                                1024
```

<210> SEQ ID NO 14
<211> LENGTH: 154
<212> TYPE: DNA
<213> ORGANISM: Solanum tuberosum

<400> SEQUENCE: 14

```
ttagtctcta ttgaatctgc tgagattaca ctttgatgga tgatgctctg ttttttgtttt     60 cttgttctgt ttttttcctct gttgaaatca gctttgttgc ttgatttcat tgaagttgtt    120
attcaagaat aaatcagtta caattatgtt tggg                                 154
```

<210> SEQ ID NO 15
<211> LENGTH: 569
<212> TYPE: DNA
<213> ORGANISM: Solanum tuberosum

<400> SEQUENCE: 15

```
gttagaaatc ttctctatt ttggttttttg tctgtttaga ttctcgaatt agctaatcag      60
gtgctgttat agcccttaat tttgagtttt ttttcggttg ttttgatgga aaaggcctaa     120
aatttgagtt ttttttacgtt ggtttgatgg aaaaggccta caattggagt tttccccgtt    180
gttttgatga aaaagcccct agtttgagat ttttttttctg tcgattcgat tctaaaggtt    240
```

```
taaaattaga gttttttacat ttgtttgatg aaaaaggcct taaatttgag tttttccggt    300
tgatttgatg aaaaagccct agaatttgtg ttttttcgtc ggtttgattc tgaaggccta    360
aaatttgagt ttctccggct gttttgatga aaaagcccta aatttgagtt tctccggctg    420
ttttgatgaa aaagccctaa atttgagttt ttccccgtg ttttagattg tttggtttta    480
attctcgaat cagctaatca gggagtgtga aaagccctaa aatttgagtt ttttcgttg    540 ttctgattgt tgttttatg aatttgcag                                      569

<210> SEQ ID NO 16
<211> LENGTH: 154
<212> TYPE: DNA
<213> ORGANISM: Nicotiana tabacum

<400> SEQUENCE: 16
ttagtctcta ttgaatctgc tgagattaca ctttgatgga tgatgctctg ttttttgtttt    60 cttgttctgt ttttcctct gttgaaatca gctttgttgc ttgatttcat tgaagttgtt   120
attcaagaat aaatcagtta caattatgtt tggg                                154

<210> SEQ ID NO 17
<211> LENGTH: 3272
<212> TYPE: DNA
<213> ORGANISM: Solanum tuberosum

<400> SEQUENCE: 17
tggcaggata tataccggtg taaacgaagt gtgtgtggtt gatccaaaat ctatcgtacc     60
tttagaaagt gtagctatga aggatagtct cacttatgaa gaactaccta ttgagattct    120
tgatcgtcag gtccgaaggt tgagaaaaat agaagtcgct tcagttacgg ctttgtggag    180
gagtaagggt accgaaccat gcatctcaat cttaatacta aaaaatgcaa caaaattcta    240
gtggagggac cagtaccagt acattagata ttatcttttta ttactataat aatattttaa    300
ttaacacgag acataggaat gtcaagtggt agcggtagga gggagttggt tcagtttttt    360
agatactagg agacagaacc ggaggggccc attgcaaggc ccaagttgaa gtccagccgt    420
gaatcaacaa agagagggcc cataatactg tcgatgagca tttcccctata atacagtgtc    480 cacagttgcc ttccgctaag ggatagccac ccgctattct cttgacacgt gtcactgaaa    540
cctgctacaa ataaggcagg cacctcctca ttctcacact cactcactca cacagctcaa    600
caagtggtaa cttttactca tctcctccaa ttatttctga tttcatgcat gttttccctac    660 attctattat gaatcgtgtt atggtgtata acgttgtttt catatctcat ctcatctatt    720
ctgattttga ttctccttgcc tactgaattt gaccctactg taatcggtga taaatgtgaa    780
tgcttcctct tcttcttctt cttctcagaa atcaatttct gttttgtttt tgttcatctg    840
tagcttggta gattcccctt tttgtagacc acacatcacg gatccccaa acataattgt    900 aactgattta ttcttgaata caacttcaa tgaaatcaag caacaaagct gatttcaaca    960
tgaaaaaaca gaacaagaaa acgaaaacag agcatcatcc atcaaagtgt aatctcagca   1020
gattcaatag agactaactc gaggtgctct ctatgcaaat ctagcttttc gaatgagagt   1080
gataagagag tgaggattgt gaattatttt attgatgaag attggagaag tcaattattg   1140
attcacacac aggaattaag tgtgttgtgt tgcgtcctct tgtggaaatt aaatgtcacc   1200
ctttttttat ttatcaataa aagcacgaaa atctcctgca ctactcccct gcactctctt   1260
atatttgtcc atttcccaca aatccctaac ttaattactt acccacactc aagcttcaac   1320
actgttgagg ttaggaatcc ctggtacagc aagttattcc ctaaggaatt actcatatcc   1380
```

```
tcccactggc ttaattcact caagttcagc tagaaacgtc gatttctagt gaagtaacga    1440
ggaaattagc gaagaagcgt cgagaaattc gatgaagatg aattcacgaa gcaaaatgaa    1500
gattggagca gagagtatgg ggattggaga gtggaaagtg gtagtgaaat aaggtccgcg    1560
ggttaaattc atgattttat gaactcaata gcttttcata atgagcaata ttatctttct    1620
tcagtagcaa atccacatgc tcttatgctc gctgaaatag ttttggccgt ggagtttcac    1680
catctatgtt tacaattgat tcttgtagct gcagaccttc tttcactacc actttccact    1740
ctccaatccc catactctct gctccaatct tcattttgct tcgtgaattc atcttcatcg    1800
aatttctcga cgcttcttcg ctaatttcct cgttacttca ctagaaatcg acgtttctag    1860
ctgaacttga gtgaattaag ccagtgggag gatatgagta attccttagg gaataacttg    1920
ctgtaccagg gattcctaac ctcaacagtg ttgaagcttg agtgtgggta agtaattaag    1980
ttagggattt gtgggaaatg gacaaatata agagagtgca ggggagtagt gcaggagatt    2040
ttcgtgcttt tattgataaa taaaaaaagg gtgcatttta atttccacaa gaggacgcaa    2100
cacaacacac ttaattcctg tgtgtgaatc aataattgac ttctccaatc ttcatcaata    2160
aaataattca caatcctcac tctcttatca ctctcattcg aaaagctaga tttgcataga    2220
gagcacctcg agttagtctc tattgaatct gctgagatta cactttgatg gatgatgctc    2280
tgttttcgtt ttcttgttct gtttttttcat gttgaaatca gctttgttgc ttgatttcat    2340
tgaagttgtt attcaagaat aaatcagtta caattatgtt tgggtctaga gtgatgtgtg    2400
gtctacaaaa agggaatct accaagctac agatgaacaa aaacaaaaca gaaattgatt    2460
tctgagaaga agaagaagaa gaggaagcat tcacatttat caccgattac agtagggtca    2520
aattcagtag gcaagagaat caaaatcaga atagatgaga tgagatatga acaacgttt    2580
atacaccata acacgattca taatagaatg tagggaaaca tgcatgaaat cagaaataat    2640
tggaggagat gagtaaaagt taccacttgt tgagctgtgt gagtgagtga gtgtgagaat    2700
gaggaggtgc ctgccttatt tgtagcaggt ttcagtgaca cgtgtcaaga gaatagcggg    2760
tggctatccc ttagcggaag gcaactgtgg acactgtatt atagggaaat gctcatcgac    2820
agtattatgg gccctctctt tgttgattca cggctggact tcaacttggg ccttgcaatg    2880
ggccctccg gttctgtctc ctagtatcta aaaaactgaa ccaactccct cctaccgcta    2940
ccacttgaca ttcctatgtc tcgtgttaat taaaatatta ttatagtaat aaaagataat    3000
atctaatgta ctggtactgg tccctccact agaattttgt tgcattttt agtattaaga    3060
ttgagatgca tggttcgagc tccttcaaca tgttataaac ttcacatatt cagttgggaa    3120
taggctttat aatgagttgg actacgttat gtccccctca agtcccagaa ttatgtgccc    3180
ccgtatgtta taagtcccct ctgcgggcat caatttagtg atcacgccag acatgcctct    3240
atacctcggc caggatatat ttgttggtaa tg                                 3272
```

<210> SEQ ID NO 18
<211> LENGTH: 152
<212> TYPE: DNA
<213> ORGANISM: Solanum verrucosum

<400> SEQUENCE: 18

```
cccaaacata attgtaactg atttattctt gaataacaac ttcaatgaaa tcaagcaaca     60
aagctgattt caacatgaaa aaacagaaca agaaacgaa aacagagcat catccatcaa    120
agtgtaatct cagcagattc aatagagact aa                                  152
```

<210> SEQ ID NO 19
<211> LENGTH: 267
<212> TYPE: DNA
<213> ORGANISM: Solanum tuberosum

<400> SEQUENCE: 19

| | | |
|---|---|---|
| gtgctctcta tgcaaatcta gcttttcgaa tgagagtgat aagagagtga ggattgtgaa | 60 |
| ttattttatt gatgaagatt ggagaagtca attattgatt cacacacagg aattaagtgt | 120 |
| gttgtgttgc gtcctcttgt ggaaattaaa tgtcaccctt tttttattta tcaataaaag | 180 |
| cacgaaaatc tcctgcacta ctcccctgca ctctcttata tttgtccatt tcccacaaat | 240 |
| ccctaactta attacttacc cacactc | 267 |

<210> SEQ ID NO 20
<211> LENGTH: 239
<212> TYPE: DNA
<213> ORGANISM: Solanum tuberosum

<400> SEQUENCE: 20

| | |
|---|---|
| caacactgtt gaggttagga atccctggta cagcaagtta ttccctaagg aattactcat | 60 |
| atcctcccac tggcttaatt cactcaagtt cagctagaaa cgtcgatttc tagtgaagta | 120 |
| acgaggaaat tagcgaagaa gcgtcgagaa attcgatgaa gatgaattca cgaagcaaaa | 180 |
| tgaagattgg agcagagagt atggggattg gagagtggaa agtggtagtg aaataaggt | 239 |

<210> SEQ ID NO 21
<211> LENGTH: 520
<212> TYPE: DNA
<213> ORGANISM: Artificial Sequence
<220> FEATURE:
<223> OTHER INFORMATION: Description of Artificial Sequence: Synthetic construct

<400> SEQUENCE: 21

| | |
|---|---|
| atttagcagc attccagatt gggttcaatc aacaaggtac gagccatatc actttattca | 60 |
| aattggtatc gccaaaacca agaaggaact cccatcctca aaggtttgta aggaagaatt | 120 |
| ctcagtccaa agcctcaaca aggtcagggt acagagtctc caaaccatta gccaaaagct | 180 |
| acaggagatc aatgaagaat cttcaatcaa agtaaactac tgttccagca catgcatcat | 240 |
| ggtcagtaag tttcagaaaa agacatccac cgaagactta agttagtgg gcatctttga | 300 |
| aagtaatctt gtcaacatcg agcagctggc ttgtggggac cagacaaaaa aggaatggtg | 360 |
| cagaattgtt aggcgcacct accaaaagca tctttgcctt tattgcaaag ataaagcaga | 420 |
| ttcctctagt acaagtgggg aacaaaataa cgtggaaaag agctgtcctg acagcccact | 480 |
| cactaatgcg tatgacgaac gcagtgacga ccacaaaaga | 520 |

<210> SEQ ID NO 22
<211> LENGTH: 1024
<212> TYPE: DNA
<213> ORGANISM: Solanum tuberosum

<400> SEQUENCE: 22

| | |
|---|---|
| ttcaaatttc atttgtgtca tataaattga gacatataat tgtcggcaca tgctcatgta | 60 |
| tccaaacaag gataatttga tcatctattc ttatatattt gaaaattacg ataataatac | 120 |
| tttaaatcac aataattaac aagttaaaat atttaaaagt catataaaaa attaattgac | 180 |
| tctcaaaatt ctgtaagtac tataaattaa aataaataac aacttaagaa tttcaaagtc | 240 |
| ataaaaaatt tggtggctct ctaaaatata tcaatgtcac ataaaaagta acatatatta | 300 |

```
ttcagaaatt acgtaaaaga taccacaaat tacaataatt aacaacttga aatatttaaa      360
atacataaaa ataattaatt ttagaaattc caggcgtgcc acataaattg ggacaacgaa      420
ataatatata ctattatttt aaaattatgt aaaaaaataa ttctaaatca tgataattaa      480
taacttaaaa tattattaaa aatcatataa aaatttaaat aattgctcag gtttcagccg      540
tattacataa attaggataa aaaataatat atattgggcc ccgtgctggc acggggpccc      600 gtatctagtt tatataataa atatcgtttc tagtctatct cttctgatgc taaataaagt      660
ctgtgattat cttttaattt tttctactca gcatggggtg ccgtatctag tttatataat      720
aaatatcgtt tctagtctat ctcttctgat gctaaataaa gtcagtgatt attttttaat      780
tttttctact aggtaatgta aaattcttat gttaaccaaa taaattgaga caaattaatt      840
cagttaacca gagttaagag taaagtacta ttgcaagaaa atatcaaagg caaagaaaa       900 gatcatgaaa gaaaatatca agaaaaaga agaggttaca atcaaactcc cataaaactc       960
caaaaataaa cattcaaatt gcaaaaacat ccaatcaaat tgctctactt cacggggccc     1020
acgc                                                                 1024

<210> SEQ ID NO 23
<211> LENGTH: 342
<212> TYPE: DNA
<213> ORGANISM: Solanum tuberosum

<400> SEQUENCE: 23
aaaattctta tgttaaccaa ataaattgag acaaattaat tcagttaacc agagttaaga      60
gtaaagtact attgcaagaa atatcaaagg caaagaaaaa gatcatgaaa gaaaatatc      120 aaagaaaaag aagaggttac aatcaaactc ccataaaact ccaaaaataa acattcaaat     180
tgcaaaaaca tccaatcaaa ttgctctact tcacggggcc cacgccggct gcatctcaaa     240
ctttcccacg tgacatccca taacaaatca ccaccgtaac ccttctcaaa actcgacacc     300
tcactctttt tctctatatt acaataaaaa atatacgtgt cc                        342

<210> SEQ ID NO 24
<211> LENGTH: 151
<212> TYPE: DNA
<213> ORGANISM: Solanum tuberosum

<400> SEQUENCE: 24
cattcaaatt gcaaaaacat ccaatcaaat tgctctactt cacggggccc acgccggctg      60
catctcaaac tttcccacgt gacatcccat aacaaatcac caccgtaacc cttctcaaaa     120
ctcgacacct cactcttttt ctctatatta c                                    151

<210> SEQ ID NO 25
<211> LENGTH: 1024
<212> TYPE: DNA
<213> ORGANISM: Solanum tuberosum

<400> SEQUENCE: 25
taatataaca taccatgggt ggagctagaa gtctgattac aaatttcgtc aaattcaaca      60
atatttgctt aaataatata tttgtatagt aattttttt acaaaatata tacaaattta     120
ggtcaaggat tcagttatta acccttaaa atcgtgtcat aaaattcaat gttaaaattc      180
tgactttccc cgtgcttaac attacttatc aaatttatgt ttctgtgtag aaaagtacta     240
gtactactct tgactcgtc tagacgtcta ctatagatcc cttagatta aaaactccag       300 ttttaatatt ttcctcacaa ttattattct taatctacca cctaccggag tcacaaatat     360
```

-continued

```
attaaatgaa aatattctat ctattaattt atgatctacc tattgataat ttgtaatcta      420
gtcaaaatga tggcaaaaaa aatataatat ctagactgaa gttcttagtc aatagcgtaa      480
atgaaagaaa aaaaaaaaag ctcaagaaga aacatgatat ctttgttgct ctgattcgta      540
aaaaaaaaaa catagtaact tcataaaata tcttatcctt tggacagagc gatgaaaaaa      600
atatattact agtaatactg agattagtta cctgagacta tttcctatct tctgttttga      660
tttgatttat taaggaaaat tatgtttcaa cggccatgct tatccatgca ttattaatga      720
tcaatatatt actaaatgct attactatag gttgcttata tgttctgtaa tactgaatat      780
gatgtataac taatacatac attaaattct ctaataaatc tatcaacaga agcctaagag      840
attaacaaat actactatta tccagactaa gttattttc tgtttactac agatccttcc       900
aagaacaaaa acttaataat tgtatggctg ctatacataa ttccccacct accgcttcct      960
ggaataattg atatggaagc cgcctctaaa attgataat tatactgttt tacatattat       1020
ataa                                                                   1024

<210> SEQ ID NO 26
<211> LENGTH: 200
<212> TYPE: DNA
<213> ORGANISM: Solanum tuberosum

<400> SEQUENCE: 26
aagttatttt tctgtttact acagatcctt ccaagaacaa aaacttaata attgtatggc       60
tgctatacat aattccccac ctaccgcttc ctggaataat tgatatggaa gccgcctcta      120
aaattgaata attatactgt tttacatatt atataaagca aggtatagcc caatgaattt      180
tcattcaaaa gctagcaata                                                  200

<210> SEQ ID NO 27
<211> LENGTH: 460
<212> TYPE: DNA
<213> ORGANISM: Solanum tuberosum

<400> SEQUENCE: 27
ctagtaatac tgagattagt tacctgagac tatttcctat cttctgtttt gatttgattt       60
attaaggaaa attatgtttc aacggccatg cttatccatg cattattaat gatcaatata      120
ttactaaatg ctattactat aggttgctta tatgttctgt aatactgaat atgatgtata      180
actaatacat acattaaatt ctctaataaa tctatcaaca gaagcctaag agattaacaa      240
atactactat tatccagact aagttatttt tctgtttact acagatcctt ccaagaacaa      300
aaacttaata attgtatggc tgctatacat aattccccac ctaccgcttc ctggaataat      360
tgatatggaa gccgcctcta aaattgaata attatactgt tttacatatt atataaagca      420
aggtatagcc caatgaattt tcattcaaaa gctagcaata                            460

<210> SEQ ID NO 28
<211> LENGTH: 1024
<212> TYPE: DNA
<213> ORGANISM: Brassica sp.

<400> SEQUENCE: 28
attgagcttg aaggaacatt cgagcagata aacgaagcga cgcaatggt tagagagctg        60 attgggaggc ttaattccgc atctaggaga ccacctggtg gcggtggtgg cgggggtggg      120
cttggttctg aagggaaacc acatccagga agcaacttca agacgaagat gtgtgagaga      180
ttctctaaag gaagctgtac atttggtgat agatgtcact ttgctcacgg ggaagcagag      240
```

```
ctacgcaggt catgaattgc gcctagagtt actggtgaaa caagtctctt tcatttgttg      300
tggtgattcc taatatcatc ttctcctact tgtttttagt tgtcttcgtt ttttgaaact      360
acaatgttta gttttcattg tcagtgtaag ttttcccccat ttggtgtttt tttagaatct     420
agtttgaatt tgagatgggg caagcttgat gaatgattgg caaaacagtg gttaggattt      480
gtgtgctgtc tctacttaat atttcatgtt ttatctactt tattttggtc agcaagttga     540
tgtgtttctc tgatgtgtgt gtgattatca gcttagatta ttttgtgagt atgctagact     600
gtataactaa tcgttgtcga tgttatagtt ctcttataat gtttgataga ctatataact     660
aaaaattcat gttattaata gccgtcgctg atagtaacag ctgaataaat gaatgaaat      720 catggtaggt gatgatcttt aaagaatgtt aaaaataatg tgtcgttata agcggtaatg     780
catagaaaaa ctctaatcat cttaacataa gagagagcga tagctttaat aaagtactta     840
aattaattac tagtcggcag tcgctgccta cttgtgtacc acctaaatta atttattata     900
atatatgacg aatctccaaa gtacatcaca cacactcggg gctattcacg tgatctcaac     960
cacaatgtct gcagatattt ttttaagttt tcttctcaca tgggagaaga agaagccaag    1020
cacg                                                                 1024

<210> SEQ ID NO 29
<211> LENGTH: 441
<212> TYPE: DNA
<213> ORGANISM: Brassica sp.

<400> SEQUENCE: 29
ccggctacca ctaacttcta cagttctact tgtgagtcgg caaggacgtt tcctcatatt       60
aaagtaaaga catcaaatac cataatctta atgctaatta acgtaacgga tgagttctat     120
aacataaccc aaactagtct ttgtgaacat taggattggg taaaccaata tttacatttt     180
aaaaacaaaa tacaaaaaga aacgtgataa actttataaa agcaattata tgatcacggc     240
atctttttca cttttccgta aatatatata agtggtgtaa atatcagata tttggagtag     300
aaaaaaaaaa aaagaaaaaa gaaatatgaa gagaggaaat aatggagggg cccacttgta     360 aaaagaaag aaaagagatg tcactcaatc gtctcacacg ggcccccgtc aatttaaacg     420
gcctgccttc tgcccaatcg c                                              441

<210> SEQ ID NO 30
<211> LENGTH: 1024
<212> TYPE: DNA
<213> ORGANISM: Brassica sp.

<400> SEQUENCE: 30
aagctttctt catcggtgat tgattccttt aaagacttat gtttcttatc ttgcttctga      60
ggcaagtatt cagttaccac ttatattctg gactttctga ctgcatcctc atttttccaa     120 catttttaaat ttcactattg gctgaatgct tcttctttga ggaagaaaca attcagatgg    180
cagaaatgta tcaaccaatg catatataca aatgtacctc ttgttctcaa acatctatc     240 ggatggttcc atttgctttg tcatccaatt agtgactact ttatattatt cactcctctt    300
tattactatt ttcatgcgag gttgccatgt acattatatt tgtaaggatt gacgctattg    360
agcgtttttc ttcaattttc tttatttttag acatgggtat gaaatggttg ttagagttgg   420
gttgaatgag atatacgttc aagtgaatgg cataccgttc tcgagtaagg atgacctacc   480
cattcttgag acaaatgtta catttagta tcagagtaaa atgtgtacct ataactcaaa    540
ttcgattgac atgtatccat tcaacataaa attaaaccag cctgcacctg catccacatt    600
```

```
tcaagtattt tcaaaccgtt cggctcctat ccaccgggtg taacaagacg gattccgaat    660
ttggaagatt ttgactcaaa ttcccaattt atattgaccg tgactaaatc aactttaact    720
tctataattc tgattaagct cccaatttat attcccaacg gcactacctc caaaatttat    780
agactctcat ccccttttaa accaactatg taaacgtttt tttttttaat tttatgaagt    840
taagttttta ccttgttttt aaaaagaatc gttcataaga tgccatgcca gaacattagc    900
tacacgttac acatagcatg cagccgcgga gaattgtttt cttcgccac ttgtcactcc     960 cttcaaacac ctaagagctt ctctctcaca gcacacacat acaatcacat gcgtgcatgc   1020
atta                                                                1024

<210> SEQ ID NO 31
<211> LENGTH: 2164
<212> TYPE: DNA
<213> ORGANISM: Brassica napus

<400> SEQUENCE: 31
ctgcaggtac aaagaggagc tctacttagt ttatgacttt atgcccagtg gaagccttga     60
caagtacctc tacaccgaat cagatcaaga atatatgaag ttcacaagaa aaatcttagt    120
atttgtttac tctatctttc tatgtaaatg tgttttgct tttcaaaaaa gagctttgag     180
aaaaattaaa gaagataact tgtcttaacc tattttggt tcgggttttg cggagaactt     240
ttgaaaataa tgacaactag gtgttttgcc ctcgatgcgg atttaaacat ttcataatt     300 tttgaaaagt tctttgtaca ctatattcat tatactaaaa taaatcttaa ataatttaa    360 tattatattt taaattatat aattaaaaaa caattatttg attaatattt aattatataa    420
tttatgtttt aacttttttac taaatacttt ttcagataac aatacaatac atatatatag    480
aaattatctt tttttaaat tatattttta gatcttggat aatttaatat tatattttta    540
ttatataatt aagaatttta tttgattaat atttagttat ataattcatg tttaaactt     600 tatatatata attcatgttt ttaactttt actaaaaatac ttttttcagat aacaatacaa    660 tatatacata aattatctct ttttaaaatt atattttcag atttttggata atgcttacta    720 ttattaattt taatcaatta tctaatcaaa taaattaaaa ttttgttta taggatataa     780 acgatattaa tcattctaat ttttaacgtg agagttcgat tccaaaaatt tacttcgcaa    840
ataatagtat atatctagct tattagggct ttaaaaggtt taggtttctt tacgctttaa    900
ttgttttttt taactataat tgtaaacgtg ttaaacataa ctaatcagtg ttaaaacttg    960 ctttattta ttttttccaac ttttagatta aagcataaag tgttaccata aaaagaaga   1020 ttaaagcata aagagatatc atttggtata atatttatgc caacgtataa tttgttttta   1080
tcttttatgc aaacgcatac acatgtggac ttgaaagaaa cgacaatgag gacacttaac   1140
acaaactccc aaaatgtcac ttaaagctat agttctgtca cggtctctca atggaaaatc   1200
gtggtgctat caatgaaaaa acgttgtgct gaaactggca gagcacaaaa ctatagtcta   1260
aaaaggattg aatgaagcaa aaaatgcaag aaccaaaggc acaacgattc tcacatttga   1320
atgatattag aaatattagt ttcatttgcc aagtggacac atccacgtgg tagaggagcc   1380
atgccacttg tctctttcgt gggttctcac gcccgagtta catttgaaaa ttacaaaata   1440
aaagaacatt ttgtatatgt attgacattt ttacccttgc atatacatgt gtttagatct   1500
aaattcacaa ctaatccatc tcttatcatt tttagttaac taagagcatc aatgttaacc   1560
atgattctaa tttgaaatta attcatgatt tgatattttta ttattttatt tttatattttt   1620 ttggttaaaa acagactctt atatctttta tttaagagat agttcttaat tttcttaatt   1680
```

```
aaaagttaag aaacggttct taaccaaatg taaaaaccat attgtaagag ctcggattta   1740
ttatgatcta aggaactcac gagtcaattc acctaatcaa atctaaaata tagtaattat   1800
agctttaccg acatgtgata ctgccaaaaa taataaataa tatatagaca caagaaggat   1860
gtgatagtga ggaatctgga gggcatttta gaactgatgc tcgattaaaa acagaaaata   1920
atcttcaaaa ttttaattta cacgatagat gacgtcattt ttccatttgt tttgttaatt   1980
agttatttat ttccttctct ctctttcctc cgagtgtaga ctcttccctc aaaccgctgt   2040
ttctcataac catattctct ttctgtggac gaaactcaac cttaagagac cagagagagc   2100
attagcctag agagagctcg ctcgtgtctg aaagaacatc aaacctcgta tcaaaaaaaa   2160
gaaa                                                               2164
```

<210> SEQ ID NO 32
<211> LENGTH: 1024
<212> TYPE: DNA
<213> ORGANISM: Glycine max
<220> FEATURE:
<221> NAME/KEY: modified_base
<222> LOCATION: (143)
<223> OTHER INFORMATION: a, c, g, t, unknown or other
<220> FEATURE:
<221> NAME/KEY: modified_base
<222> LOCATION: (936)
<223> OTHER INFORMATION: a, c, g, t, unknown or other

<400> SEQUENCE: 32

```
cagaaaagg gaatagtttg gataaaatag attttaggtc tctcaattcc tagtcaaaat     60
tagtctcaat cattatgctt taaaaatgat gattttgaca cttgggagat aacaatattt    120
cttaaagttt gattctcaag ttngtatata tgaaatagtg tgttgggaga agtaaactct    180
taaaataaat tttatatttt tagagatgat tctctcattc ttatgaagga gatatactag    240
aaaaaaaatg attttatttt ttttatttttt tattatgaaa cttaagaatt aagataccag    300
gatgagggac aaaagtcatt aattattaaa aaaaaataca agaatcaaga ttattatttt    360
taaaatataa aaaaaactaa ttttgatata taaagaaatc caggggatat aatacacact    420
ctatcccaaa tatttggtta aaccccccagg ggcccaatgt ttcgtctttc ctcaacagta    480
taaattgcta atgatattat ttgtcttgaa ttggttcctg tggctagcat atctctgcaa    540
cttgtgcaac catttggtaa ttcaattaag aatatataat atactttaaa tttactagga    600
tgcataaaaa accctgtgac ttgtctgacc aagacttgcc aaatttttt atcatgcatt    660 acaaaaccca gccatttgtt tttattttttt ggatttctat tctttccaaa tgaaggccta    720
acagataaat tgcatgtcta atttccccctt gttattagag aaataagaaa ttataagctt    780
ttgctttgac ttttgaacat attttacact cttttgcaggt tgcttttat cttggaagac    840 cagaggagtc aaaataacag tgtcgcggta agtaagtgct cgacattctg gaatagtctc    900
ttattgcgta ttgtgccatc attttgaggc cttgtnggct tgcatcacca ttgaaagaaa    960
ttagtttgat ggttaaaatg gtatacccttt tgtcttcatt attactcgaa ttacattag   1020 aaag                                                               1024
```

<210> SEQ ID NO 33
<211> LENGTH: 2024
<212> TYPE: DNA
<213> ORGANISM: Medicago sativa

<400> SEQUENCE: 33

```
aaatgaaaga gagttaagga ttgaaatgaa actggtaaaa aacagcttat tttaaaacat     60
```

| | | |
|---|---|---|
| cttattcaaa acaacttatt ttatttaaaa caatttattt tattcaaaac atgttttgaa | 120 | |
| taagttgttt tttgaaaata agctgttttg aataagctgt ttttaaaata aggtgttttt | 180 | |
| cataaaataa gttgtttttg ttaaaataag ttgttttttc aaataagctg ttttgaataa | 240 | |
| gctgtttttt tttaaataag ttgttttgaa taagctgttt tttttaaata agttgttttt | 300 | |
| ttaaataagc tgttttgaat aagttgtttt aaaataaggt gttttgcata aaataagctg | 360 | |
| ttttgaataa gttgttttga ataagttgtt tgaataagc tgttttttttt aaaaataaat | 420 | |
| tgttttcata aaataagctg tttttaaaat aaggtgtttt gtataaataa gcttttttaaa | 480 | |
| ataagctatt caataagtt gttttttttgg aaagatccaa caaagagttc aagtggtttc | 540 | |
| tttaaaataa aataaaaagt tcaagtggtt tggttcggtt caaacggttc ggttcggttc | 600 | |
| aagatggttc ggttatggtt caagaactgt taataaatta acggttcggt tcgtgaacca | 660 | |
| ttataacgat tcggttatt ttggttcggt tcggttcgcg cggttcggtt cggttcatgg | 720 | |
| ttcttttttgc ccaccctaa agaaaataaa tgaatggtgg ttgagtattc ttaaaatgat | 780 | |
| ttgttttcta gaataaagag ttaataaggg ggtcaaaaga gcaaccatct aaggtaaact | 840 | |
| ctcactttta gagttgatgc ggttaaaatt tggatataac acttttgttg accaaaatgt | 900 | |
| ctcttatgaa taagactgaa agaagtaata atttaaaaaa aaaaaatccg gctgttgcat | 960 | |
| ttttttaaaac attaatccga agaaaagatg tttgaaaatt gtttataatg agaagttatt | 1020 | |
| ttgagttttt tttccttcta aaaaaataat gttatttttca ttatgtttaa cacccataaa | 1080 | |
| actacttctg ttttttttaaa gaatctctaa aaatcaattt ctaaacgtca aaagttttttt | 1140 | |
| atacaattag tttagggtgt ttctatgagg gtttgataat atttctacga ctatatatat | 1200 | |
| ttttttttta aggaaattct acgactactt gtagttggaa tatgggaata cgactacttt | 1260 | |
| tctatgaaga gcaggttacg gtagacacaa aagctgactc ttgcgcaaag cttgttcaac | 1320 | |
| ccaatagtga catattagga aatgaaaaat accctaatgc ctccttttca atactcaaga | 1380 | |
| aaagtcctcc ttaccatatt gtcccatttt ctttaagagc agagaagaac acatttgttc | 1440 | |
| acaccaacat gattttttgta tgcttgtaaa tgaaaagctt ctagttatcc agctcaaccc | 1500 | |
| gtgactaagg tctattcaat ttgcttagaa atgaggcatc aattatgatg caaattttttg | 1560 | |
| tactcattac tcaattcaaa aactatatga acttgtggtg tcacgtaagt gaataacact | 1620 | |
| atctaaattt gagtacagta cttctcctgt cacggggaga aaaacactca aaatcaattg | 1680 | |
| ttagagataa attttgtatc ataaattaat taattttaca attacatcaa taaatgtcat | 1740 | |
| tgtttaatca aataatatat gacaaaactt ctttgaaaat atactgagca aaacaaaac | 1800 | |
| tattaattgc atgcaacggc aacacatttc tgtttacaat tatattcggt gagtactcag | 1860 | |
| tcagtataac ccaattacca catatgcacg aattctctta gtgggtccac attgtggtgg | 1920 | |
| ttgagtggga cccaattgta atggatggcc cacatacacc aaactcaacc aaacaatttc | 1980 | |
| tcataaagtt ctatataata gcaatccact ttgcatcatt gagg | 2024 | |

<210> SEQ ID NO 34
<211> LENGTH: 448
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 34

| | | |
|---|---|---|
| caccaacatg atttttgtat gcttgtaaat gaaaagcttc tagttatcca gctcaacccg | 60 | |
| tgactaaggt ctattcaatt tgcttagaaa tgaggcatca attatgatgc aaattttttgt | 120 | |

```
actcattact caattcaaaa actatatgaa cttatggtgt cacgtaagtg aataacacta      180
tctaaatttg agtacttctc ctgtcacggg gagaaaaaca ctcaaaatca attgcatgca      240
acggcaacac atttctgttt acaattatat tcggtgagta ctcagtcagt ataacccaat      300
taccacatat gcacgaattc tcttagtggg tccacattgt ggtggttgag tgggacccaa      360
ttgtaatgga tggcccacat acaccaaact caaccaaaca atttctcata aagttctata      420
taatagcaat ccactttgca tcattgag                                        448

<210> SEQ ID NO 35
<211> LENGTH: 1021
<212> TYPE: DNA
<213> ORGANISM: Medicago sativa

<400> SEQUENCE: 35
atagtggacc agttaggtag gtggagaaag aaattattaa aaaatatat ttatatgttg       60 tcaaataact caaaaatcat aaaagtttaa gttagcaagt gtgcacattt ttatttggac     120
aaaagtattc acctactact gttataaatc attattaaac attagagtaa agaaatatgg     180
atgataagaa taagagtagt gatattttga caacaatttt gttacaacat ttgagaaaat     240
tttgttgttc tctcttttca ttggtcaaaa acaatagaga gagagagaga aaaaggaaga     300
gggagaataa aaacataatg tgagtatgag agagaaagtt gtacaaaagt tgtaccaaaa     360
tggttgtaca aatatcattg aggaatttga caaaagctac acaaataagg gttaattgct     420
gtaaataaat aaggatgacg cattagagag atgtaccatt agagaatttt tggcaagtca     480
ttaaaaagaa agaataaatt atttttaaaa ttaaaagttg agtcatttga ttaaacatgt     540
gattatttaa tgaattgatg agagagttgg attaaagttg tattaatgat tagaaatttgg     600 tgtcaaatt aatttgacat ttgatctttt cctatatatt gccccataga gtcatttaac     660
tcatttttat atttcataga tcaaataaga gaaataacgg tatattaatc cctccaacaa     720
aaaaaaaaaa aaaacggtat attactaaa aaatctaagc cacgtaggag gataacatcc     780
aatccaacca atcacaacaa tcctgatgag ataacccact ttaagcccac gcactctgtg     840
gcacatctac attatctaaa tcacacattc ttccacacat ctgagccaca caaaaaccaa     900
tccacatctt tatcatccat tctataaaaa atcacacttt gtgagtctac actttgattc     960
ccttcaaaca catacaaaga gaagagacta attaattaat taatcatctt gagagaaagc    1020
c                                                                   1021

<210> SEQ ID NO 36
<211> LENGTH: 858
<212> TYPE: DNA
<213> ORGANISM: Medicago sativa

<400> SEQUENCE: 36
agagaggagg cagtgtacac aggggcagag agaggtgagt cgtctttctg gtagggctgg       60
tgttggggat agtggttggt ttgagagtca ggtggtgagg agggttggcg atggggttga     120
tacgttgttt tggttggata ggtggttagg agatgctcct ttttgtgttt gtttcaggag     180
gttgtttgag ttaacagaga acaaatttgt gtctgtggct aatttgttat ctgttgactc     240
ggagcagtgg ggggaggtgt tgaggtgaag cgtatggtgg cagaggtggt ggcagaggtg     300
aagcgtatgg tggcagctga gggaggcagt gtacacagag gtggagagag aggagagaga     360
agagagaaga gagagaaaat ggagaagaga gaagagaaga gagagaagac aaattttgt     420 gtgtgtgacc aaaccaaaat tcttggtcct ggtccacaca agattttctc ccaaccaagg     480
```

```
tacaagaata ccacgatcca agagtgccac gttgcaacat cataaccgtt caatagtaag      540
agataatcga acggccataa ttaattttca acaaacccac ttttttcctc ctactttgc      600 aacttgtccc tcatcaccta ccaaacacac atagcacacc aacacacata ataatattat    660
aataattgta aatatatgta gcctccaaat tagaaagaaa cctctatata aagcctaact    720
acttccttca caaatcagga aattcacaac tctaatattc atttctttcc taatcattag    780
aatttccatt cttataaaat tctaggtacc accacacaac aaataaagga acattaatca    840
atactattaa gatggatc                                                  858

<210> SEQ ID NO 37
<211> LENGTH: 1008
<212> TYPE: DNA
<213> ORGANISM: Medicago sativa

<400> SEQUENCE: 37
cttctattaa tgatttaatc aacctttttt aaaatacgaa ggtgacctta ttttgcaaat     60
aatccatgca tggaaatgca tcatcctttt gaaaatggga ttatctgaat tcttaagtta    120
cgtgaaaatt taatacattt cattttagat aaatttatta ttaaaattca cacttagatg    180
gcctaaaaat taacacttat ttttaacaat tcaaataaaa tatacgacga aatgagtgta    240
atttagttgg ttaagcatcg tcaagcttgg agagaaagat catagtttga tctttgaaaa    300
ctacactatt gaaagggtg aagatatcta aacatccaaa caaaatttat tttgatagtc     360
gattcaaatt atcaaaattt gtgaaaatat tttgtaaatt gttaagttgg caaaaatatg    420
ttaattttca aattaccatt tgcacatttt tctaatctca aatcacattt aagggatgtt    480
gactacttta gttttgtaca aatctttaca attttaacat ttataaaatg tgtttcggta    540
gataaaaagt gtgagtattg tttataagag attgtgtttt tcttttgttt aaacttataa    600
aataaatata tattttattt tattttaatg tgagattgta agaattcatt ataagattat    660
gtcattccct caaaagaaaa ttagatgatg tcatttttcat aactcattt ctataaatac     720 agaaaatcct caaaaatgaa aaacctcagt caaaaaataa aagaaaaaca tcaatagtgg    780
actggcccac actcattgct ttgctttagt ataagaaagt agacctcacc aaccacgaac    840
cggacgccaa ccggttcaac caaacattac accaattttc cttaaccata ccggttttc     900 cctcccttat ataaccatct tcctacctct tatctaacca agctccattc aactcttcaa    960
cacatatcag aaacagaaaa agaagcaaaa cattccaaga atttaaca               1008

<210> SEQ ID NO 38
<211> LENGTH: 171
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 38
catcaatagt ggactggccc acactcattg ctttgcttta gtataagaaa gtagacctca     60
ccaaccacga accggacgcc aaccggttca accaaacatt acaccaattt tccttaacca    120
taccggtttt tccctccctt atataaccat cttcctacct cttatctaac c             171

<210> SEQ ID NO 39
<211> LENGTH: 1024
<212> TYPE: DNA
<213> ORGANISM: Lycopersicon esculentum
```

<400> SEQUENCE: 39

```
aagcttctta aaaaggcaaa ttgattaatt tgaagtcaaa ataattaatt ataacaatgg        60
taaagcacct taagaaacca tagtttgaaa ggttaccaat gcgctatata ttaatcaact       120
tgataatata aaaaaattt caattcgaaa agggcctaaa atattctcaa agtattcgaa        180
atggtacaaa actaccatcc gtccacctat tgactccaaa ataaaattat tatccacctt      240
tgagtttaaa attgactact tatataacaa ttctaaattt aaactatttt aatacttta        300
aaaatacatg gcgttcaaat atttaatata atttaattta tgaatatcat ttataaacca      360
accaactacc aactcattaa tcattaaatc ccacccaaat tctactatca aaattgtcct      420
aaacactact aaaacaagac gaaattgttc gagtccgaat cgaagcacca atctaattta      480
ggttgagccg catatttagg aggacacttt caatagtatt ttttcaagc atgaatttga       540
aatttaagat taatggtaaa gaagtagtac acccgaatta attcatgcct ttttaaata       600
taattatata aatatttatg atttgtttta aatattaaaa cttgaatata ttattttaa       660
aaaaattatc tattaagtac catcacataa ttgagacgag gaataattaa gatgaacata    720
gtgtttaatt agtaatggat gggtagtaaa tttatttata aattatatca ataagttaaa    780
ttataacaaa tatttgagcg ccatgtattt taaaaatat taaataagtt tgaatttaaa    840
accgttagat aaatggtcaa ttttgaaccc aaaagtggat gagaagggta ttttagagcc    900
aataggggga tgagaaggat attttgaagc caatatgtga tggatggagg ataattttgt   960
atcatttcta atactttaaa gatattttag gtcattttcc cttctttagt ttatagacta   1020
tagt                                                                   1024
```

<210> SEQ ID NO 40
<211> LENGTH: 1024
<212> TYPE: DNA
<213> ORGANISM: Solanum tuberosum

<400> SEQUENCE: 40

```
tggcaggata tataccggtg taaacgaagt gtgtgtggtt gatccaaaat ctatcgtacc      60
tttagaaagt gtagctatga aggatagtct cacttatgaa gaactaccta ttgagattct    120
tgatcgtcag gtccgaaggt tgagaaaaat agaagtcgct tcagttacgg ctttgtggag    180
gagtaagggt accgaaccat gcatctcaat cttaatacta aaaaatgcaa caaaattcta    240
gtggagggac cagtaccagt acattagata ttatctttta ttactataat aatattttaa    300
ttaacacgag acataggaat gtcaagtggt agcggtagga gggagttggt tcagtttttt    360
agatactagg agacagaacc ggaggggccc attgcaaggc ccaagttgaa gtccagccgt    420
gaatcaacaa agagagggcc cataatactg tcgatgagca tttccctata atacagtgtc    480
cacagttgcc ttccgctaag ggatagccac ccgctattct cttgacacgt gtcactgaaa    540
cctgctacaa ataaggcagg cacctcctca ttctcacact cactcactca cacagctcaa    600
caagtggtaa cttttactca tctcctccaa ttatttctga tttcatgcat gtttccctac    660
attctattat gaatcgtgtt atggtgtata aacgttgttt catatctcat ctcatctatt    720
ctgattttga ttctcttgcc tactgaattt gaccctactg taatcggtga taaatgtgaa    780
tgcttcctct tcttcttctt cttctcagaa atcaattttct gttttgtttt tgttcatctg    840
tagcttggta gattcccctt tttgtagacc acacatcacg gatcccccaa acataattgt    900
aactgattta ttcttgaata acaacttcaa tgaaatcaag caacaaagct gatttcaaca    960
tgaaaaaaca gaacaagaaa acgaaaacag agcatcatcc atcaaagtgt aatctcagca   1020
```

```
                                              gatt                                                        1024

<210> SEQ ID NO 41
<211> LENGTH: 139
<212> TYPE: DNA
<213> ORGANISM: Solanum tuberosum

<400> SEQUENCE: 41
gaggggaaag tgaatgaaaa ataacaaagg cacagtaagt agtttctctt tttatcatgt         60
gatgaaggta tataatgtat gtgtaagagg atgatgttat taccacataa taagagatga       120
agagtctcat tttctgctt                                                    139

<210> SEQ ID NO 42
<211> LENGTH: 6087
<212> TYPE: DNA
<213> ORGANISM: Solanum tuberosum

<400> SEQUENCE: 42
tggcaggata taccggtg taaacgaagt gtgtgtggtt gatccaaaat ctatcgtacc          60
tttagaaagt gtagctatga aggatagtct cacttatgaa gaactaccta ttgagattct       120
tgatcgtcag gtccgaaggt tgagaaaaat agaagtcgct tcagttacgg ctttgtggag       180
gagtaagggt accgaaccat gcatctcaat cttaatacta aaaaatgcaa caaaattcta       240
gtggagggac cagtaccagt acattagata ttatctttta ttactataat aatatttaa        300 ttaacacgag acataggaat gtcaagtggt agcggtagga gggagttggt tcagtttttt       360
agatactagg agacagaacc ggaggggccc attgcaaggc ccaagttgaa gtccagccgt       420
gaatcaacaa agagagggcc cataatactg tcgatgagca tttccctata atacagtgtc       480
cacagttgcc ttccgctaag ggatagccac ccgctattct cttgacacgt gtcactgaaa       540
cctgctacaa ataaggcagg cacctcctca ttctcacact cactcactca cacagctcaa       600
caagtggtaa ctttttactca tctcctccaa ttatttctga tttcatgcat gtttccctac      660
attctattat gaatcgtgtt atggtgtata aacgttgttt catatctcat ctcatctatt       720
ctgattttga ttctcttgcc tactgaattt gaccctactg taatcggtga taaatgtgaa       780
tgcttcctct tcttcttctt cttctcagaa atcaatttct gttttgtttt tgttcatctg       840
tagcttggta gattccccct tttgtagacc acacatcacg gatccccccaa acataattgt      900 aactgattta ttcttgaata acaacttcaa tgaaatcaag caacaaagct gatttcaaca       960
tgaaaaaaca gaacaagaaa acgaaaacag agcatcatcc atcaaagtgt aatctcagca      1020
gattcaatag agactaactc gaggtgctct ctatgcaaat ctagcttttc gaatgagagt      1080
gataagagag tgaggattgt gaattatttt attgatgaag attggagaag tcaattattg      1140
attcacacac aggaattaag tgtgttgtgt tgcgtcctct tgtggaaatt aaatgtcacc      1200 cttttttat ttatcaataa aagcacgaaa atctcctgca ctactcccct gcactctctt       1260
atatttgtcc atttcccaca aatccctaac ttaattactt acccacactc aagcttaagc      1320
agaaaatgag actcttcatc tcttattatg tggtaataac atcatcctct tacacataca      1380 ttatataccct tcatcacatg ataaaaagag aaactactta ctgtgccttt gttattttttc    1440 attcacttcc ccctcccgcg ggttaaattc atgattttat gaactcaata gcttttcata      1500
atgagcaata ttatctttct tcagtagcaa atccacatgc tcttatgctc gctgaaatag      1560
ttttggccgt ggagtttcac catctatgtt tacaattgat tcttgtagct gcaggagggg      1620
gaagtgaatg aaaaataaca aaggcacagt aagtagtttc tcttttatc atgtgatgaa       1680
```

```
ggtatataat gtatgtgtaa gaggatgatg ttattaccac ataataagag atgaagagtc    1740
tcattttctg cttaagcttg agtgtgggta agtaattaag ttagggattt gtgggaaatg    1800
gacaaatata agagagtgca ggggagtagt gcaggagatt ttcgtgcttt tattgataaa    1860
taaaaaaagg gtgacattta atttccacaa gaggacgcaa cacaacacac ttaattcctg    1920
tgtgtgaatc aataattgac ttctccaatc ttcatcaata aaataattca caatcctcac    1980
tctcttatca ctctcattcg aaaagctaga tttgcataga gagcacctcg agttagtctc    2040
tattgaatct gctgagatta cactttgatg gatgatgctc tgttttcgtt ttcttgttct    2100
gttttttcat gttgaaatca gctttgttgc ttgatttcat tgaagttgtt attcaagaat    2160
aaatcagtta caattatgtt tgggtctaga gtgatgtgtg gtctacaaaa aggggaatct    2220
accaagctac agatgaacaa aaacaaaaca gaaattgatt tctgagaaga agaagaagaa    2280
gaggaagcat tcacatttat caccgattac agtagggtca aattcagtag gcaagagaat    2340
caaaatcaga atagatgaga tgagatatga acaacgtttt atacaccata acacgattca    2400
taatagaatg tagggaaaca tgcatgaaat cagaaataat tggaggagat gagtaaaagt    2460
taccacttgt tgagctgtgt gagtgagtga gtgtgagaat gaggaggtgc ctgccttatt    2520
tgtagcaggt ttcagtgaca cgtgtcaaga gaatagcggg tggctatccc ttagcggaag    2580
gcaactgtgg acactgtatt atagggaaat gctcatcgac agtattatgg gccctctctt    2640
tgttgattca cggctggact tcaacttggg ccttgcaatg ggcccctccg gttctgtctc    2700
ctagtatcta aaaactgaa ccaactccct cctaccgcta ccacttgaca ttcctatgtc    2760
tcgtgttaat taaaatatta ttatagtaat aaaagataat atctaatgta ctggtactgg    2820
tccctccact agaattttgt tgcatttttt agtattaaga ttgagatgca tggttcgagc    2880
tcccgcagtg tgccagggct gtcggcagat ggacataaat ggcacaccgc tcggctcgtg    2940
gaaagagtat ggtcagtttc attgataagt atttactcgt attcggtgtt tacatcaagt    3000
taatatgttc aaacacatgt gatatcatac atccattagt taagtataaa tgccaacttt    3060
ttacttgaat cgccgaataa atttacttac gtccaatatt tagttttgtg tgtcaaacat    3120
atcatgcact atttgattaa gaataaataa acgatgtgta atttgaaaac caattagaaa    3180
agaagtatga cgggattgat gttctgtgaa atcactggta aattggacgg acgatgaaat    3240
ttgatcgtcc atttaagcat agcaacatgg gtctttagtc atcatcatta tgttataatt    3300
attttcttga aacttgatac accaactttc attgggaaag tgacagcata gtataaacta    3360
taatatcaat tctggcaatt tcgaattatt ccaaatctct tttgtcattt catttcctcc    3420
cctatgtctg caagtaccaa ttatttaagt acaaaaaatc ttgattaaac aatttatttt    3480
ctcactaata atcacattta atcatcaacg gttcatacac gtctgtcact cttttttat    3540 tctctcaagc gcatgtgatc ataccaatta tttaaataca aaaaatcttg attaaacaat    3600
tcagtttctc actaataatc acatttaatc atcaacggtt catacacatc cgtcactctt    3660
tttttattct ctcaagcgca tgtgatcata ccaattattt aaatacaaaa aatcttgatt    3720
aaacaattca ttttctcact aataatcaca tttaatcatc aacggtttat acacgtccgc    3780
cactcttttt ttattctctc aagcgtatgt gatcatatct aactctcgtg caaacaagtg    3840
aaatgacgtt cactaataaa taatcttttg aatactttgt tcagtttaat ttatttaatt    3900
tgataagaat ttttttatta ttgaattttt attgttttaa attaaaaata agttaaatat    3960
atcaaaatat ctttaatttt tattttgaa aaataacgta gttcaaacaa attaaaattg    4020
agtaactgtt tttcgaaaaa taatgattct aatagtatat tcttttcat cattagatat    4080
```

-continued

```
tttttttaag ctaagtacaa aagtcatatt tcaatcccca aaatagcctc aatcacaaga    4140
aatgcttaaa tccccaaaat accctcaatc acaagacgtg tgtaccaatc ataccatatgg   4200 tcctctcgta aattccgaca aaatcaggtc tataaagtta cccttgatat cagtattata    4260
aaactaaaaa tctcagctgt aattcaagtg caatcacact ctaccacaca ctctctagta    4320
gagagatcag ttgataacaa gcttgttaac ggatccaaaa ttcttatgtt aaccaaataa    4380
attgagacaa attaattcag ttaaccagag ttaagagtaa agtactattg caagaaaata    4440
tcaaaggcaa aagaaaagat catgaaagaa aatatcaaag aaaagaaga ggttacaatc     4500 aaactcccat aaaactccaa aaataaacat tcaaattgca aaaacatcca atcaaattgc    4560
tctacttcac ggggcccacg ccggctgcat ctcaaacttt cccacgtgac atcccataac    4620
aaatcaccac cgtaaccctt ctcaaaactc gacacctcac tcttttctc tatattacaa     4680 taaaaaatat acgtgtcccc gcgggttaaa ttcatgattt tatgaactca atagcttttc    4740
ataatgagca atattatctt tcttcagtag caaatccaca tgctcttatg ctcgctgaaa    4800
tagttttggc cgtggagttt caccatctat gtttacaatt gattcttgta gctgcaggga    4860
cacgtatatt ttttattgta atatagaaaa aaagagtgag gtgtcgagtt ttgagaaggg    4920
ttacggtggt gatttgttat gggatgtcac gtgggaaagt ttgagatgca gccggcgtgg    4980
gccccgtgaa gtagagcaat ttgattggat gttttttgcaa tttgaatgtt tattttggaa   5040
gttttatggg agtttgattg taacctcttc ttttttctttg atattttctt tcatgatctt   5100
ttcttttgcc tttgatattt tcttgcaata gtactttact cttaactctg ttaactgaa    5160 ttaatttgtc tcaatttatt tggttaacat aagaattttt ctagagtgat gtgtggtcta   5220 caaaagggg aatctaccaa gctacagatg aacaaaaca aaacagaaat tgatttctga     5280
gaagaagaag aagaagagga agcattcaca tttatcaccg attacagtag ggtcaaattc    5340
agtaggcaag agaatcaaaa tcagaataga tgagatgaga tatgaaacaa cgtttataca    5400
ccataacacg attcataata gaatgtaggg aaacatgcat gaaatcagaa ataattggag    5460
gagatgagta aaagttacca cttgttgagc tgtgtgagtg agtgagtgtg agaatgagga    5520
ggtgcctgcc ttatttgtag caggtttcag tgacacgtgt caagagaata gcgggtggct    5580
atcccttagc ggaaggcaac tgtggacact gtattatagg gaaatgctca tcgacagtat   5640
tatgggccct ctcttgttg attcacggct ggacttcaac ttgggccttg caatgggccc    5700
ctccggttct gtctcctagt atctaaaaaa ctgaaccaac tccctcctac cgctaccact   5760
tgacattcct atgtctcgtg ttaattaaaa tattattata gtaataaaag ataatatcta   5820
atgtactggt actggtccct ccactagaat tttgttgcat ttttttagtat taagattgag   5880 atgcatggtt cgagctcctt caacatgtta taaacttcac atattcagtt gggaataggc   5940
tttataatga gttggactac gttatgtccc cctcaagtcc cagaattatg tgccccgta    6000 tgttataagt cccctctgcg ggcatcaatt tagtgatcac gccagacatg cctctatacc   6060
tcggccagga tatatttgtt ggtaatg                                         6087
```

<210> SEQ ID NO 43
<211> LENGTH: 654
<212> TYPE: DNA
<213> ORGANISM: Solanum tuberosum

<400> SEQUENCE: 43

```
gtaaatttct agtgattata ctgtacattt cgcataattt aggatcgtat ttgatatgtt      60
ttacgcttga ttgatcgaga acttaaagct tttctgatct gaaatttgtt ttttggcata    120
```

-continued

```
ctcgagttga gatcctggtt aaatcagtgt tatttcgatt gaattttagc aaaatttggt    180
gttgattttc agtattttca tggtttaatg tatataaaca agcttaattt ttcaaattca    240
agctcgttta acctttaat tacagcatat ttctggaaaa aagtttggtg atttctctag     300
atgttttatt cgagaaaaaa acaaaaacga aaaagggga aatgctgttc tgtatgtaca     360
aaaagtgatt gatcagcttt tggtcaccga catacatttg attagtacat acacgagtca    420
tacgagtata tttccgtgtg cactttattg ttttgaagga attctggatt tggttgattc    480
ctttttaaaa cttctaagtt tttttgtta cattttactc taattaagtc ttctctgtga     540
actgacaaat actcaccagg cacacattac aaccttcatt tgattatccg cgaacgatcc    600
attgcttttg tgtatattgc ttttgtattg actgattttg tattgtatta gcag          654
```

```
<210> SEQ ID NO 44
<211> LENGTH: 25
<212> TYPE: DNA
<213> ORGANISM: Solanum tuberosum

<400> SEQUENCE: 44
cattaccaac aaatatatcc tggcc                                            25

<210> SEQ ID NO 45
<211> LENGTH: 25
<212> TYPE: DNA
<213> ORGANISM: Lycopersicon esculentum

<400> SEQUENCE: 45
cattaccaac aaatatatcc tggcc                                            25

<210> SEQ ID NO 46
<211> LENGTH: 25
<212> TYPE: DNA
<213> ORGANISM: Lycopersicon esculentum

<400> SEQUENCE: 46
ctctacctct gaatatatcc tgcgg                                            25

<210> SEQ ID NO 47
<211> LENGTH: 25
<212> TYPE: DNA
<213> ORGANISM: Capsicum sp.

<400> SEQUENCE: 47
cattaccaac aaatatatcc tggcc                                            25

<210> SEQ ID NO 48
<211> LENGTH: 25
<212> TYPE: DNA
<213> ORGANISM: Medicago sativa

<400> SEQUENCE: 48
gtatacctct gtatacatcc tgccg                                            25

<210> SEQ ID NO 49
<211> LENGTH: 25
<212> TYPE: DNA
<213> ORGANISM: Hordeum sp.

<400> SEQUENCE: 49 ataccaaa tgatacatcc tgccc                                              25

<210> SEQ ID NO 50
```

<211> LENGTH: 25
<212> TYPE: DNA
<213> ORGANISM: Oryza sativa

<400> SEQUENCE: 50
acttactcaa ggatatatcc tggct                                              25

<210> SEQ ID NO 51
<211> LENGTH: 300
<212> TYPE: DNA
<213> ORGANISM: Figwort mosaic virus

<400> SEQUENCE: 51
gcctcaacaa ggtcagggta cagagtctcc aaaccattag ccaaaagcta caggagatca       60
atgaagaatc ttcaatcaaa gtaaactact gttccagcac atgcatcatg gtcagtaagt      120
ttcagaaaaa gacatccacc gaagacttaa agttagtggg catctttgaa agtaatcttg      180
tcaacatcga gcagctggct tgtggggacc agacaaaaaa ggaatggtgc agaattgtta      240
ggcgcaccta ccaaaagcat cttttgccttt attgcaaaga taaagcagat tcctctagta      300

<210> SEQ ID NO 52
<211> LENGTH: 304
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 52
aatgccccca tcaaggactg catcttttag gtggtaccag ctttccatga gcactttatc       60
ctgattcatg agattaagag cagaaatgga tacaccatct tcattcttaa ccaaatactt      120
agcaacagta gccaaaccat aaagtctctg aacctttcca tcttgttgag tacgaactga      180
acaagtgagg atattgtaac aagccaagag acgcaacatt cggtccaaca taactggtgc      240
atcagggtta gttgttggta gctgagaagc aatttcaata ggtgaaattt gagcaccagg      300
tcca                                                                    304

<210> SEQ ID NO 53
<211> LENGTH: 492
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 53
aatgccccca tcaaggactg catcttttag gtggtaccag ctttccatga gcactttatc       60
ctgattcatg agattaagag cagaaatgga tacaccatct tcattcttaa ccaaatactt      120
agcaacagta gccaaaccat aaagtctctg aacctttcca tcttgttgag tacgaactga      180
acaagtgagg atattgtaac aagccaagag acgcaacatt cggtccaaca taactggtgc      240
atcagggtta gttgttggta gctgagaagc aatttcaata ggtgaaattt gagcaccagg      300
tccagaattc aatctcacaa aaacctcatc aatcacaacc atgggttcaa caggtgaaac      360
tcaaataaca ccaacccaca tatcagatga agaagcaaac ctcttcgcca tgcaactagc      420
aagtgcttca gttcttccca tgattttgaa atcagctctt gaacttgatc tcttagaaat      480
cattgctaaa gc                                                          492

<210> SEQ ID NO 54

```
<211> LENGTH: 1027
<212> TYPE: DNA
<213> ORGANISM: Medicago sativa

<400> SEQUENCE: 54
gggcccatag tggaccagtt aggtaggtgg agaaagaaat tattaaaaaa atatatttat      60
atgttgtcaa ataactcaaa atcataaaa gtttaagtta gcaagtgtgc acatttttat     120
ttggacaaaa gtattcacct actactgtta taaatcatta ttaaacatta gagtaaagaa    180
atatggatga taagaataag agtagtgata ttttgacaac aattttgtta caacatttga    240
gaaaattttg ttgttctctc ttttcattgg tcaaaaacaa tagagagaga gagagaaaaa    300
ggaagaggga gaataaaaac ataatgtgag tatgagagag aaagttgtac aaaagttgta    360
ccaaaatggt tgtacaaata tcattgagga atttgacaaa agctacacaa ataagggtta    420
attgctgtaa ataaataagg atgacgcatt agagagatgt accattagag aatttttggc    480
aagtcattaa aaagaaagaa taaattattt ttaaaattaa agttgagtc atttgattaa     540
acatgtgatt atttaatgaa ttgatgagag agttggatta aagttgtatt aatgattaga    600
atttggtgtc aaatttaatt tgacatttga tcttttccta tatattgccc catagagtca    660
tttaactcat tttatatttt catagatcaa ataagagaaa taacggtata ttaatccctc    720
caacaaaaaa aaaaaaaaaa cggtatattt actaaaaaat ctaagccacg taggaggata    780
acatccaatc caaccaatca caacaatcct gatgagataa cccactttaa gcccacgcac    840
tctgtggcac atctcacatta tctaaatcac acattcttcc acacatctga gccacacaaa    900
aaccaatcca catctttatc atccattcta taaaaaatca cactttgtga gtctacactt    960
tgattccctt caaacacata caagagaag agactaatta attaattaat catcttgaga   1020
gaaagcc                                                            1027

<210> SEQ ID NO 55
<211> LENGTH: 853
<212> TYPE: DNA
<213> ORGANISM: Medicago sativa

<400> SEQUENCE: 55
agagaggagg cagtgtacac aggggcagag agaggtgagt cgtctttctg gtagggctgg     60
tgttggggat agtggttggt ttgagagtca ggtggtgagg agggttggcg atggggttga    120
tacgttgttt tggttggata ggtggttagg agatgctcct ttttgtgttt gtttcaggag    180
gttgtttgag ttaacagaga acaaatttgt gtctgtggct aatttgttat ctgttgactc    240
ggagcagtgg ggggaggtgt tgaggtgaag cgtatggtgg cagaggtggt ggcagaggtg    300
aagcgtatgg tggcagctga gggaggcagt gtacacagag gtggagagag aggagagaga    360
agagagaaga gagagaaaat ggagaagaga gaagagaaga gagagaagac aaatttttgt    420
gtgtgtgacc aaaccaaaat tcttggtcct ggtccacaca agattttctc ccaaccaagg    480
tacaagaata ccacgatcca agagtgccac gttgcaacat cataaccgtt caatagtaag    540
agataatcga acggccataa ttaattttca acaaacccac ttttttcctc ctactttttgc   600
aacttgtccc tcatcaccta ccaaacacac atagcacacc aacacacata ataatattat    660
aataattgta atatatgta gcctccaaat tagaaagaaa cctctatata aagcctaact     720
acttccttca caaatcagga aattcacaac tctaatattc atttctttcc taatcattag    780
aatttccatt cttataaaat tctaggtacc accacacaac aaataaagga acattaatca    840
atactattaa gat                                                     853
```

<210> SEQ ID NO 56
<211> LENGTH: 153
<212> TYPE: DNA
<213> ORGANISM: Medicago sativa

<400> SEQUENCE: 56
cggcaggatg tatacagagg tatacaattt tatattacat ttatatttgt gttaattcat      60
tgaattttca cttttatttt ttactttgat aatcaactgt gtaaagaatt atttgaaaaa     120
tatatataat ttatagaatt ttttttttgtt atg                                 153

<210> SEQ ID NO 57
<211> LENGTH: 91
<212> TYPE: DNA
<213> ORGANISM: Medicago sativa

<400> SEQUENCE: 57
ctagattatg cgggctaacg ggctgcccgc ggcccttttcg ggctagccct aacgggtacc     60
gggccccggc aggatgtata cagaggtata c                                    91

<210> SEQ ID NO 58
<211> LENGTH: 2932
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 58
cggcaggatg tatacagagg tatacaattt tatattacat ttatatttgt gttaattcat      60
tgaattttca cttttatttt ttactttgat aatcaactgt gtaaagaatt atttgaaaaa     120
tatatataat ttatagaatt ttttttttgtt atggggccca tagtggacca gttaggtagg   180
tggagaaaga aattattaaa aaaatatatt tatatgttgt caaataactc aaaaatcata    240
aaagtttaag ttagcaagtg tgcacatttt tatttggaca aaagtattca cctactactg    300
ttataaatca ttattaaaca ttagagtaaa gaaatatgga tgataagaat aagagtagtg    360
atattttgac aacaattttg ttacaacatt tgagaaaatt ttgttgttct ctctttttcat   420 tggtcaaaaa caatagagag agagagagaa aaaggaagag ggagaataaa aacataatgt    480
gagtatgaga gagaaagttg tacaaaagtt gtaccaaaat ggttgtacaa atatcattga    540
ggaatttgac aaaagctaca caaataaggg ttaattgctg taaataaata aggatgacgc    600
attagagaga tgtaccatta gagaattttt ggcaagtcat taaaaagaaa gaataaatta    660 ttttttaaaat taaagttga gtcatttgat taaacatgtg attatttaat gaattgatga    720
gagagttgga ttaaagttgt attaatgatt agaatttggt gtcaaattta atttgacatt    780
tgatcttttc ctatatattg ccccatagag tcatttaact cattttata tttcatagat     840 caaataagag aaataacggt atattaatcc ctccaacaaa aaaaaaaaa aaacggtata     900 tttactaaaa aatctaagcc acgtaggagg ataacatcca atccaaccaa tcacaacaat    960
cctgatgaga taacccactt taagcccacg cactctgtgg cacatctaca ttatctaaat  1020
cacacattct tccacacatc tgagccacac aaaaaccaat ccacatcttt atcatccatt    1080
ctataaaaaa tcacactttg tgagtctaca ctttgattcc cttcaaacac atacaaagag   1140
aagagactaa ttaattaatt aatcatcttg agagaaagcc ctgcagaatg ccccccatcaa  1200 ggactgcatc ttttaggtgg taccagcttt ccatgagcac tttatcctga ttcatgagat   1260
taagagcaga aatggataca ccatcttcat tcttaaccaa atacttagca acagtagcca   1320

```
aaccataaag tctctgaacc tttccatctt gttgagtacg aactgaacaa gtgaggatat    1380
tgtaacaagc caagagacgc aacattcggt ccaacataac tggtgcatca gggttagttg    1440
ttggtagctg agaagcaatt tcaataggtg aaatttgagc accaggtcca gctttagcaa    1500
tgatttctaa gagatcaagt tcaagagctg atttcaaaat catgggaaga actgaagcac    1560
ttgctagttg catggcgaag aggtttgctt cttcatctga tatgtgggtt ggtgttattt    1620
gagtttcacc tgttgaaccc atggttgtga ttgatgaggt ttttgtgaga ttgaattctg    1680
gacctggtgc tcaaatttca cctattgaaa ttgcttctca gctaccaaca actaaccctg    1740
atgcaccagt tatgttggac cgaatgttgc gtctcttggc ttgttacaat atcctcactt    1800
gttcagttcg tactcaacaa gatgaaaagg ttcagagact ttatggtttg gctactgttg    1860
ctaagtattt ggttaagaat gaagatgatg tatccatttc tgctcttaat ctcatgaatc    1920
aggataaagt gctcatggaa agctggtacc acctaaaaga tgcagtcctt gatggggca    1980 ttggatccat cttaatagta ttgattaatg ttcctttatt tgttgtgtgg tggtacctag    2040
aattttataa gaatggaaat tctaatgatt aggaagaaa tgaatattag agttgtgaat    2100
ttcctgattt gtgaaggaag tagttaggct ttatatagag gtttctttct aatttggagg    2160
ctacatatat ttacaattat tataatatta ttatgtgtgt tggtgtgcta tgtgtgtttg    2220
gtaggtgatg agggacaagt tgcaaaagta ggaggaaaaa agtgggtttg ttgaaaatta    2280
attatggccg ttcgattatc tcttactatt gaacggttat gatgttgcaa cgtggcactc    2340
ttggatcgtg gtattcttgt accttggttg ggagaaaatc ttgtgtggac caggaccaag    2400
aattttggtt tggtcacaca cacaaaaatt tgtcttctct ctcttctctt ctctcttctc    2460
cattttctct ctcttctctc ttctctctcc tctctctcca cctctgtgta cactgcctcc    2520
ctcagctgcc accatacgct tcacctctgc caccacctct gccaccatac gcttcacctc    2580
aacacctccc cccactgctc cgagtcaaca gataacaaat tagccacaga cacaaatttg    2640
ttctctgtta actcaaacaa cctcctgaaa caaacacaaa aaggagcatc tcctaaccac    2700
ctatccaacc aaaacaacgt atcaaccca tcgccaaccc tcctcaccac ctgactctca    2760
aaccaaccac tatccccaac accagccta ccagaaagac gactcacctc tctctgcccc    2820
tgtgtacact gcctcctctc tctagattat gcgggctaac gggctgcccg cggcccttc    2880 gggctagccc taacgggtac cgggcccgg caggatgtat acagaggtat ac           2932
```

<210> SEQ ID NO 59
<211> LENGTH: 676
<212> TYPE: DNA
<213> ORGANISM: Zea mays

<400> SEQUENCE: 59

```
ttccacggca gctgccaccg tcgctatcgc tgaccaaccc ggctggtcgc ctctgtgctc      60
catccatgca tgttacaact atgcagatgc agccgaaaca aacactggct agaaaggcag     120
cccaacgggc ctactgtcat cgctccggc atcctactgg tgggcccact tgcaccggcc     180
gatgaccagt tcatcatttt tctcgacgaa tttgtgcaca gaatttgcta aaaattcttc     240
gcacgtggca aaaccagggg gaaaatcgaa actagtcgg ggttttttta attccctgat     300
agaatagtcc ctgctaatca tccatgaaaa ccaaacacgt actctacgtc accgtcatgg     360
atggagcgag tgaactgatg attttttccc catcccgcac gcaacagcat gggtgacaac     420
aaccactccc gctgcggttg ggcgagcaca tctctacgca cttgacactc acgcaaacct     480
aacgcatact agagtaatca tcgccaccaa ctatcggcga cagaaacgat gggccccgct     540
```

```
tctcttaatc acggtgcttg aattagtgcg cgcatagtag tgaaaaataa tagtgaaaaa      600
taagcagtgc gtgttttggt gtggtggttg gtgagccgtc cgccccaata aaaacccctc      660
gcaccacctc gtccct                                                     676

<210> SEQ ID NO 60
<211> LENGTH: 89
<212> TYPE: DNA
<213> ORGANISM: Figwort mosaic virus

<400> SEQUENCE: 60
caagtgggga acaaaataac gtggaaaaga gctgtcctga cagcccactc actaatgcgt       60
atgacgaacg cagtgacgac cacaaaaga                                        89
```

GENE SILENCING

CROSS-REFERENCE TO RELATED PATENT APPLICATIONS

This regular U.S. patent application claims priority to U.S. provisional application Ser. Nos. 60/612,638, filed on Sep. 24, 2004, 60/619,959, filed on Oct. 20, 2004, 60/653,609, filed on Feb. 16, 2005, and 60/668,071, filed on Apr. 5, 2005, all of which are incorporated herein by reference.

FIELD OF THE INVENTION

The present invention relates to unique constructs for producing a nucleic acid product that downregulates or prevents expression of a desired target polynucleotide.

BACKGROUND OF THE INVENTION

Suppression of gene expression may be accomplished by constructs that trigger post-transcriptional or transcriptional gene silencing. These silencing mechanisms may downregulate desired polynucleotide or gene expression by chromatin modification, RNA cleavage, translational repression, or via hitherto unknown mechanisms. See Meister G. and Tuschl T., Nature, vol. 431, pp. 343-349, 2004.

A construct that is typically used in this regard contains a desired polynucleotide, which shares sequence identity with at least part of a target gene that is operably linked to a promoter and a terminator. As is well appreciated, the promoter initiates transcription, while the terminator ends transcription at a specific site and subsequently mediates polyadenylation. Such transcript processing is important for stability of the transcript and its transport from the nucleus and into the cytoplasm.

In this regard, the terminator plays an important role in conventional gene silencing constructs. For instance, WO 99/53050 describes a construct that comprises a promoter, a polynucleotide comprising a first sequence with homology to a target gene and a second sequence that is inverse complementary to the target gene, and a terminator. A terminator of conventional constructs does not necessarily have to be positioned immediately downstream from the desired polynucleotide. For instance, Mette and co-workers described a plasmid that contains a desired polynucleotide that is separated from an operably linked terminator by a hygromycin gene (Mette et al., EMBO J 18: 241-8, 1999; Mette et al., EMBO J 19: 5194-201, 2000).

Other conventional constructs designed to silence genes contain a polynucleotide in the sense or antisense orientation between promoter and terminator. Such a conventional gene silencing construct typically produces RNA transcripts that are similar in size, determined by the distance from transcription start to termination cleavage site and the poly-adenylated tail.

The present invention relates to new strategies and constructs for gene silencing that are generally more effective than conventional constructs. Furthermore, the present invention relates to new strategies and constructs for gene silencing using a polynucleotide that is not operably linked to a promoter and a terminator but is instead operably linked to two convergently-oriented promoters.

SUMMARY OF THE INVENTION

Strategies and constructs of the present invention can be characterized by certain features. A construct of the present invention, for instance, may not comprise a DNA region, such as a terminator, that is involved in 3'-end formation and polyadenylation. Alternatively, the construct may comprise a non-functional terminator that is naturally non-functional or which has been modified or mutated to become non-functional.

A construct may also be characterized in the arrangement of promoters at either side of a desired polynucleotide. Hence, a construct of the present invention may comprise two or more promoters which flank one or more desired polynucleotides or which flank copies of a desired polynucleotide, such that both strands of the desired polynucleotide are transcribed. That is, one promoter may be oriented to initiate transcription of the 5'-end of a desired polynucleotide, while a second promoter may be operably oriented to initiate transcription from the 3'-end of the same desired polynucleotide. The oppositely-oriented promoters may flank multiple copies of the desired polynucleotide. Hence, the "copy number" may vary so that a construct may comprise 2, 3, 4, 5, 6, 7, 8, 9, 10, 15, 20, 30, 40, 50, 60, 70, 80, 90, or 100, or more than 100 copies, or any integer in-between, of a desired polynucleotide ultimately flanked by promoters that are oriented to induce convergent transcription.

Alternatively, a first promoter may be operably linked to a first polynucleotide in "cassette A," for instance, and a second promoter may be operably linked to a second polynucleotide, e.g., "cassette B." The polynucleotides of each cassette may or may not comprise the same nucleotide sequence, but may share some percentage of sequence identity with a target nucleic acid of interest. The cassettes may be tandemly arranged, i.e., so that they are adjacent to one another in the construct. Furthermore, cassette B, for instance, may be oriented in the inverse complementary orientation to cassette A. In this arrangement, therefore, transcription from the promoter of cassette B will proceed in the direction toward the promoter of cassette A. Hence, the cassettes are arranged to induce "convergent transcription."

If neither cassette comprises a terminator sequence, then such a construct, by virtue of the convergent transcription arrangement, may produce RNA transcripts that are of different lengths.

In this situation, therefore, there may exist subpopulations of partially or fully transcribed RNA transcripts that comprise partial or full-length sequences of the transcribed desired polynucleotide from the respective cassette. Alternatively, in the absence of a functional terminator, the transcription machinery may proceed past the end of a desired polynucleotide to produce a transcript that is longer than the length of the desired polynucleotide.

In a construct that comprises two copies of a desired polynucleotide, therefore, where one of the polynucleotides may or may not be oriented in the inverse complementary direction to the other, and where the polynucleotides are operably linked to promoters to induce convergent transcription, and there is no functional terminator in the construct, the transcription machinery that initiates from one desired polynucleotide may proceed to transcribe the other copy of the desired polynucleotide and vice versa. The multiple copies of the desired polynucleotide may be oriented in various permutations: in the case where two copies of the desired polynucleotide are present in the construct, the copies may, for example, both be oriented in same direction, in the reverse orientation to each other, or in the inverse complement orientation to each other, for example.

In an arrangement where one of the desired polynucleotides is oriented in the inverse complementary orientation to the other polynucleotide, an RNA transcript may be produced that comprises not only the "sense" sequence of the first polynucleotide but also the "antisense" sequence from the second polynucleotide. If the first and second polynucleotides comprise the same or substantially the same DNA sequences, then the single RNA transcript may comprise two regions that are complementary to one another and which may, therefore, anneal. Hence, the single RNA transcript that is so transcribed, may form a partial or full hairpin duplex structure.

On the other hand, if two copies of such a long transcript were produced, one from each promoter, then there will exist two RNA molecules, each of which would share regions of sequence complementarity with the other. Hence, the "sense" region of the first RNA transcript may anneal to the "antisense" region of the second RNA transcript and vice versa. In this arrangement, therefore, another RNA duplex may be formed which will consist of two separate RNA transcripts, as opposed to a hairpin duplex that forms from a single self-complementary RNA transcript.

Alternatively, two copies of the desired polynucleotide may be oriented in the same direction so that, in the case of transcription read-through, the long RNA transcript that is produced from one promoter may comprise, for instance, the sense sequence of the first copy of the desired polynucleotide and also the sense sequence of the second copy of the desired polynucleotide. The RNA transcript that is produced from the other convergently-oriented promoter, therefore, may comprise the antisense sequence of the second copy of the desired polynucleotide and also the antisense sequence of the first polynucleotide. Accordingly, it is likely that neither RNA transcript would contain regions of exact complementarity and, therefore, neither RNA transcript is likely to fold on itself to produce a hairpin structure. On the other hand the two individual RNA transcripts could hybridize and anneal to one another to form an RNA duplex.

Hence, in one aspect, the present invention provides a construct that lacks a terminator or lacks a terminator that is preceded by self-splicing ribozyme encoding DNA region, but which comprises a first promoter that is operably linked to a first polynucleotide and a second promoter that is operably linked to second polynucleotide, whereby (1) the first and second polynucleotide share at least some sequence identity with each other, (2) the first promoter is oriented such that the direction of transcription initiated by this promoter proceeds towards the second promoter, and vice versa, and (3) this convergent arrangement produces a range of RNA transcripts that are generally different in length.

The desired polynucleotides may be perfect or imperfect repeats of one another, or perfect or imperfect inverse complementary repeats of one another. In the case of a construct that comprises a first polynucleotide and a second polynucleotide, the second polynucleotide may be fully or partially identical in nucleotide sequence to the first polynucleotide and oriented in the direct or inverse complementary orientation with respect to the first polynucleotide. Hence, the first and second polynucleotides may be perfect repeats of one another. On the other hand, the second polynucleotide may be an imperfect repeat of the first polynucleotide, that is the second polynucleotide may share sequence identity with the first polynucleotide, but is not fully or partially identical in sequence, i.e., the second polynucleotide is an imperfect repeat. That second polynucleotide also may be oriented as a direct repeat or positioned in the inverse complementary orientation with respect to the first polynucleotide.

Any of the polynucleotides described herein, such as a desired polynucleotide, or a first or second polynucleotide, for instance, may be identical to at least a part of a target sequence, or may share sequence identity with at least a part of a target sequence. When a desired polynucleotide comprises a sequence that is homologous to a fragment of a target sequence, i.e., it shares sequence identity with "at least a part of" a target sequence, then it may be desirable that the nucleotide sequence of the fragment is specific to the target gene, and/or the partial perfect or imperfect sequence of the target that is present in the desired polynucleotide is of sufficient length to confer target-specificity. Hence the portion of the desired polynucleotide that shares sequence identity with a part of a target sequence may comprise a characteristic domain, binding site, or nucleotide sequence typically conserved by isoforms or homologs of the target sequence. It is possible, therefore, to design a desired polynucleotide that is optimal for targeting a target nucleic acid in a cell.

In another embodiment, the desired polynucleotide comprises a sequence of preferably between 4 and 5,000 nucleotides, more preferably between 50 and 1,000 nucleotides, and most preferably between 150 and 500 nucleotides that share sequence identity with the DNA or RNA sequence of a target nucleic acid. The desired polynucleotide may share sequence identity with at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 300, 400, 500, or more than 500 contiguous nucleotides, or any integer in between, that are 100% identical in sequence with a sequence in a target sequence, or a desired polynucleotide comprises a sequence that shares about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 8%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% nucleotide sequence identity with a sequence of the target sequence. In other words the desired polynucleotide may be homologous to or share homology with the full-length sequence of a target sequence or a fragment thereof of a target sequence.

Hence, the present invention provides an isolated nucleic acid molecule comprising a polynucleotide that shares homology with a target sequence and which, therefore, may hybridize under stringent or moderate hybridization conditions to a portion of a target sequence described herein. By a polynucleotide which hybridizes to a "portion" of a polynucleotide is intended a polynucleotide (either DNA or RNA) hybridizing to at least about 15 nucleotides, and more preferably at least about 20 nucleotides, and still more preferably at least about 30 nucleotides, and even more preferably more than 30 nucleotides of the reference polynucleotide. For the purpose of the invention, two sequences that share homology, i.e., a desired polynucleotide and a target sequence, may hybridize when they form a double-stranded complex in a hybridization solution of 6×SSC, 0.5% SDS, 5×Denhardt's solution and 100 µg of non-specific carrier DNA. See Ausubel et al., section 2.9, supplement 27 (1994). Such sequence may hybridize at "moderate stringency," which is defined as a temperature of 60° C. in a hybridization solution of 6×SSC, 0.5% SDS, 5×Denhardt's solution and 100 µg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 h. For high stringency, the wash temperature is increased to typically a temperature that is about 68° C. Hybridized nucleotides may be those that are detected using 1 ng of a radiolabeled probe having a specific radioactivity of 10,000 cpm/ng, where the hybridized nucleotides are clearly visible following exposure to X-ray film at −70° C. for no more than 72 hours.

In one embodiment, a construct of the present invention may comprise an expression cassette that produces a nucleic acid that reduces the expression level of a target gene that is normally expressed by a cell containing the construct, by 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% in comparison to a cell that does not contain the construct.

Any polynucleotide of the present invention, be it a "desired polynucleotide," a "first" polynucleotide, a "second" polynucleotide may share a certain percentage sequence identity with a target sequence. As explained herein, a target sequence may be, but is not limited to, a sequence, partial or full-length, of a gene, regulatory element, such as a promoter or terminator, exon, intron, an untranslated region, or any sequence upstream or downstream of a target genomic sequence. Accordingly, a polynucleotide of the present invention, may comprise a sequence that is identical over the length of that sequence to such a target sequence. On the other hand, the polynucleotide of the present invention, may comprise a sequence that shares sequence identity to such a target sequence. Hence, a desired polynucleotide of the present invention may share about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% nucleotide sequence identity with a sequence of the target sequence.

In another embodiment, a desired polynucleotide comprises a sequence that is derived from a target promoter. The target promoter may either be naturally present in a cell genome, that is, the target promoter is endogenous to the cell genome, or may be introduced into that genome through transformation. The derived promoter of the polynucleotide may be functionally active and contain a TATA box or TATA box-like sequence but neither the transcription start nor any transcribed sequences beyond the transcription start. Alternatively, the derived promoter of the polynucleotide may be functionally inactive by, for instance, the absence of a TATA box. Such a derived promoter may represent only part of the target promoter.

In another embodiment, the desired polynucleotide comprises a sequence that is specific to an intron that is endogenous to a cell genome.

In another embodiment, the desired polynucleotide comprises a sequence that is part of a terminator that is endogenous to a cell genome.

In another embodiment, the construct comprises two identical promoters that are functionally active in a target tissue. In another embodiment, the construct comprises two different promoters, each of which is functionally active in a target tissue.

A construct of the present invention may further comprise one or more additional polynucleotides between cassette A and cassette B. For instance, in the 5'- to 3'-orientation, a construct may comprise (i) a first promoter, (ii) a desired polynucleotide, (iii) an additional polynucleotide spacer, e.g., an intron, (iv) the inverse complement copy of the desired polynucleotide, and (v) a second promoter, where the first and second promoters are operably linked to the desired polynucleotide and the complementary copy, respectively, and are oriented to induce convergent transcription.

The additional spacer polynucleotide may be of any length. That is, the spacer polynucleotide may be an intron that is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 300, 400, 500, or more than 500 nucleotides, or any integer in between in length. If the spacer polynucleotide between two desired polynucleotides is long enough, transcription may never proceed from promoter to the other. That is, for whatever reason, transcription may stop whilst the transcription machinery is located in the spacer that does not contain a functionally active terminator element. Accordingly, the resultant transcript may comprise the full-length sequence of a first desired polynucleotide and a partial sequence of the intron, but no part of the second desired polynucleotide. Thus, it may be possible to design a construct as described herein with a spacer polynucleotide that prevents transcription from proceeding from one desired polynucleotide to the other. In such a situation, and if one of the desired polynucleotides is oriented as the inverse complementary copy of the other, then the prevention of transcription read-through would, therefore, avoid the synthesis of an RNA transcript that is self-complementary.

Accordingly, depending on any of (i) the convergent arrangement of promoters and desired polynucleotides, (ii) the copy number of the desired polynucleotides, (iii) the absence of a terminator region from the construct, and (iv) the complementarity and length of the resultant transcripts, various populations of RNA molecules may be produced from the present constructs.

Hence, a single construct of the present invention may produce (i) a single stranded "sense" RNA transcript, (ii) a single-stranded "antisense" RNA transcript, (iii) a hairpin duplex formed by a single-stranded RNA transcript that anneals to itself, or (iv) an RNA duplex formed from two distinct RNA transcripts that anneal to each other. A single construct may be designed to produce only sense or only antisense RNA transcripts from each convergently-arranged promoter.

The present invention also provides a method of reducing expression of a gene normally capable of being expressed in a plant cell, by stably incorporating any of the constructs described herein into the genome of a cell.

In this regard, any type of cell from any species may be exposed to or stably- or transiently-transformed with a construct of the present invention. Hence, a bacterial cell, viral cell, fungal cell, algae cell, worm cell, plant cell, insect cell, reptile cell, bird cell, fish cell, or mammalian cell may be transformed with a construct of the present invention. The target sequence, therefore, may be located in the nucleus or a genome of any on of such cell types. The target sequence, therefore, may be located in a gene in the cell genome. Hence, the target sequence may be located in at least one of a regulatory element of the gene, an exon of the gene, an intron of the gene, the 5'-untranslated region of the gene, or the 3'-untranslated region of the gene. In one embodiment, the regulatory element of the gene is at least one of the promoter or an enhancer element of the gene.

Alternatively, the target sequence may be located in an RNA transcript that is present in one of these cells and which may or may not be normally produced by the cell. That is, the RNA transcript that comprises the target sequence may be produced from a source that is foreign to the host cell. For instance, the RNA transcript that comprises the target sequence may be of viral origin but exists in a plant cell.

The present invention also contemplates in vitro, ex vivo, ex planta and in vivo exposure and integration of the desired construct into a cell genome or isolated nucleic acid preparations.

The constructs of the present invention, for example, may be inserted into Agrobacterium-derived transformation plasmids that contain requisite T-DNA border elements for transforming plant cells. Accordingly, a culture of plant cells may be transformed with such a transformation construct and, successfully transformed cells, grown into a desired transgenic plant that expresses the convergently operating promoter/polynucleotide cassettes.

The promoters may be constitutive or inducible promoters or permutations thereof. "Strong" promoters, for instance, can be those isolated from viruses, such as rice tungro baciliform virus, maize streak virus, cassaya vein virus, mirabilis virus, peanut chlorotic streak caulimovirus, figwort mosaic virus and chlorella virus. Other promoters can be cloned from bacterial species such as the promoters of the nopaline synthase and octopine synthase gene. There are various inducible promoters, but typically an inducible promoter can be a temperature-sensitive promoter, a chemically-induced promoter, or a temporal promoter. Specifically, an inducible promoter can be a Ha hsp17.7 G4 promoter, a wheat wcs120 promoter, a Rab 16A gene promoter, an α-amylase gene promoter, a pin2 gene promoter, or a carboxylase promoter.

Another aspect of the present invention is a construct, comprising an expression cassette which comprises (i) a first promoter operably linked to a first polynucleotide and (ii) a second promoter operably linked to a second polynucleotide, wherein (a) neither the first nor the second polynucleotide is operably linked to a terminator, (b) at least part of the second polynucleotide is substantially identical in nucleotide sequence to at least part of the sequence of the first polynucleotide but is positioned within the cassette in a different orientation to the first polynucleotide, and (c) the direction of transcription initiated from the first promoter is toward the second promoter and the direction of transcription initiated from the second promoter is toward the first promoter.

In one embodiment, at least part of the second polynucleotide is oriented as an inverse complement copy of at least part of the first polynucleotide.

In another embodiment, the sequence that terminates transcription, to which neither polynucleotide is operably linked, is a sequence at the 3'-end of a gene that is involved in 3'-end formation and polyadenylation of the transcript of that gene.

In a preferred embodiment, the sequence that is involved in 3-end formation and polyadenylation is a terminator.

In another embodiment, the expression cassette does not comprise (i) a nos gene terminator, (ii) the 3' untranslated sequence of T-DNA gene 7, (iii) the 3' untranslated sequences of the major inclusion body protein gene of cauliflower mosaic virus, (iv) the 3' untranslated sequences of the pea ribulose 1,5-bisphosphate carboxylase small subunit, (v) the 3' untranslated sequences of the potato ubiquitin-3 gene, or (vi) the 3' untranslated sequences of the potato proteinase inhibitor II gene, (vii) the 3' untranslated sequences of opine genes, (viii) the 3' untranslated sequences of endogenous genes.

In one embodiment, the first polynucleotide comprises a sequence that shares sequence identity with a target gene or at least one of a regulatory element that is associated with the target gene, an exon of the target gene, an intron of the target gene, the 5'-untranslated region of the target gene, or the 3'-untranslated region of the target gene.

In another embodiment, the first polynucleotide comprises a sequence that shares about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 8%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% nucleotide sequence identity with a sequence of the target sequence.

In one embodiment, the target gene is a COMT gene involved in lignin biosynthesis, a CCOMT gene involved in lignin biosynthesis, any other gene involved in lignin biosynthesis, an R1 gene involved in starch phosphorylation, a phosphorylase gene involved in starch phosphorylation, a PPO gene involved in oxidation of polyphenols, a polygalacturonase gene involved in pectin degradation, a gene involved in the production of allergens, a gene involved in fatty acid biosynthesis such as FAD2.

In another embodiment, (a) the regulatory element of the target gene is the promoter or an enhancer element associated with the target gene or (b) the first polynucleotide comprises a sequence that shares sequence identity with an intron of a target gene, wherein the intron comprises the sequence of SEQ ID NO: 44.

In a particular embodiment, the target gene is located in the genome of a cell. Hence, the cell may be a cell from a bacteria, virus, fungus, yeast, plant, reptile, bird, fish, or mammal.

In one embodiment, the target sequence is located in a DNA sequence that encodes an RNA transcript.

In another embodiment, the first and second promoters are functional in a plant.

In a preferred embodiment, the expression cassette is located between transfer-DNA border sequences of a plasmid that is suitable for bacterium-mediated plant transformation.

In yet another embodiment, the bacterium is *Agrobacterium, Rhizobium*, or *Phyllobacterium*. In one embodiment, the bacterium is *Agrobacterium tumefaciens, Rhizobium trifolii, Rhizobium leguminosarum, Phyllobacterium myrsinacearum, SinoRhizobium meliloti*, and *MesoRhizobium loti*.

In one embodiment, the construct further comprises a spacer polynucleotide positioned between the first and second polynucleotides. The spacer polynucleotide may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 300, 400, 500, or more than 500 nucleotides long.

In another embodiment, the first promoter is a near-constitutive promoter, a tissue-specific promoter, or an inducible promoter and wherein the second promoter is a near-constitutive promoter, a tissue-specific promoter, or an inducible promoter.

In a particular embodiment, the constitutive strong promoter is selected from the group consisting of a potato ubiquitin-7 promoter, a potato ubiquitin-3 promoter, a tomato ubiquitin promoter, an alfalfa petE promoter, an alfalfa Pal promoter, a canola napin promoter, a maize ubiquitin promoter, a rice ubiquitin promoter, a sugarcane ubiquitin promoter, a rice actin promoter, a rubisco small subunit promoter, and a rubisco activase promoter.

In one embodiment, the tissue-specific promoter is a granule-bound starch synthase promoter or an ADP glucose pyrophosphorylase gene promoter.

In one embodiment, the inducible promoter is a temperature-sensitive promoter, a chemically-induced promoter, or a temporal promoter.

In one embodiment, the inducible promoter is selected from the group consisting of an Ha hsp17.7 G4 promoter, a wheat wcs120 promoter, a Rab 16A gene promoter, an α-amylase gene promoter, a pin2 gene promoter, and a carboxylase promoter.

Another aspect of the present invention is a transformation plasmid, comprising an expression cassette, which comprises in the 5' to 3' orientation (1) a first promoter that is operably linked to (2) a first desired polynucleotide, which abuts (3) at least one optional spacer polynucleotide, where the 3'-end of one of the spacer polynucleotides abuts a (4) a second desired polynucleotide, which is operably linked to (5) a second promoter, wherein neither desired polynucleotide in the expression cassette is operably linked to any known transcription terminator.

In one embodiment, at least part of the first desired polynucleotide is in the antisense orientation and wherein at least part of the second desired polynucleotide is oriented as the inverse complement of the first desired polynucleotide.

In another embodiment, at least part of the first desired polynucleotide is in the sense orientation and wherein at least part of the second desired polynucleotide is oriented as the inverse complement of the first desired polynucleotide.

In another embodiment, at least part of the first desired polynucleotide is a promoter sequence.

In a further embodiment, the promoter sequence is from a promoter selected from the group consisting of (1) a starch-associated R1 gene promoter, (2) a polyphenol oxidase gene promoter, (3) a fatty acid desaturase 12 gene promoter, (4) a microsomal omega-6 fatty acid desaturase gene promoter, (5) a cotton stearoyl-acyl-carrier protein delta 9-desaturase gene promoter, (6) an oleoyl-phosphatidylcholine omega 6-desaturase gene promoter, (7) a *Medicago truncatula* caffeic acid/5-hydroxyferulic acid 3/5-O-methyltransferase (COMT) gene promoter, (8) a *Medicago sativa* (alfalfa) caffeic acid/5-hydroxyferulic acid 3/5-O-methyltransferase (COMT) gene promoter, (9) a *Medicago truncatula* caffeoyl CoA 3-O-methyltransferase (CCOMT) gene promoter, (10) a *Medicago sativa* (alfalfa) caffeoyl CoA 3-O-methyltransferase (CCOMT) gene promoter, (11) a major apple allergen Mal d 1 gene promoter, (12) a major peanut allergen Ara h 2 gene promoter, (13) a major soybean allergen Gly m Bd 30 K gene promoter, and (14) a polygalacturonase gene promoter.

In one embodiment, (i) at least one of the first and second promoters is a GBSS promoter, and (ii) the first desired polynucleotide is a sequence from a polyphenol oxidase gene.

In another embodiment, the first and second promoters are GBSS promoters.

In one embodiment, both the first promoter is a GBSS promoter and the second promoter is an AGP promoter.

Another aspect of the present invention is a method of reducing expression of a gene normally capable of being expressed in a plant cell, comprising exposing a plant cell to any construct described herein, wherein the construct is maintained in a bacterium strain, wherein the desired polynucleotide comprises a sequence that shares sequence identity to a target sequence in the plant cell genome.

In one embodiment, the bacterium strain is *Agrobacterium tumefaciens, Rhizobium trifolii, Rhizobium leguminosarum, Phyllobacterium myrsinacearum, SinoRhizobium meliloti,* and *MesoRhizobium loti*.

Another aspect of the present invention is a construct, comprising an expression cassette which comprises in the 5' to 3' orientation (i) a first promoter, (ii) a first polynucleotide that comprises a sequence that shares sequence identity with at least a part of a promoter sequence of a target gene, (iii) a second polynucleotide comprising a sequence that shares sequence identity with the inverse complement of at least part of the promoter of the target gene, and (iv) a second promoter, wherein the first promoter is operably linked to the 5'-end of the first polynucleotide and the second promoter is operably linked to the 3'-end of the second polynucleotide.

Another aspect of the present invention is a construct, comprising an expression cassette which comprises in the 5' to 3' orientation (i) a first promoter, (ii) a first polynucleotide that comprises a sequence that shares sequence identity with at least a part of a promoter sequence of a target gene, (iii) a second polynucleotide comprising a sequence that shares sequence identity with the inverse complement of at least part of the promoter of the target gene, (iv) a terminator, wherein the first promoter is operably linked to the 5'-end of the first polynucleotide and the second polynucleotide is operably linked to the terminator.

Another aspect of the present invention is a plant transformation plasmid, comprising the sequence depicted in SEQ ID NO: 40 or 42.

Another aspect of the present invention is a method for reducing cold-induced sweetening in a tuber, comprising expressing any construct described herein in a cell of a tuber, wherein (a) the first polynucleotide comprises the sequence of part of an R1 gene, (b) the second polynucleotide is the inverse complement of the first polynucleotide compared to the first polynucleotide, (c) one or both of the first and second promoters are GBSS or AGP, and (d) expression of the construct in the cell reduces transcription and/or translation of an R1 gene in the tuber cell genome, thereby reducing cold-induced sweetening in the tuber. In one embodiment, the first polynucleotide comprises the sequence depicted in SEQ ID NO: 23 or 24. In another embodiment, the tuber is a potato. In another embodiment, the first polynucleotide comprises two copies of the sequence of SEQ ID NO: 23 or 24.

Another aspect of the present invention is a method for enhancing tolerance to black spot bruising in a tuber, comprising expressing any construct described herein in a cell of a tuber, wherein (a) the first polynucleotide comprises the sequence of part of a polyphenol oxidase gene, (b) the second polynucleotide is the inverse complement of the first polynucleotide, (c) one or both of the first and second promoters are GBSS or AGP, and (d) expression of the construct in the cell reduces transcription and/or translation of a polyphenol oxidase gene in the tuber cell genome, thereby enhancing the tolerance of the tuber to black spot bruising. In one embodiment, the first polynucleotide comprises the sequence of SEQ ID NO: 26 or 27. In another embodiment, the tuber is a potato. In another embodiment, the first polynucleotide comprises two copies of the sequence of SEQ ID NO: 26 or 27.

Another aspect of the present invention is a method for increasing oleic acid levels in an oil-bearing plant, comprising expressing any construct described herein in a cell of a seed of an oil-bearing plant, wherein (a) the first polynucleotide comprises the sequence of part of a Fad2 gene, (b) the second polynucleotide is the inverse complement of the first polynucleotide, (c) one or both of the first and second promoters are napin gene, Fad2 gene, or stearoyl-ACP desaturase gene promoters, and (d) expression of the construct in the cell reduces transcription and/or translation of a Fad2 gene in the cell of the seed of the oil-bearing plant, thereby increasing the oil content of the seed. In one embodiment, the first polynucleotide comprises the sequence depicted in SEQ ID NO: 28. In another embodiment, the sequence of the napin gene promoter comprises the sequence depicted in SEQ ID NO: 30.

In one embodiment, the sequence of the stearoyl-ACP desaturase gene promoter comprises the sequence depicted in SEQ ID NO: 31.

In another embodiment, the sequence of the Fad2 gene promoter comprises the sequence depicted in SEQ ID NO: 32.

In one embodiment, the oil-bearing plant is a Brassica plant, canola plant, soybean plant, cotton plant, or a sunflower plant.

Another aspect of the present invention is a method for reducing lignin content in a plant, comprising expressing any construct described herein in a cell of the plant, wherein (a) the first polynucleotide comprises the sequence of part of a caffeic acid/5-hydroxyferulic acid 3/5-O-methyltransferase (COMT) gene, (b) the second polynucleotide is the inverse complement of the first polynucleotide, (c) one or both of the first and second promoters are petE or Pal gene promoters, and (d) expression of the construct in the cell reduces transcription and/or translation of a COMT gene in the cell of the plant, thereby reducing lignin content in a plant. In one embodiment, the cell is in the vascular system of the plant. In a preferred embodiment, the plant is an alfalfa plant. In another embodiment, the first polynucleotide comprises the sequence depicted in SEQ ID NO: 33 or 37.

Another aspect of the present invention is a method for reducing the degradation of pectin in a fruit of a plant, comprising expressing any construct described herein in a fruit cell of the plant, wherein (a) the first polynucleotide comprises the sequence of part of polygalacturonase gene, (b) the second polynucleotide is the inverse complement of the first polynucleotide, (c) both of the first and second promoters are fruit-specific promoters, and (d) expression of the construct in the fruit cell reduces transcription and/or translation of a polygalacturonase gene in the cell of the plant, thereby reducing the degradation of pectin in the fruit. In one embodiment, the first polynucleotide comprises the sequence depicted in SEQ ID NO: 39.

Another aspect of the present invention is a method for reducing the allergenicity of a food produced by a plant, comprising expressing any construct described herein in a cell of a plant, wherein (a) the first polynucleotide comprises the sequence of part of a gene that encodes an allergen, (b) the second polynucleotide is the inverse complement of the first polynucleotide, and (c) the expression of the construct reduces transcription and/or translation of the allergen, thereby reducing the allergenicity of a food produced by the plant.

In one embodiment, (a) the plant is an apple plant, (b) the food is an apple, (c) the first polynucleotide comprises a sequence from the Mal d I gene promoter, and (d) expression of the construct in the apple plant reduces transcription and/or translation of Mal d I in the apple.

In another embodiment, (a) the plant is a peanut plant, (b) the food is a peanut, (c) the first polynucleotide comprises a sequence from the Ara h 2 gene promoter, and (d) expression of the construct in the peanut plant reduces transcription and/or translation of Ara h 2 in the peanut.

In another embodiment, (a) the plant is a soybean plant, (b) the food is a soybean, (c) the first polynucleotide comprises a sequence from the Gly m Bd gene promoter, and (d) expression of the construct in the soybean plant reduces transcription and/or translation of Gly m Bd in the soybean.

Another aspect of the present invention is a method for downregulating the expression of multiple genes in a plant, comprising expressing in a cell of a plant a construct comprising the sequence depicted in SEQ ID NO: 40, which downregulates expression of polyphenol oxidase, phosphorylase L gene, and the R1 gene in the plant cell.

Another aspect of the present invention is a method for downregulating the expression of multiple genes in a plant, comprising expressing in a cell of a plant a construct comprising the sequence depicted in SEQ ID NO: 42, which downregulates expression of polyphenol oxidase, phosphorylase L gene, and the R1 gene in the plant cell.

Another aspect of the present invention is a construct, comprising a desired promoter that is operably linked to (i) a first promoter at its 5'-end and (ii) a second promoter at its 3'-end, wherein the desired promoter shares sequence identity with a target promoter in a genome of interest.

Another aspect of the present invention is a construct, comprising a two convergently-oriented copies of a desired promoter that are separated by a polynucleotide, wherein the desired promoter shares sequence identity with a target promoter in a desired genome of interest. In one embodiment, the polynucleotide that separates the convergently-oriented promoters is an intron.

Another aspect of the present invention is a construct, comprising two desired promoters that are operably linked to a promoter and a terminator, wherein the desired promoters share sequence identity with a target promoter in a genome of interest. In one embodiment, the two desired promoters share, over at least a part of their respective lengths, sequence identity with each other and where one of the desired promoters is oriented as the inverse complement of the other.

In another aspect is a construct, comprising two desired promoters that are operably linked to a promoter and a terminator, wherein the desired promoters share sequence identity with a target promoter in a genome of interest. In one embodiment, the two desired promoters share, over at least a part of their respective lengths, sequence identity with each other and where one of the desired promoters is oriented as the inverse complement of the other.

In another aspect a construct is provided that comprises four direct repeats of a polynucleotide of interest, which are preceded by an antisense DNA fragment of the polynucleotide of interest. Such a construct is depicted by pSIM1111.

The present invention also provides a method for reducing the expression level of an endogenous gene in an alfalfa plant, comprising introducing a cassette into an alfalfa cell, wherein the cassette comprises two alfalfa-specific promoters arranged in a convergent orientation to each other, wherein the activity of the promoters in the cassette reduces the expression level of an endogenous alfalfa gene, which is operably linked in the alfalfa genome to a promoter that has a sequence that shares sequence identity with at least a part of one of the promoters in the cassette. In one embodiment, the sequence of at least one of the promoters is depicted in SEQ ID NO: 54 or SEQ ID NO: 55.

The present invention also provides a method for reducing the expression of a Comt gene, comprising expressing a Comt gene fragment or Comt promoter fragment in a cell that comprises a Comt gene in its genome.

The present invention also provides a method for reducing the expression of a Comt gene or Ccomt gene, comprising expressing the construct of any construct described herein in a cell that comprises a Comt gene or a Ccomt gene in its genome, wherein the first polynucleotide comprises a sequence of a Comt gene or Comt gene promoter or a Ccomt gene or Ccomt gene promoter.

BRIEF DESCRIPTION OF THE DRAWINGS

FIG. 9 shows a sequence analysis of the various promoter fragments and identifies a 89-bp sequence that may be methylated during promoter-based silencing.

DETAILED DESCRIPTION OF THE PREFERRED EMBODIMENTS

Figure 1:
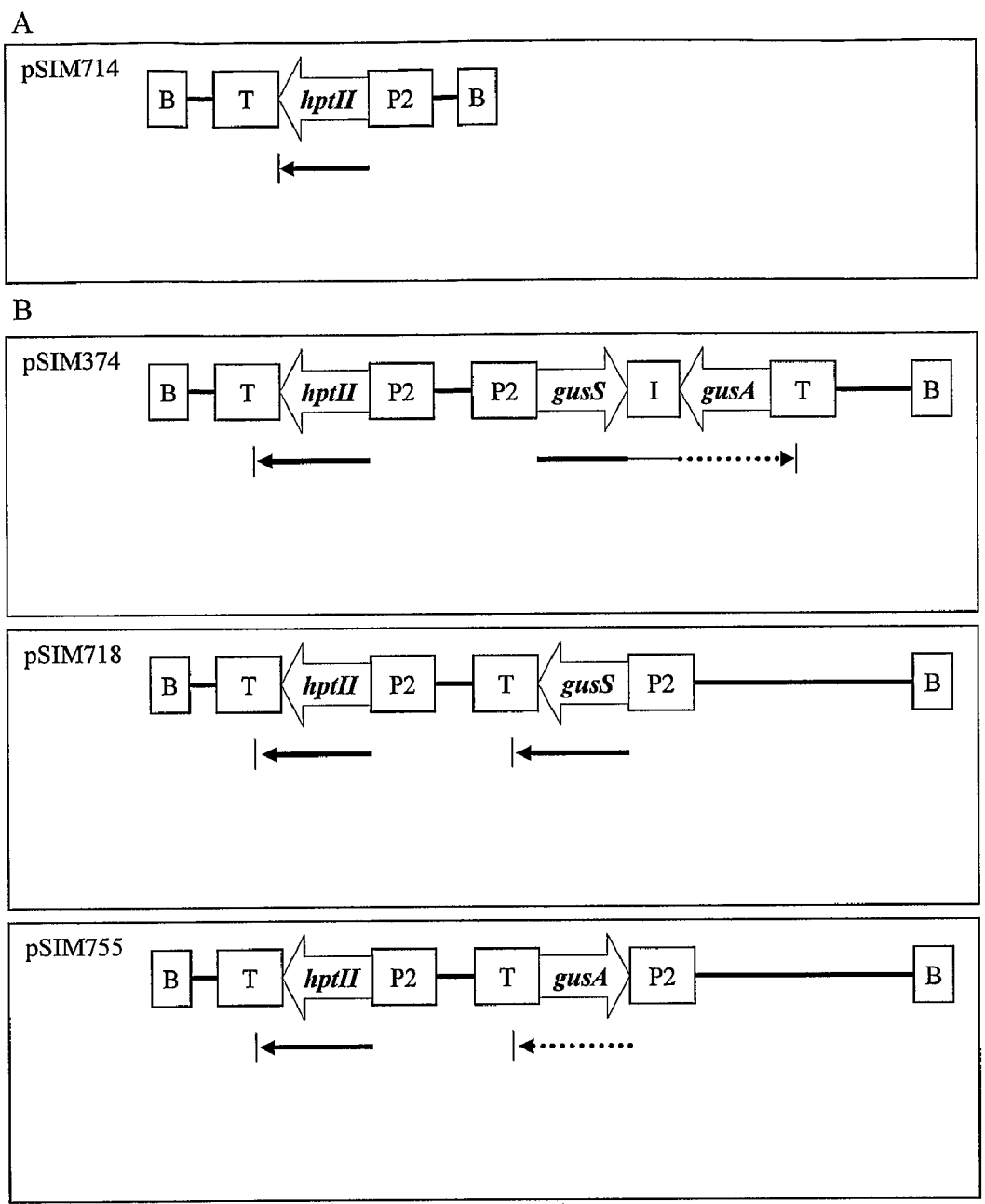
FIG. 1 depicts schematic diagrams for T-DNAs of binary vectors that (a) represent a negative control (pSIM714), and (b) comprise constructs that represent conventional silencing constructs, pSIM374, pSIM718, and pSIM755. "B" denotes a transfer-DNA border sequence; "T" denotes a terminator sequence; "hptII" is a resistance gene that confers hygromycin resistance to a plant; "P1" denotes a promoter sequence and, in this example, is a promoter that is identical to the promoter driving a functionally active bete-glucuronidase (gus) gene in the transgenic gus plant; "P2" denotes a promoter sequence that is also functionally active but different from P1; "gus-S" denotes a gus gene fragment; "gus-A" denotes an inverse complement of the gus gene fragment; "I" denotes an intron. With respect to gus-S and gus-A, the solid thick arrows signify (part of the) RNA transcripts that share identity with a part of the transcript produced by expressing the gus gene; the dotted thick arrows signify (part of the) RNA transcripts that share identity with a part of the inverse complement of the gus gene transcript; the thin lines signify parts of the transcript with homology or inverse complementarity to another sequence such as the intron of the construct. In this respect, the leftward pointing open arrow (which denotes the "gus-A" element in the cassette) indicates that the gus-A element is oriented in the expression cassette as the inverse complement of the gus-S, the rightward pointing arrow. Hence, P1 and P2 promoters are oriented so that transcription from each proceeds in a convergent manner, i.e., transcription of P1 proceeds toward P2 and vice versa.
Figure 2:
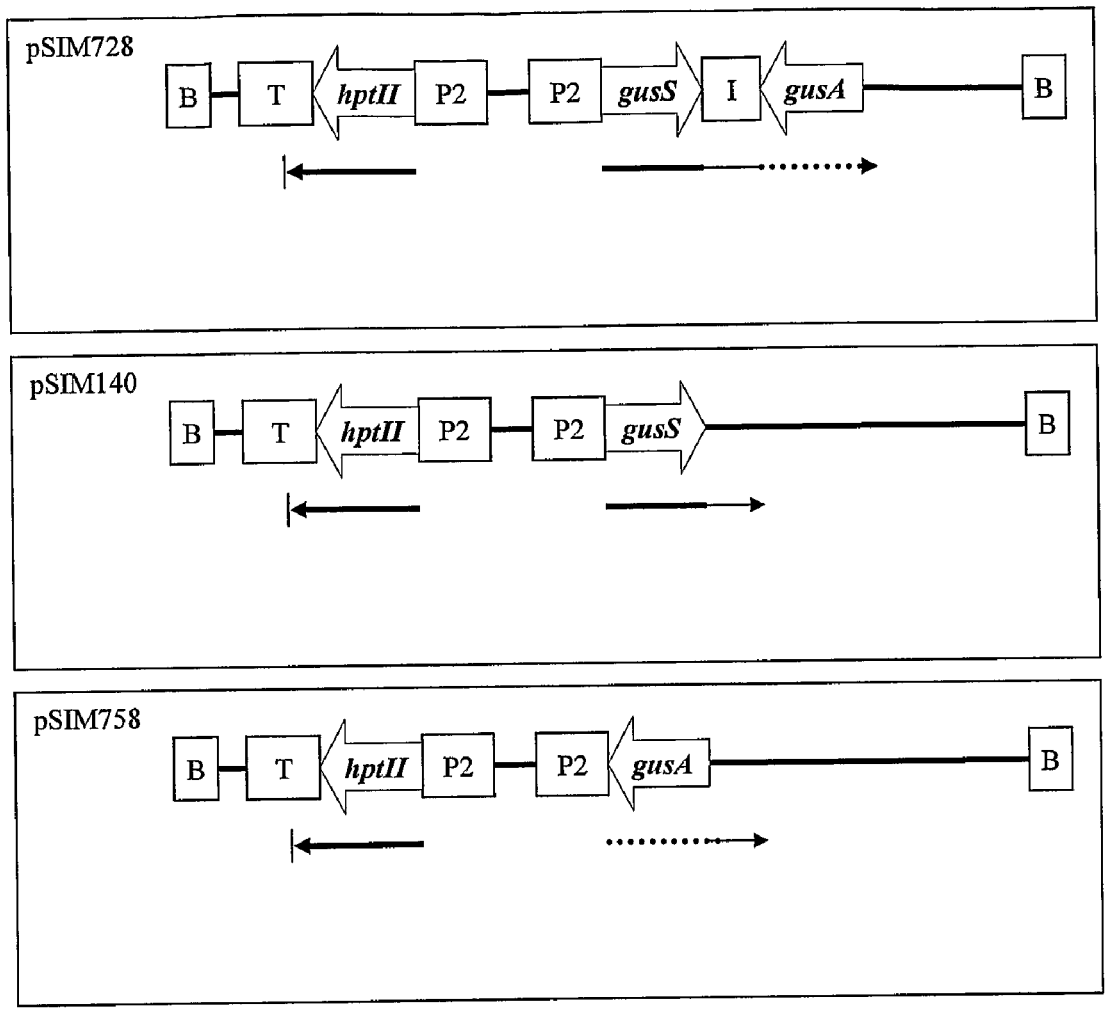
FIG. 2 depicts schematic diagrams for T-DNAs of binary vectors comprising constructs that resemble conventional silencing constructs except that they lack a terminator, pSIM728, pSIM140, and pSIM758. With respect to gus-S and gus-A, the solid thick arrows signify the part of the RNA transcripts that share identity with a part of the transcript produced by expressing the gus gene; the dotted thick arrows signify parts of the RNA transcripts that share identity with a part of the inverse complement of the gus gene transcript; the thin lines signify parts of the transcript with homology or inverse complementarity to another sequence such as the intron of the construct.

A construct of the present invention can be used to efficiently reduce or prevent the transcription or translation of a target nucleic acid by triggering convergent transcription of a desired polynucleotide. Hence one goal of the present invention is to provide constructs that produce nucleic acid molecules that prevent or reduce expression of a gene or of a gene product, such as an RNA transcript or protein.

One particular characteristic of such a construct is that, in contrast to conventional silencing constructs, no functional terminator is inserted and operably linked to the 3'-end of a desired polynucleotide. It is well established that a terminator is a nucleotide sequence, typically located at the 3'-end of a gene, that is involved in cleavage of the RNA transcript that is transcribed from the gene and in polyadenylation of that transcript. Typically, a terminator is located downstream of the gene's stop codon.

Terminators that were used for the construction of conventional silencing cassettes, and which are excluded from constructs of the present invention, were derived from such 3'-regions of certain genes and often also included even more downstream non-transcribed DNA sequences. The choice of which terminator to use has more often than not, simply been a matter of convenience. Hence, opine terminators or termination regions from endogenous and previously characterized genes have been used in conventional silencing constructs. One of the more frequently used terminators, for instance, is the *Agrobacterium* nopaline synthase (nos) gene terminator, which comprises both 3' untranslated sequences and some additional downstream DNA. Other terminators include:

The 3' untranslated sequences of T-DNA gene 7 (Genbank accession V00090).

The 3' untranslated sequences of the major inclusion body protein gene of cauliflower mosaic virus.

The 3' untranslated sequences of the pea ribulose 1,5-bisphosphate carboxylase small subunit (Genbank accession M21375).

The 3' untranslated sequences of the potato ubiquitin-3 gene (Genbank accession Z11669).

The 3' untranslated sequences of the potato proteinase inhibitor II gene (Genbank accession CQ889094).

The 3' untranslated sequences of opine genes.

The 3' untranslated sequences of endogenous genes; that is genes that are normally expressed by the genome of an organism.

With respect to the present invention, however, none of such terminators, indeed, no functional terminator, is directly operably linked to a desired polynucleotide of the present construct. Nor is a desired polynucleotide directly operably linked to a terminator that is preceded by a self-splicing ribozyme-encoding sequence.

Another characteristic of the construct of the present invention is that it promotes convergent transcription of one or more copies of polynucleotide that is or are not directly operably linked to a terminator, via two opposing promoters. Due to the absence of a termination signal, the length of the pool of RNA molecules that is transcribed from the first and second promoters may be of various lengths.

Occasionally, for instance, the transcriptional machinery may continue to transcribe past the last nucleotide that signifies the "end" of the desired polynucleotide sequence. Accordingly, in this particular arrangement, transcription termination may occur either through the weak and unintended action of downstream sequences that, for instance, promote hairpin formation or through the action of unintended transcriptional terminators located in plant DNA flanking the transfer DNA integration site.

A terminator-free colliding transcription (TFCT) construct of the present invention, therefore, may comprise a first promoter operably linked to a first polynucleotide and a second promoter operably linked to a second polynucleotide, whereby (1) the first and second polynucleotides share at least some sequence identity with each other and a target sequence, and (2) the first promoter is oriented such that the direction of transcription initiated by this promoter proceeds towards the second promoter, and vice versa, (3) the construct produces RNA molecules that are generally different in size, some transcripts representing the RNA counterparts of at least part of the polynucleotide and others comprising the counterparts of at least some of both the polynucleotide and its inverse complement.

Figure 3:
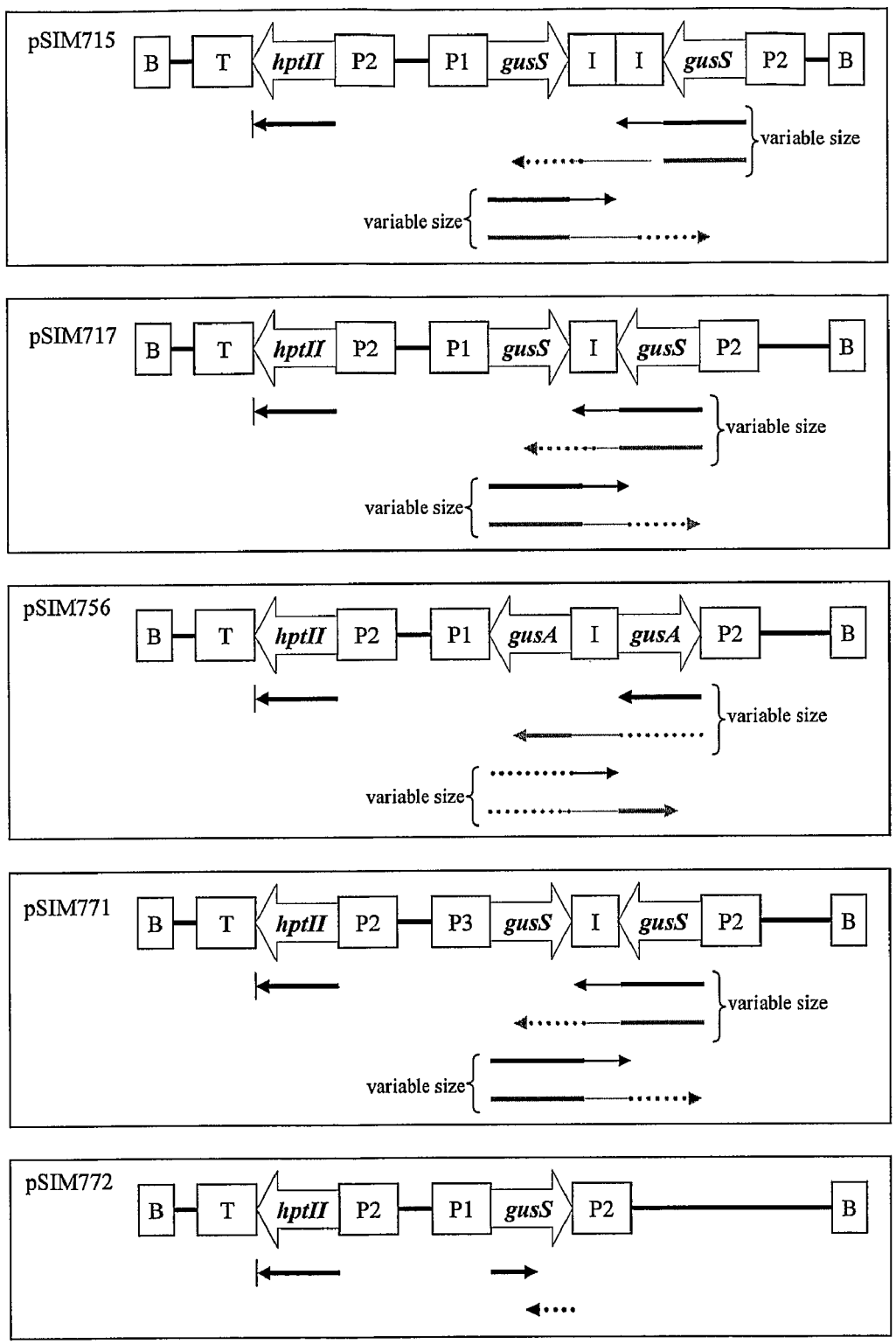
FIG. 3 depicts schematic diagrams for T-DNAs comprising "terminator-free colliding transcription" (TFCT) constructs. Specifically, it illustrates the T-DNAs of pSIM715, pSIM717, pSIM756, and pSIM771. The key to the identified elements and solid and dotted arrows is the same as those explained in the legend of FIG. 1. In pSIM717, read-through of transcription originated from both P1 and P2 over the intron produces transcripts that contain 5'-sequences identical to part of the gus gene transcript and 3'-sequences that are inverse complementary to the gus gene transcript. These transcripts may fold to produce partially double-stranded RNA. Depending on the ability of the P1 transcription complex to proceed unencumbered, an RNA transcript, initiated from the P1 promoter, could conceivably transcribe sequences downstream of the gus-S sequence to which it is operably linked. Accordingly, when reading the "top," i.e., sense strand of pSIM717, in a 5'- to 3'-direction, a transcript from P1 may comprise the sequence of the intervening intron ("I"), as well as the sequence of the inverse complement gus-S element. The "top" strand sequence of the inverse complement gus-S element is the antisense of gus-S.
Figure 3:
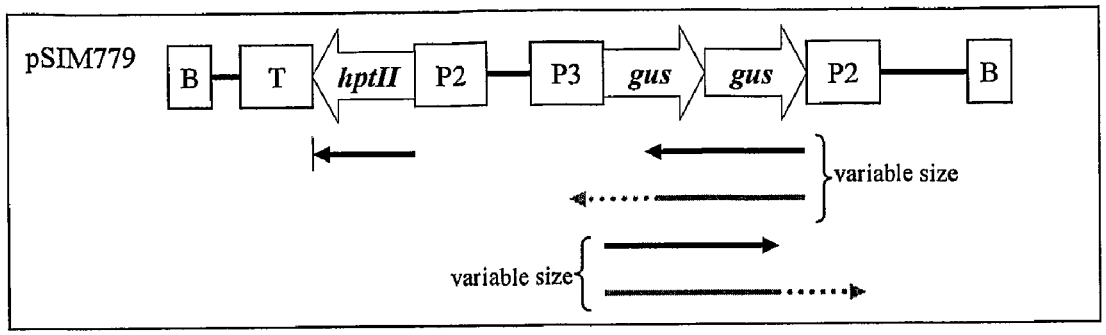
Figure 3:
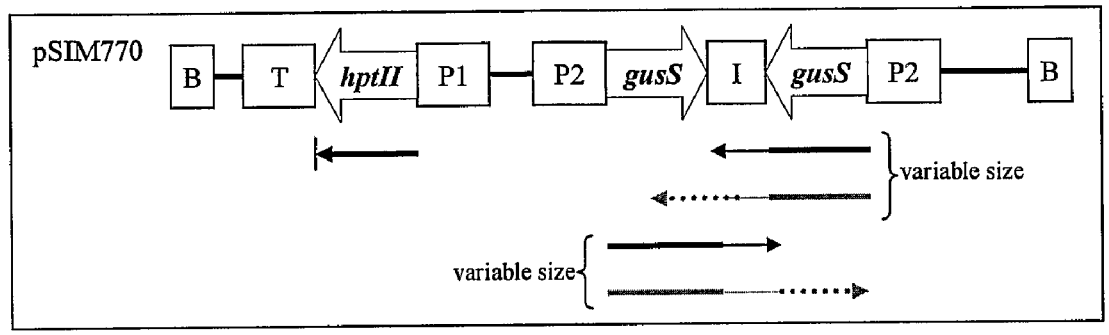
Figure 4:
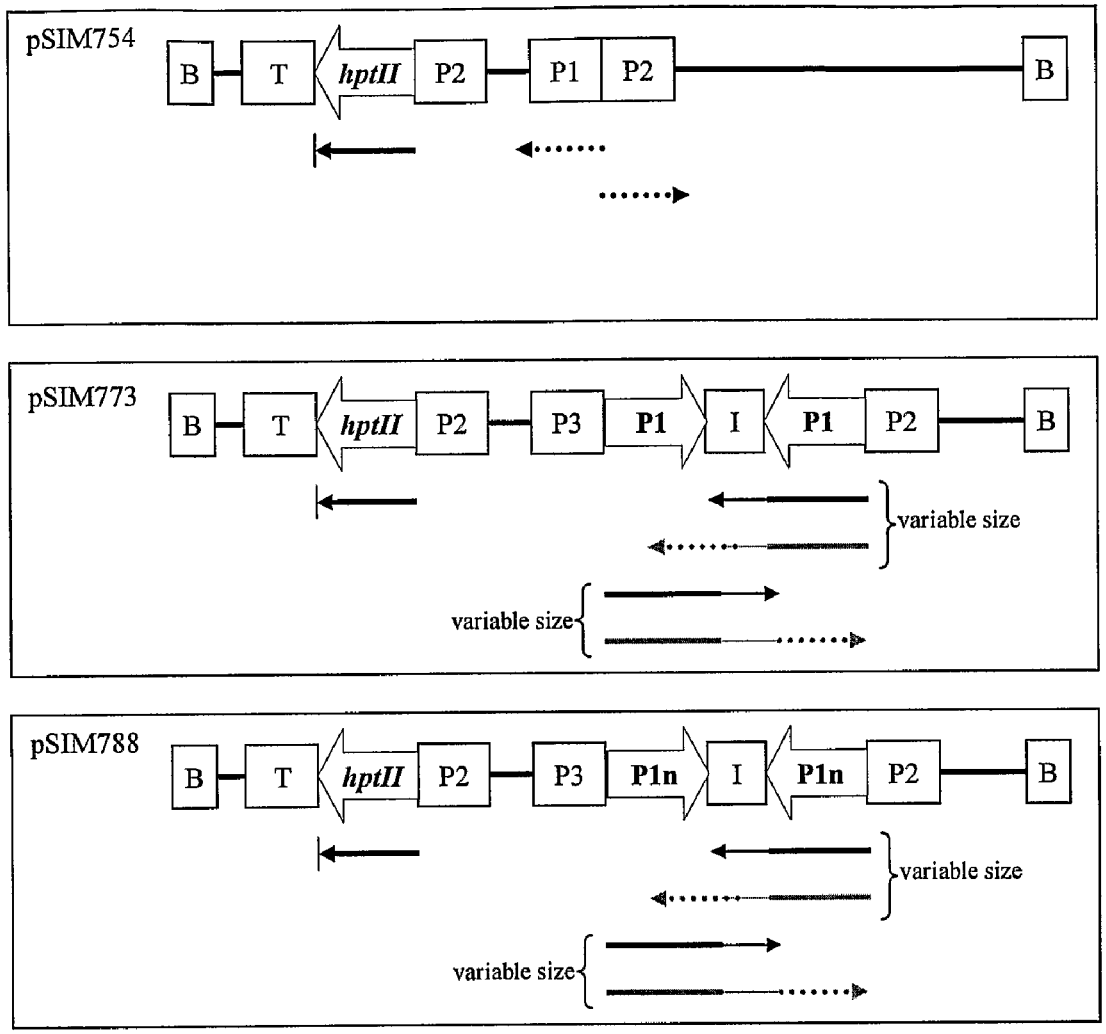
FIG. 4 depicts schematic diagrams for T-DNAs comprising "terminator-free colliding transcription" (TFCT) constructs. Specifically, it illustrates the T-DNAs of pSIM754, pSIM773, and pSIM767. The key to the identified elements and solid and dotted arrows is the same as those explained in the legend of FIG. 1. P1n indicates the part of the P1 promoter that is upstream from the TATA box. This sequence is not functional as promoter.

The desired polynucleotide may be linked in two different orientations to the promoter. In one orientation, e.g., "sense", at least the 5'-part of the resultant RNA transcript will share sequence identity with at least part of at least one target transcript. An example of this arrangement is shown in FIG. 3 as pSIM717. In the other orientation designated as "antisense", at least the 5'-part of the predicted transcript will be identical or homologous to at least part of the inverse complement of at least one target transcript. An example of the latter arrangement is shown in FIG. 3 as pSIM756.

As used herein, "sequence identity" or "identity" in the context of two nucleic acid or polypeptide sequences includes reference to the residues in the two sequences which are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol Sci.*, 4: 11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403-410 (1990); and, Altschul et al., *Nucleic Acids Res.* 25:3389-3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Clayerie and States, *Comput. Chem.*, 17:191-201 (1993)) low-complexity filters can be employed alone or in combination.

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

Any or all of the elements and DNA sequences that are described herein may be endogenous to one or more plant genomes. Accordingly, in one particular embodiment of the present invention, all of the elements and DNA sequences, which are selected for the ultimate transfer cassette are endogenous to, or native to, the genome of the plant that is to be transformed. For instance, all of the sequences may come from a potato genome. Alternatively, one or more of the elements or DNA sequences may be endogenous to a plant genome that is not the same as the species of the plant to be transformed, but which function in any event in the host plant cell. Such plants include potato, tomato, and alfalfa plants. The present invention also encompasses use of one or more genetic elements from a plant that is interfertile with the plant that is to be transformed.

Public concerns were addressed through development of an all-native approach to making genetically engineered plants, as disclosed by Rommens et al. in WO2003/069980, US-2003-0221213, US-2004-0107455, and WO2005/004585, which are all incorporated herein by reference. Rommens et al. teach the identification and isolation of genetic elements from plants that can be used for bacterium-mediated plant transformation. Thus, Rommens teaches that a plant-derived transfer-DNA ("P-DNA"), for instance, can be isolated from a plant genome and used in place of an *Agrobacterium* T-DNA to genetically engineer plants.

In this regard, a "plant" of the present invention includes, but is not limited to angiosperms and gymnosperms such as potato, tomato, tobacco, avocado, alfalfa, lettuce, carrot, strawberry, sugarbeet, cassava, sweet potato, soybean, pea, bean, cucumber, grape, brassica, maize, turf grass, wheat, rice, barley, sorghum, oat, oak, eucalyptus, walnut, and palm. Thus, a plant may be a monocot or a dicot. "Plant" and "plant material," also encompasses plant cells, seed, plant progeny, propagule whether generated sexually or asexually, and descendents of any of these, such as cuttings or seed. "Plant material" may refer to plant cells, cell suspension cultures, callus, embryos, meristematic regions, callus tissue, leaves, roots, shoots, gametophytes, sporophytes, pollen, seeds, germinating seedlings, and microspores. Plants may be at various stages of maturity and may be grown in liquid or solid culture, or in soil or suitable media in pots, greenhouses or fields. Expression of an introduced leader, trailer or gene sequences in plants may be transient or permanent.

Thus, any one of such plants and plant materials may be transformed according to the present invention. In this regard, transformation of a plant is a process by which DNA is stably integrated into the genome of a plant cell. "Stably" refers to the permanent, or non-transient retention and/or expression of a polynucleotide in and by a cell genome. Thus, a stably integrated polynucleotide is one that is a fixture within a transformed cell genome and can be replicated and propagated through successive progeny of the cell or resultant transformed plant. Transformation may occur under natural or artificial conditions using various methods well known in the art. See, for instance, METHODS IN PLANT MOLECULAR BIOLOGY AND BIOTECHNOLOGY, Bernard R. Glick and John E. Thompson (eds), CRC Press, Inc., London (1993); Chilton, Scientific American, 248)(6), pp. 36-45, 1983; Bevan, Nucl. Acids. Res., 12, pp. 8711-8721, 1984; and Van Montague et al., Proc R Soc Lond B Biol Sci., 210(1180), pp. 351-65, 1980. Plants also may be transformed using "Refined Transformation" and "Precise Breeding" techniques. See, for instance, Rommens et al. in WO2003/069980, US-2003-0221213, US-2004-0107455, WO2005/004585, US-2004-0003434, US-2005-0034188, WO2005/002994, and WO2003/079765, which are all incorporated herein by reference.

One or more traits of a tuber-bearing plant of the present invention may be modified using the transformation sequences and elements described herein. A "tuber" is a thickened, usually underground, food-storing organ that lacks both a basal plate and tunic-like covering, which corms and bulbs have. Roots and shoots grow from growth buds, called "eyes," on the surface of the tuber. Some tubers, such as caladiums, diminish in size as the plants grow, and form new tubers at the eyes. Others, such as tuberous begonias, increase in size as they store nutrients during the growing season and develop new growth buds at the same time. Tubers may be shriveled and hard or slightly fleshy. They may be round, flat, odd-shaped, or rough. Examples of tubers include, but are not limited to ahipa, apio, arracacha, arrowhead, arrowroot, baddo, bitter casava, Brazilian arrowroot, cassaya, Chinese artichoke, Chinese water chestnut, coco, cocoyam, dasheen, eddo, elephant's ear, girasole, goo, Japanese artichoke, Japanese potato, Jerusalem artichoke, jicama, lilly root, ling gaw, mandioca, manioc, Mexican potato, Mexican yam bean, old cocoyam, potato, saa got, sato-imo, seegoo, sunchoke, sunroot, sweet casava, sweet potatoes, tanier, tannia, tannier, tapioca root, topinambour, water lily root, yam bean, yam, and yautia. Examples of potatoes include, but are not limited to Russet Potatoes, Round White Potatoes, Long White Potatoes, Round Red Potatoes, Yellow Flesh Potatoes, and Blue and Purple Potatoes.

Tubers may be classified as "microtubers," "minitubers," "near-mature" tubers, and "mature" tubers. Microtubers are tubers that are grown on tissue culture medium and are small in size. By "small" is meant about 0.1 cm-1 cm. A "minituber" is a tuber that is larger than a microtuber and is grown in soil. A "near-mature" tuber is derived from a plant that starts to senesce, and is about 9 weeks old if grown in a greenhouse. A "mature" tuber is one that is derived from a plant that has undergone senescence. A mature tuber is, for example, a tuber that is about 12 or more weeks old.

In this respect, a plant-derived transfer-DNA ("P-DNA") border sequence of the present invention is not identical in nucleotide sequence to any known bacterium-derived T-DNA border sequence, but it functions for essentially the same purpose. That is, the P-DNA can be used to transfer and integrate one polynucleotide into another. A P-DNA can be inserted into a tumor-inducing plasmid, such as a Ti-plasmid from *Agrobacterium* in place of a conventional T-DNA, and maintained in a bacterium strain, just like conventional transformation plasmids. The P-DNA can be manipulated so as to contain a desired polynucleotide, which is destined for integration into a plant genome via bacteria-mediated plant transformation. See Rommens et al. in WO2003/069980, US-2003-0221213, US-2004-0107455, and WO2005/004585, which are all incorporated herein by reference.

Thus, a P-DNA border sequence is different by 1, 2, 3, 4, 5, 6, 7, 8, 9, 10, 11, 12, 13, 14, 15, 16, 17, 18, 19, 20, or more nucleotides from a known T-DNA border sequence from an *Agrobacterium* species, such as *Agrobacterium tumefaciens* or *Agrobacterium* rhizogenes.

A P-DNA border sequence is not greater than 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51% or 50% similar in nucleotide sequence to an *Agrobacterium* T-DNA border sequence.

Methods were developed to identify and isolate transfer DNAs from plants, particularly potato and wheat, and made use of the border motif consensus described in US-2004-0107455, which is incorporated herein by reference.

In this respect, a plant-derived DNA of the present invention, such as any of the sequences, cleavage sites, regions, or elements disclosed herein is functional if it promotes the transfer and integration of a polynucleotide to which it is linked into another nucleic acid molecule, such as into a plant chromosome, at a transformation frequency of about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1%.

Any of such transformation-related sequences and elements can be modified or mutated to change transformation efficiency. Other polynucleotide sequences may be added to a transformation sequence of the present invention. For instance, it may be modified to possess 5'- and 3'-multiple cloning sites, or additional restriction sites. The sequence of a cleavage site as disclosed herein, for example, may be modified to increase the likelihood that backbone DNA from the accompanying vector is not integrated into a plant genome.

Any desired polynucleotide may be inserted between any cleavage or border sequences described herein. For example, a desired polynucleotide may be a wild-type or modified gene that is native to a plant species, or it may be a gene from a non-plant genome. For instance, when transforming a potato plant, an expression cassette can be made that comprises a potato-specific promoter that is operably linked to a desired potato gene or fragment thereof and a potato-specific terminator. The expression cassette may contain additional potato genetic elements such as a signal peptide sequence fused in frame to the 5'-end of the gene, and a potato transcriptional enhancer. The present invention is not limited to such an arrangement and a transformation cassette may be constructed such that the desired polynucleotide, while operably linked to a promoter, is not operably linked to a terminator sequence.

In addition to plant-derived elements, such elements can also be identified in, for instance, fungi and mammals. See, for instance, SEQ ID NOs: 173-182. Several of these species have already been shown to be accessible to *Agrobacterium*-mediated transformation. See Kunik et al., Proc Natl Acad Sci USA 98: 1871-1876, 2001, and Casas-Flores et al., Methods Mol Biol 267: 315-325, 2004, which are incorporated herein by reference.

When a transformation-related sequence or element, such as those described herein, are identified and isolated from a plant, and if that sequence or element is subsequently used to transform a plant of the same species, that sequence or element can be described as "native" to the plant genome.

Thus, a "native" genetic element refers to a nucleic acid that naturally exists in, originates from, or belongs to the genome of a plant that is to be transformed. In the same vein, the term "endogenous" also can be used to identify a particular nucleic acid, e.g., DNA or RNA, or a protein as "native" to a plant. Endogenous means an element that originates within the organism. Thus, any nucleic acid, gene, polynucleotide, DNA, RNA, mRNA, or cDNA molecule that is isolated either from the genome of a plant or plant species that is to be transformed or is isolated from a plant or species that is sexually compatible or interfertile with the plant species that is to be transformed, is "native" to, i.e., indigenous to, the plant species. In other words, a native genetic element represents all genetic material that is accessible to plant breeders for the improvement of plants through classical plant breeding. Any variants of a native nucleic acid also are considered "native" in accordance with the present invention. In this respect, a "native" nucleic acid may also be isolated from a plant or sexually compatible species thereof and modified or mutated so that the resultant variant is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% similar in nucleotide sequence to the unmodified, native nucleic acid isolated from a plant. A native nucleic acid variant may also be less than about 60%, less than about 55%, or less than about 50% similar in nucleotide sequence.

A "native" nucleic acid isolated from a plant may also encode a variant of the naturally occurring protein product transcribed and translated from that nucleic acid. Thus, a native nucleic acid may encode a protein that is greater than or equal to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60% similar in amino acid sequence to the unmodified, native protein expressed in the plant from which the nucleic acid was isolated.

In a terminator-free construct that so comprises two copies of the desired polynucleotide, one desired polynucleotide may be oriented so that its sequence is the inverse complement of the other. The schematic diagram of pSIM717 in FIG. 3 illustrates such an arrangement. That is, the "top," "upper," or "sense" strand of the construct would comprise, in the 5'- to 3'-direction, (1) a target gene fragment, and (2) the inverse complement of a target gene fragment. In this arrangement, a second promoter that is operably linked to that inverse complement of the desired polynucleotide will likely produce an RNA transcript that is at least partially identical in sequence to the transcript produced from the other desired polynucleotide.

The desired polynucleotide and its inverse complement may be separated by a spacer DNA sequence, such as an intron, that is of any length. It may be desirable, for instance, to reduce the chance of transcribing the inverse complement copy of the desired polynucleotide from the opposing promoter by inserting a long intron or other DNA sequence between the 3'-terminus of the desired polynucleotide and the 5'-terminus of its inverse complement. For example, in the case of pSIM717 (FIG. 3) the size of the intron ("I") may be lengthened so that the transcriptional complex of P1 is unlikely to reach the sequence of the inverse complement of gus-S before becoming interrupted or dislodged. Accordingly, there may be about 50, 100, 250, 500, 2000 or more than 2000 nucleotides positioned between the sense and antisense copies of the desired polynucleotide.

A desired polynucleotide of the present invention, e.g., a "first" or "second" polynucleotide as described herein may share sequence identity with all or at least part of a sequence of a structural gene or regulatory element. For instance, a first polynucleotide may share sequence identity with a coding or non-coding sequence of a target gene or with a portion of a promoter of the target gene. In one embodiment, the polynucleotide in question shares about 100%, 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 15%, or about 5% or at least about 1% sequence identity with a target gene or target regulatory element, such as a target promoter.

For ease, the term "desired polynucleotide" as used herein is not limiting but includes other terms used herein such as "first polynucleotide" and "second polynucleotide" or any polynucleotide that is used in a construct of the present invention to reduce expression of a target gene or sequence. Hence a "desired polynucleotide" may be a first or second polynucleotide or both.

In a simpler form, a construct of the present invention does not contain two copies of the polynucleotide but only one copy. Accordingly, the polynucleotide is operably linked to promoters at both its 5'- and 3' termini. In this particular arrangement, RNA transcripts will be produced that comprise sequences from each strand of the DNA duplex. An example of this arrangement is shown in FIG. 3 as pSIM772.

A terminator-free cassette may exist as an extrachromosomal DNA molecule in a cell or it may be integrated by any one of a variety of mechanisms into the nucleus, chromosome, or other endogenous nucleic acid of the cell. If the terminator-free cassette is stably integrated into the genome of the cell, then it may be possible to produce a cell line, cell culture, biological tissue, plant, or organism that comprises the cassette in subsequent cell or organism generations.

Expression of such a construct in a plant will reduce or prevent expression of gene(s) that display either shares sequence identity or inverse complementarity with at least part of a desired polynucleotide. The invention is not bound by any particular theory or mechanism, but the transcripts may, directly or indirectly, affect the activity of a regulatory sequence, such as a promoter, that is normally associated with the expression of a target gene in a cell; or the transcript may negatively affect the accumulation of a transcript that is endogenously produced in the target cell. Accordingly, either or both of transcript accumulation and transcript translation may be altered by the activity of the transcript produced by the expression cassette of the present invention.

A plant of the present invention may be a monocotyledonous plant, for instance, alfalfa, canola, wheat, turf grass, maize, rice, oat, barley, sorghum, orchid, iris, lily, onion, banana, sugarcane, and palm. Alternatively, the plant may be a dicotyledonous plant, for instance, potato, tobacco, tomato, avocado, pepper, sugarbeet, broccoli, cassaya, sweet potato, cotton, poinsettia, legumes, alfalfa, soybean, pea, bean, cucumber, grape, brassica, carrot, strawberry, lettuce, oak, maple, walnut, rose, mint, squash, daisy, and cactus.

The effect of the RNA molecule, which is produced by a terminator-free expression cassette of the present invention, may be assessed by measuring, directly or indirectly, the target nucleic acid or protein level in the cell or environment in which the expression cassette is present. Thus, the effect of an expression cassette of the present invention in downregulating, suppressing, reducing, or preventing or eliminating target gene expression may be identified by a reduction in the amount of RNA transcript that is produced by the target gene, or a reduction in the amount of target gene protein product, or both.

A desired polynucleotide of a terminator-free construct described herein may be identical to, or share sequence identity with different kinds of DNA regions, such as (1) at least part of the sequence that encodes a target transcript, (2) at least part of the intron of a gene that encodes a target transcript, (3) at least part of the promoter of a gene that encodes a target transcript, (4) part of the terminator of a gene that encodes a target transcript, whereby the polynucleotide is not a terminator, (5) the 3'-untranslated region of a gene, and (6) the 5'-untranslated region of a gene. One or more nucleotides of any one of these regions may be mutated, altered, or substituted to increase sequence identity with a target sequence or to otherwise increase or enhance silencing of the target sequence.

The location of the target sequence, therefore, may be in, but is not limited to, (i) the genome of a cell; (ii) at least one RNA transcript normally produced in a cell; or (iii) in a plasmid, construct, vector, or other DNA or RNA vehicle. The cell that contains the genome or which produces the RNA transcript may be the cell of a bacteria, virus, fungus, yeast, fly, worm, plant, reptile, bird, fish, or mammal.

Hence, the target nucleic acid may be one that is normally transcribed into RNA from a cell nucleus, which is then in turn translated into an encoding polypeptide. Alternatively, the target nucleic acid may not actually be expressed in a particular cell or cell type. For instance, a target nucleic acid may be a genomic DNA sequence residing in a nucleus, chromosome, or other genetic material, such as a DNA sequence of mitochondrial DNA. Such a target nucleic acid may be of, but not limited to, a regulatory region, an untranslated region of a gene, or a non-coding sequence.

Alternatively, the target nucleic acid may be foreign to a host cell but is present or expressed by a non-host organism. For instance, a target nucleic acid may be the DNA or RNA molecule endogenous to, or expressed by, an invading parasite, virus, or bacteria.

Furthermore, the target nucleic acid may be a DNA or RNA molecule present or expressed by a disease cell. For instance, the disease cell may be a cancerous cell that expresses an RNA molecule that is not normally expressed in the non-cancerous cell type.

In plants, the desired polynucleotide may share sequence identity with a target nucleic acid that is responsible for a particular trait of a plant. For instance, a desired polynucleotide may produce a transcript that targets and reduces the expression of a polyphenol oxidase gene target in a plant and, thereby, modifies one or more traits or phenotypes associated with black spot bruising. Similarly, a desired polynucleotide may produce a transcript that targets and reduces the expression of a starch-associated R1 target nucleic acid or phosphorylase target nucleic acid in a plant, thereby modifying one or more traits or phenotypes associated with cold-induced sweetening.

An expression cassette in a construct of the present invention may be flanked by one or more transfer-DNA ("T-DNA") border sequences. Any of the expression cassettes described herein, for instance, may be inserted into the T-DNA of an *Agrobacterium*-derived plasmid, such as a Ti plasmid from *A. tumefaciens*.

A border sequence may comprise a sequence that is similar to a traditional *Agrobacterium* T-DNA border sequence, but actually is a sequence that is native to a plant, but which can facilitate transfer and integration of one nucleic acid into another. For instance, such plant-derived transfer-DNA ("P-DNA") border sequences can be isolated from potato (SEQ ID NO: 44), tomato (SEQ ID NOs: 45-46), pepper (SEQ ID NO: 47), alfalfa (SEQ ID NO: 48), barley (SEQ ID NO: 49), and rice (SEQ ID NO: 50) shown in the sequence table elsewhere in this application.

Accordingly, any one of the expression cassettes described herein may be inserted into a transfer-DNA that is delimited by such P-DNA border sequences, which are capable of integrating the cassette into another nucleic acid, such as a plant genome or plant chromosome.

Accordingly, an *Agrobacterium* plasmid, which contains an expression cassette described herein that does not comprise a DNA region that is involved in 3-end formation and polyadenylation of an RNA transcript, may be stably integrated into the genome of a plant via *Agrobacterium*-mediated transformation. The progeny of that transformed plant, therefore, will continue to express the transcripts associated with the expression cassette.

The promoters that are used to initiate transcription of the desired polynucleotide may be constitutive, tissue-preferred, or inducible promoters or permutations thereof. "Strong" promoters, for instance, include the potato ubiquitin-7 and ubiquitin-3 promoters, and ubiquitin promoters from maize, rice, and sugarcane. They also include the rice actin promoter, various rubisco small subunit promoters, rubisco activase promoters, and rice actin promoters. Good tissue-preferred promoters that are mainly expressed in potato tubers include the promoters of the granule-bound starch synthase and ADP glucose pyrophosphorylase genes. There are various inducible promoters, but typically an inducible promoter can be a temperature-sensitive promoter, a chemically-induced promoter, or a temporal promoter. Specifically, an inducible promoter can be a Ha hsp17.7 G4 promoter, a wheat wcs120 promoter, a Rab 16A gene promoter, an α-amylase gene promoter, a pin2 gene promoter, or a carboxylase promoter.

Accordingly, to facilitate identification of a plant that has been successfully transformed with a terminator-free expression cassette, it may be desirable to include within the region delineated by the transfer-DNA border sequences a selectable or screenable marker. Inclusion of a marker is a standard procedure in *Agrobacterium*-mediated transformation and is employed to make it possible to readily identify successfully-transformed plant material. In the expression cassettes depicted in FIGS. 1-4, for instance, the marker is hygromycin phosphtransferase ("hptII"), which confers hygromycin resistance to a plant that expresses that marker. In such cassettes, therefore, a terminator or DNA region that is involved in 3-end formation and polyadenylation of an RNA transcript is operably linked to the hptII gene sequence. Other selectable and screenable markers may be used instead of hptII.

EXAMPLES

Example 1

Conventional Silencing Constructs

The efficacy of various silencing constructs was tested by targeting the beta glucuronidase (gus) reporter gene operationally linked to the strong constitutive promoter of figwort mosaic virus, designated here as "P1" (SEQ ID NO: 1). This test system is stringent because the gus protein is highly stable. Thus, only relatively large reductions in gus transcripts result in phenotypically detectable reductions of gus protein levels. Most silencing constructs contain at least one copy of the same 304-bp gus gene fragment (SEQ ID NO: 2), operably linked in either the sense or antisense orientation to a strong constitutive promoter and in some cases followed by the terminator of the *Agrobacterium* nopaline synthase gene. The silencing constructs were inserted next to an expression cassette for the hygromycin phosphotransferase (hptII) selectable marker gene between the T-DNA borders of transformation vectors. Resulting vectors were used to retransform a tobacco plant that had been transformed before with a T-DNA containing an expression cassette for the gus gene (see also FIGS. 1 and 2).

The following transformation vectors were produced to study the role of a terminator element in conventional silencing constructs:

pSIM714: The negative control vector pSIM714, which does not contain a silencing construct.

pSIM718: Vector pSIM718, which contains a 'sense' gus gene fragment operably linked to the terminator of the nopaline synthase gene (SEQ ID NO: 3) that represents strategies described in, e.g., U.S. Pat. Nos. 5,283,184 and 5,231,020. This vector contains the gus gene fragment operably linked in the sense orientation to the promoter and followed by the terminator.

pSIM140: Vector pSIM140, which is identical to pSIM718 except that the silencing construct does not contain a terminator.

pSIM755: Vector pSIM755, which contains a terminator-containing 'antisense' construct that represents strategies described in, e.g., U.S. Pat. Nos. 5,107,065 and 5,759,829. This vector contains the gus gene fragment operably linked in the sense orientation to the promoter and followed by the terminator.

pSIM758: Vector pSIM758, which is identical to pSIM755 except that the silencing construct does not contain a terminator.

pSIM374: Vector pSIM374, which contains a terminator-containing construct that comprises both a sense and antisense gus gene fragment and represents strategies described in, e.g., WO 99/53050A1. This vector contains two copies of the gus gene fragment, one in the sense orientation and the other one in the antisense orientation and separated from each other by an intron, depicted in SEQ ID NO: 4, and inserted between promoter and terminator.

pSIM728 and 777: Vector pSIM728, which is identical to pSIM374 except that the silencing construct does not contain a terminator. Vector pSIM777 is identical to pSIM728 except that the P2 promoter is at the other side of the expression cassette.

Binary vectors containing the various constructs were introduced into *Agrobacterium*. Ten-fold dilutions of overnight-grown cultures of the resulting strains were grown for five to six hours, precipitated for 15 minutes at 2,800 RPM, washed with MS liquid medium (PhytoTechnology, KS) supplemented with sucrose (3%, pH 5.7) and resuspended in the same medium to 0.2 OD/600 nm. The suspension was then used to infect leaf explants of the transgenic in vitro grown *Nicotiana tabacum* (tobacco) plant expressing the gus gene. Infected explants were incubated for two days on co-culture medium (1/10 MS salts, 3% sucrose, pH 5.7) containing 6 g/L agar at 25° C. in a Percival growth chamber (16/8 hr photoperiod) and subsequently transferred to M401/agar (PhytoTechnology) medium containing timentin (150 mg/L) and hygromycin (20 mg/L). Resulting shoots were transferred to hormone-free rooting medium, and three leaves of each resulting plant were stained for gus expression.

Table 1 shows that all plants retransformed with pSIM714 displayed the same levels of gus expression as the original gus plant, confirming that retransformation, proliferation of single cells, and regeneration does not negatively affect expression of the reporter gene.

Table 1 also shows that the constructs representing the three different conventional silencing methods trigger gus gene silencing with varying efficiencies. In agreement with what has been reported in the literature, pSIM374 is most effective. About half of plants that were retransformed with this constructs display at least some reduced level of gus activity. The two other constructs support a reduction in gus activity in only about 6% of retransformed plants.

Importantly, Table 1 also demonstrates that removal of the terminator dramatically lowers the efficacy of the silencing constructs. For instance, pSIM374 is more than six-fold more efficacious than its terminator-free derivative, pSIM728. Hardly any activity is observed with the terminator-free pSIM758.

It can be concluded that the terminator plays an essential role in optimizing the activity of conventional silencing constructs.

Example 2

Effective Gene Silencing with Terminator-Free Constructs Comprising at Least Two Copies of a Target Gene Fragment that Trigger Convergent Transcription The following transformation vectors were produced to study the effect of convergent transcription on gene silencing (see also FIG. 3):

pSIM715: Vector pSIM715 contains a construct that comprises a first segment consisting of the gus gene fragment operationally linked to the promoter (P1) and a second segment in the opposite orientation that consists of the same gus gene fragment operationally linked to the constitutive 35S promoter of cauliflower mosaic virus, designated 'P2' and depicted in SEQ ID NO: 5, whereby the first and second segment are separated by two different introns.

pSIM717: Vector pSIM717 is identical to pSIM715 except that the two segments of the construct are separated by a single intron.

pSIM789: Vector pSIM789 is identical to pSIM717 except that the P2 promoter is replaced by a P1 promoter.

pSIM771: Vector pSIM771 is identical to pSIM717 except that the P1 promoter is replaced by the potato ubiquitin-7 promoter, which is depicted in SEQ ID NO: 6 and named here 'P3'.

pSIM770: Vector pSIM770 is identical to pSIM717 except that the P2 promoter that drives expression of the selectable marker gene is replaced by P1, and the P1 promoter of the silencing construct is replaced by P2.

pSIM772: Vector pSIM772 contains the gus gene fragment inserted between two different oppositely oriented promoters, P2 and P3 pSIM756: Vector pSIM756 is identical to pSIM717 except that the gus gene fragments are oriented in the inverse complementary orientation relative to the promoter to which they are immediately linked.

pSIM779: Vector pSIM779 is an example of a tandem repeat of gus gene fragments inserted between two convergent promoters.

pSIM787: Vector pSIM787 is similar as pSIM779 but contains four direct repeats of the target gene fragment inserted between convergent promoters.

pSIM1111 is identical to pSIM779 except that the four direct repeats are preceded by an antisense DNA fragment of the gus gene that is different from SEQ ID NO: 2 and depicted as SEQ ID NO: 7.

Gus assays performed on re-transformed gus plants demonstrate that all tested terminator-free constructs that contain two segments, each containing a different promoter driving the gus gene fragment, in the inverse complementary orientation, pSIM715, 717, and 756, 771 are more efficaceous in silencing the gus gene than pSIM374, the construct that represents the best conventional approach. Furthermore, pSIM789 also confers effective gene silencing to many of the double transformants.

The experiment also shows that the use of a single gus gene fragment (pSIM779) is not as efficaceous. This result suggests that convergent transcription of at least two copies of the desired polynucleotide is important for effective silencing.

The experiment also showed that a construct with two direct repeats (pSIM780) triggered gene silencing. However, this arrangement was not as effective as the inverted repeat organization of pSIM756 (Table 1). Furthermore, four directs repeats (pSIM787) are more effective than two direct repeats (Table 1).

To study the molecular basis of terminator-free silencing, RNA was isolated from three plants that had been retransformed with pSIM717 and three additional plants retransformed with pSIM715. In each case, one plant represented an ineffective silencing event whereas the other two plants displayed near-complete gus gene silencing.

Figure 7:
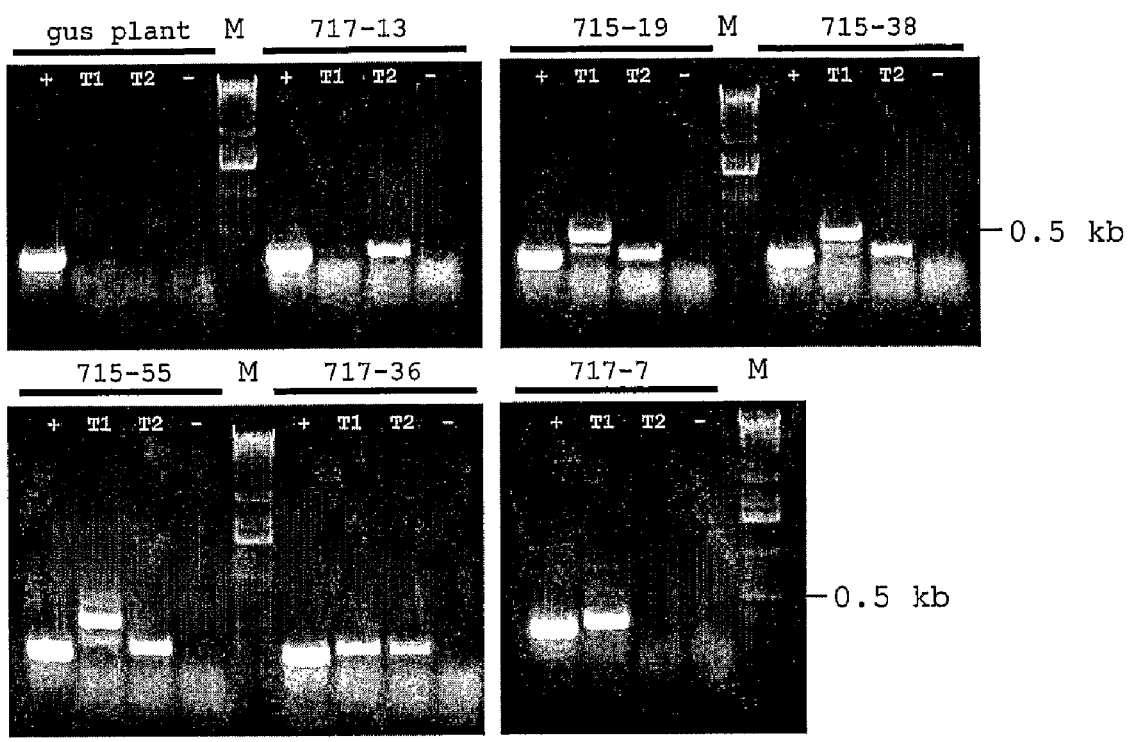
FIG. 7 shows ethidium bromide-stained agarose gels containing the products of RT-PCRs. +=positive plasmid control; −=negative control; M=marker; T1=transcript from P1 promoter; T2=transcript from P2 promoter.

Reverse-transcription polymerase chain reactions (RT-PCRs) were performed to study to production of transcripts from the two different promoters used in pSIM715 and pSIM717. The first primer used for these experiments (PG, shown in SEQ ID NO: 8) is specific for a sequence of the gus gene fragment and anneals to transcripts produced from either strand. The second primer was designed to anneal to intron sequences of one of the strands only (pIF, shown in SEQ ID NO: 9, anneals to a sequence of the GBSS-intron derived spacer region of transcripts produced by the P1 promoter, and PIR, shown in SEQ ID NO: 10, anneals to transcripts produced by the P2 promoter). Interestingly, these studies demonstrated that the construct of the non-silenced plants 717-7 and 717-13 only contained transcripts produced from one of the two strands, either T1 or T2 (FIG. 7). In contrast, the silenced plants 715-19, 715-38, 717-55, and 717-36 produced transcripts from both strands (FIG. 7). Thus, effective silencing is accomplished only if both promoters of the construct are functionally active simultaneously.

Figure 8:
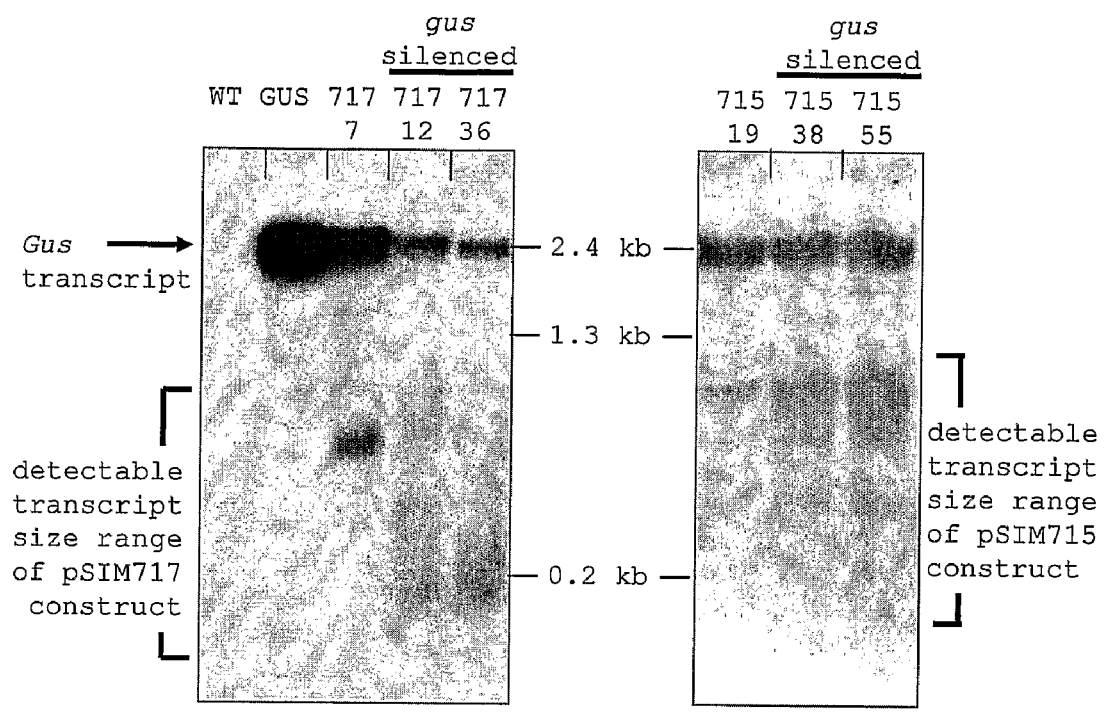
FIG. 8 shows autoradiograms of RNA gel blots. The probe used for hybridization was derived from the gus gene.
Figure 10:
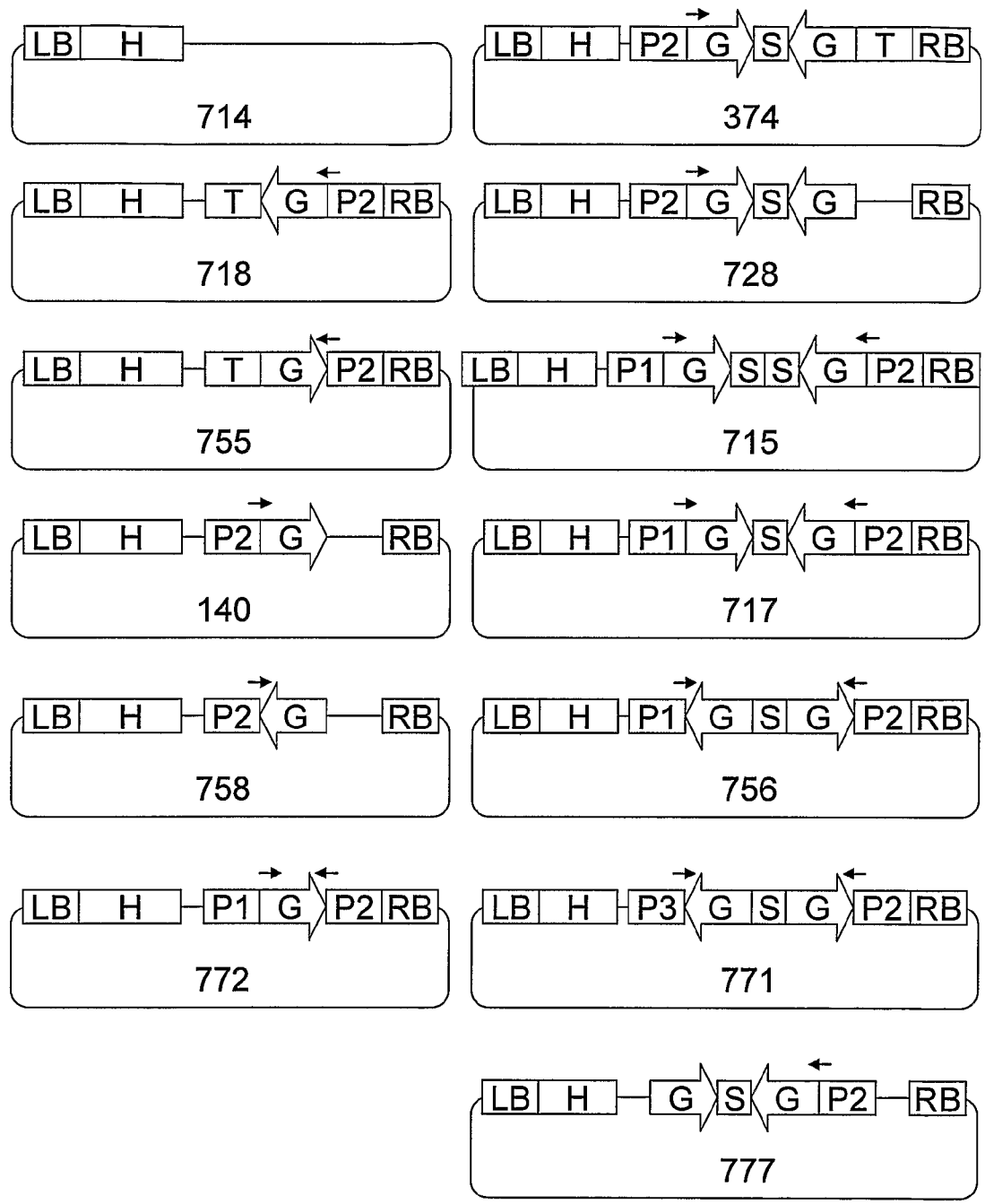
FIG. 10 depicts plasmid maps. G: gus gene fragment; H: expression cassette for hptII gene; LB: left border region; RB: right border region; T: terminator; P1: P1 promoter; P1n: non-functional P1 promoter lacking a TATA box; P2: P2 promoter; P3: P3 promoter; GB: GBSS promoter; PP: PPO gene fragment; PT=fragment of tobacco PPO gene. Direction of transcription is indicated with a small black solid arrow.
Figure 10:
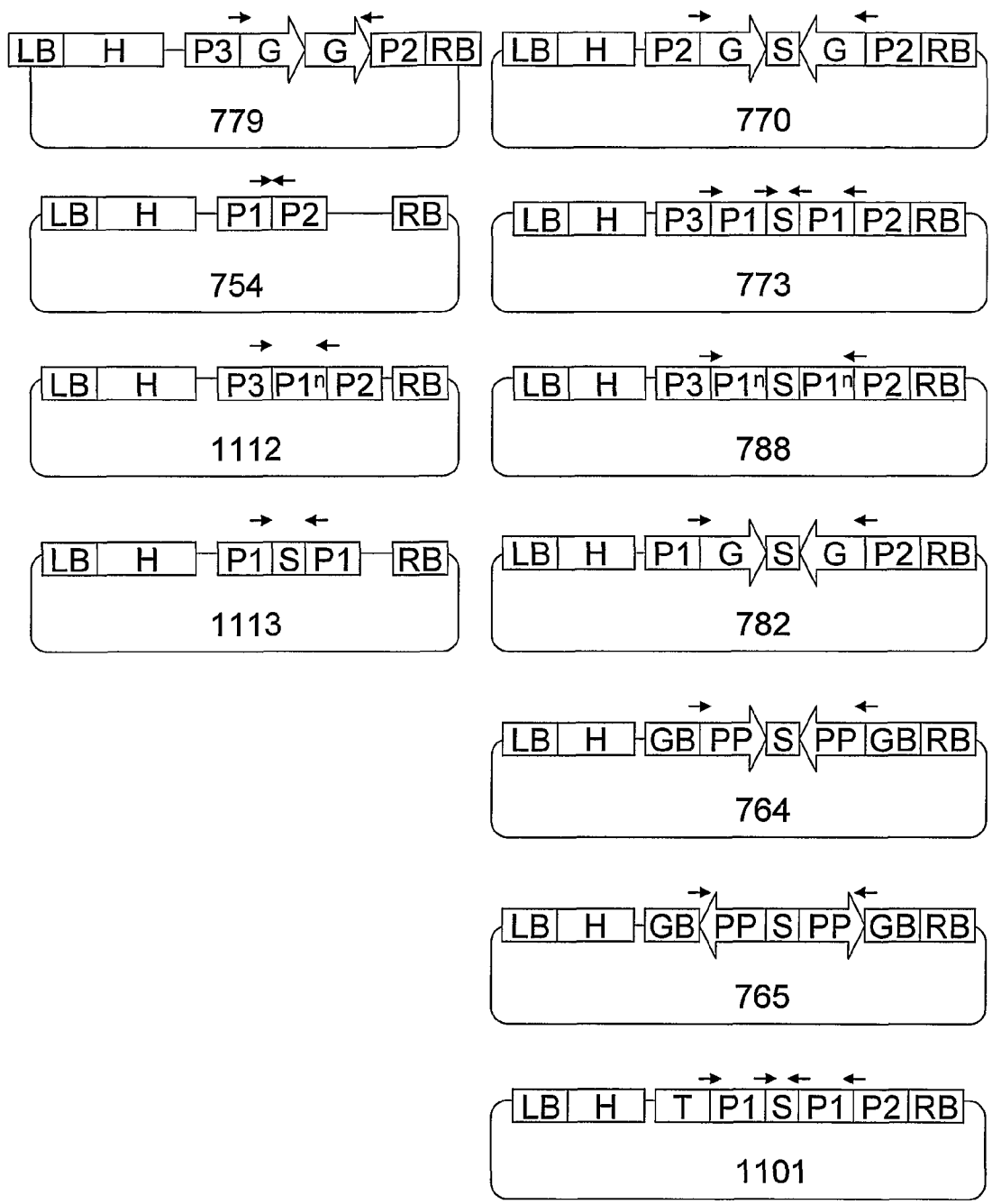
Figure 10:
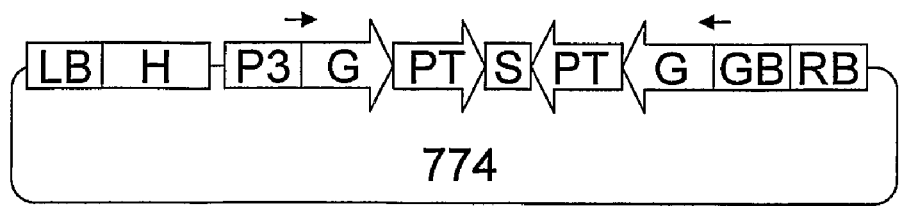
Figure 10:
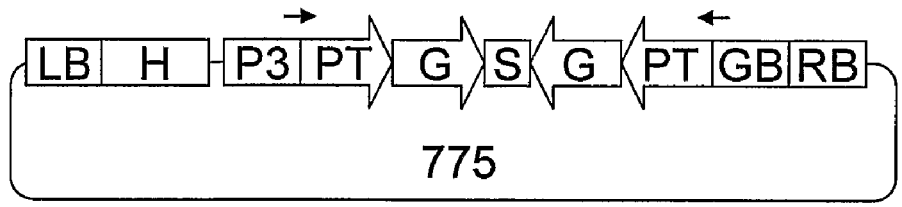
Figure 10:
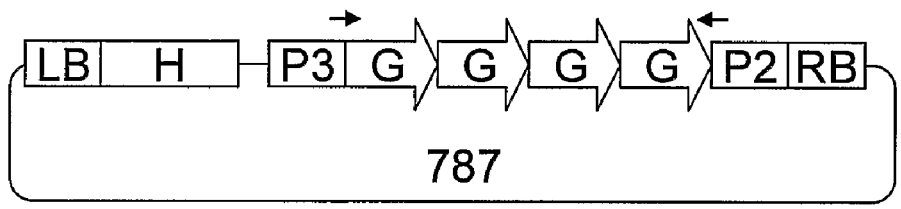
Figure 10:
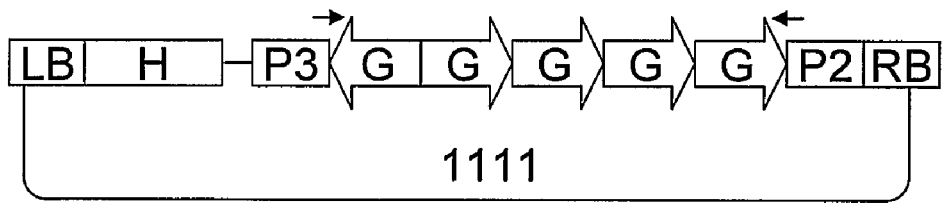
Figure 10:
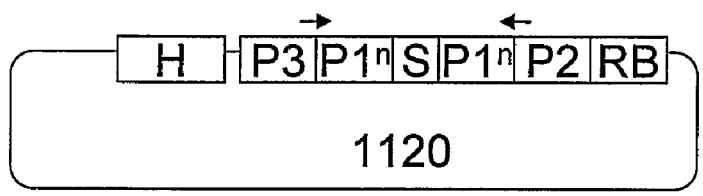
Figure 10:
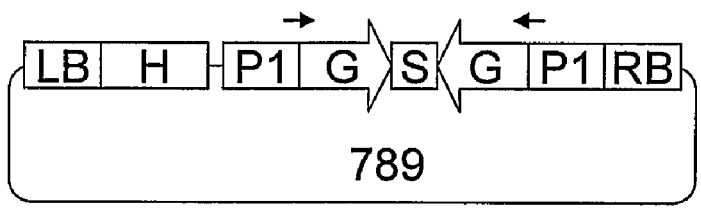

Hybridization of subsequent RNA gel blots with radioactively labeled probes derived from the gus gene demonstrated that effective silencing in 715-38, 715-55, 717-12, 717-36, and 717-19 is correlated with a strong decrease in gus RNA accumulation (FIG. 8). Furthermore, the transcripts produced by the silencing construct in fully silenced plants were generally found to be varying in size from about 0.2-kb to about 1.0-kb (FIG. 8). Although RT-PCR revealed the presence of additional large transcripts that comprise not only the polynucleotide but also downstream promoter sequences, the presence of such transcripts could hardly be detected on RNA gel blots. For instance, hybridization with a probe derived from the P1 promoter required a seven-day exposure time before an extremely faint smear could be observed.

Example 3

Silencing in Potato Tubers

Figure 6:
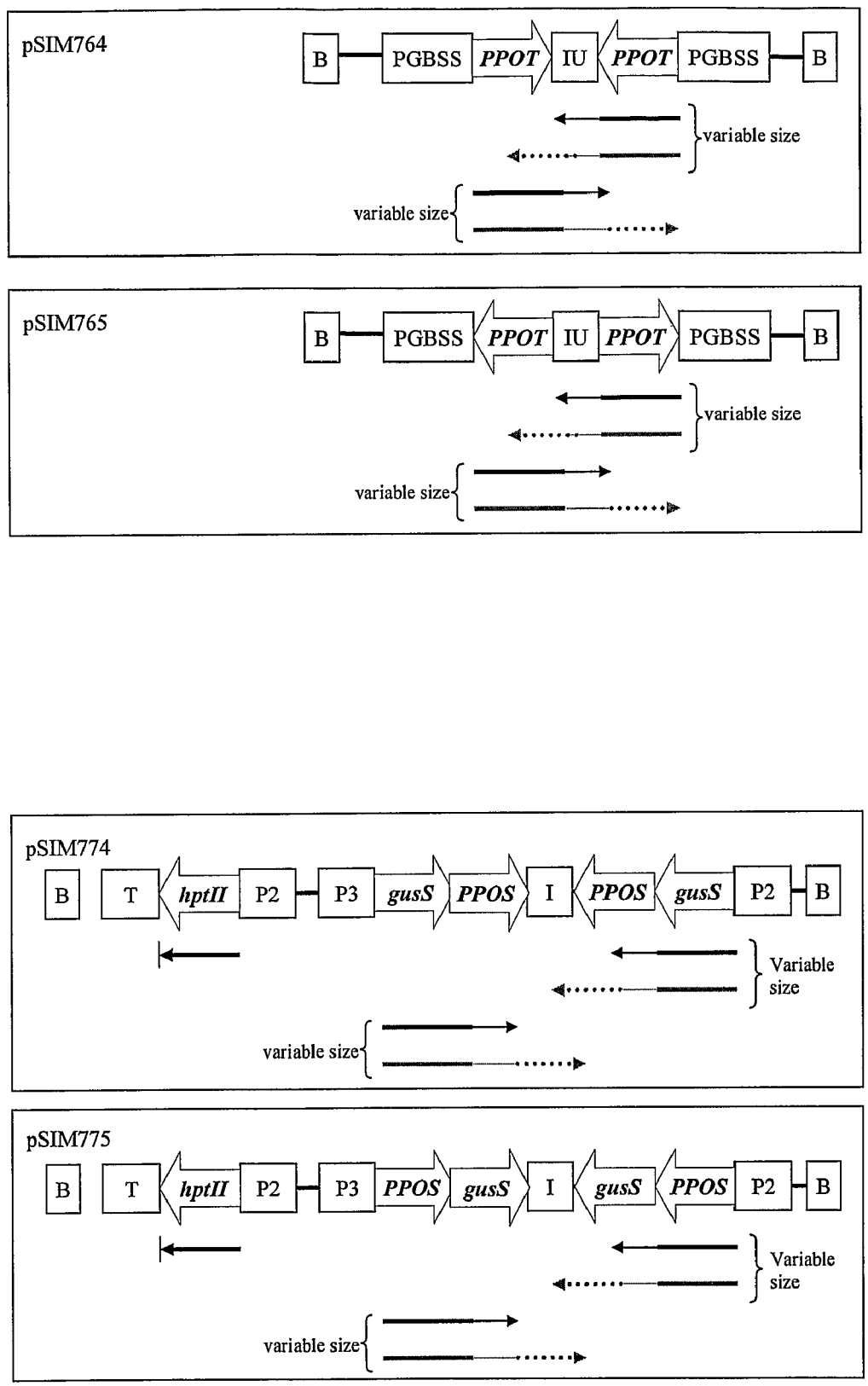
FIG. 6 depicts schematic diagrams for T-DNAs comprising "terminator-free colliding transcription" (TFCT) constructs. Specifically, it illustrates the T-DNAs of pSIM765, pSIM922F, pSIM922G, pSIM774, and pSIM775. The key to the identified elements and solid and dotted arrows is the same as those explained in the legend of FIG. 1. PPO indicates a fragment of the tobacco PPO gene.

Various vectors were developed to test the concept of terminator-free silencing in tubers. These vectors contained an expression cassette for the neomycin phosphotransferase (nptII) gene as selectable marker system (see also FIG. 6). The driver promoters used for gene silencing in potato tubers were selected from the group consisting of: (1) the strong potato ubiquitin-7 promoter, (2) the strong tuber and stolon-specific promoter of the granule-bound starch synthase (GBSS) gene (SEQ ID NO: 12), and (3) the strong tuber-specific promoter of the potato ADP glucose pyrophosphorylase (AGP) gene (SEQ ID NO: 13). See FIG. 4 for maps of the transfer DNAs.

pSIM764: Vector pSIM764 contains a 'tuber-silencing' construct that comprises a first segment consisting of the 154-bp trailer of the potato tuber-expressed PPO gene (SEQ ID NO: 14) operably linked to the GBSS promoter and a second segment in the opposite orientation that consists of the same trailer fragment operably linked to the GBSS promoter whereby the first and second segment are separated by the intron of the potato ubiquitin-7 gene depicted in SEQ ID NO: 15.

pSIM765: Vector pSIM765 is identical to pSIM764 except that the PPO gene fragments are oriented in the opposite orientation.

pSIM217 represents the control plasmid and contains the two copies of the PPO gene inserted as inverted repeat between GBSS promoter and ubiquitin terminator.

Ten-fold dilutions of overnight-grown cultures were grown for 5-6 hours, precipitated for 15 minutes at 2,800 RPM, washed with MS liquid medium (Phytotechnology) supplemented with sucrose (3%, pH 5.7), and resuspended in the same medium to 0.2 OD/600 nm. The resuspended cells were mixed and used to infect 0.4-0.6 mm internodal segments of the potato variety "Ranger Russet". Infected stems were incubated for two days on co-culture medium (1/10 MS salts, 3% sucrose, pH 5.7) containing 6 g/L agar at 22° C. in a Percival growth chamber (16 hrs light) and subsequently transferred to callus induction medium (CIM, MS medium supplemented with 3% sucrose 3, 2.5 mg/L of zeatin riboside, 0.1 mg/L of naphthalene acetic acid, and 6 g/L of agar) containing timentin (150 mg/L) and kanamycin (100 mg/L). After one month of culture on CIM, explants were transferred to shoot induction medium (SIM, MS medium supplemented with 3% sucrose, 2.5 mg/L of zeatin riboside, 0.3 mg/L of giberellic acid GA3, and 6 g/L of agar) containing timentin and kanamycin (150 and 100 mg/L respectively) until shoots arose. Shoots arising at the end of regeneration period were transferrred to MS medium with 3% sucrose, 6 g/L of agar and timentin (150 mg/L). Transgenic plants were transferred to soil and placed in a growth chamber (11 hours light, 25° C.). After three weeks, at least 3 minitubers/line were assayed for PPO activity. For this purpose, 1 g of potato tubers is pulverized in liquid nitrogen, added to 5 ml of 50 mM MOPS (3-(N-morpholino) propane-sulfonic acid) buffer (pH 6.5) containing 50 mM catechol, and incubated at room temperature with rotation for about 1 hour. The solid fraction was precipitated, and the supernatant transferred to another tube to determine PPO activity. For this purpose, 1 g of potato tubers was pulverized in liquid nitrogen. This powder was then added to 5 ml of 50 mM MOPS (3-(N-morpholino) propane-sulfonic acid) buffer (pH 6.5) containing 50 mM catechol, and incubated at room temperature with rotation for about 1 hour. The solid fraction was then precipitated, and the supernatant transferred to another tube to determine PPO activity by measuring the change of OD-410 over time. The experiment demonstrated that pSIM764 and 765 trigger effective silencing in potato tubers (Table 2). A comparison with data presented in WO 2003/069980 demonstrates that the method of the present invention can be more effective than that of conventional terminator-based gene silencing as exemplified by pSIM217, the PPO control.

Example 4

Multi-Gene Silencing in Tobacco

Two constructs were created to study the effect of the position of gene fragments within the silencing construct. For this purpose, the two copies of the gus gene fragment of pSIM771 were replaced by two copies of the gus gene fragment linked to a fragment of the tobacco polyphenol oxidase (PPO) gene (SEQ ID NO: 16) (also, see FIG. 6):

pSIM774: Vector pSIM774 contains a silencing construct with the gus gene fragments immediately linked to the promoters and the adjacent PPO gene fragments linked to the central intron.

pSIM775: Vector pSIM775 contains a silencing construct with the PPO gene fragments immediately linked to the promoters and the adjacent gus gene fragments linked to the central intron.

Retransformation of gus plants with these vectors is expected to trigger silencing as efficiently as pSIM771.

Example 5

Multi-Gene Silencing in Potato

Multiple gene silencing is implemented by simultaneously targeting three undesirable potato tuber genes.

Plasmid pSIM1121 (Russet Boise II) comprises an all-native transfer DNA depicted in SEQ ID NO: 17 comprising a silencing construct comprising two copies of a DNA segment, separated by the intron of the potato ubiquitin-7 gene and positioned as inverted repeat between two convergent GBSS promoters, whereby the DNA segment comprises (i) a fragment of the trailer of the tuber-expressed polyphenol oxidase gene of the wild potato relative Solanum verrucosum Schltdl. TRHRG 193, accession number 498062 (see: USDA, ARS, National Genetic Resources Program. Germplasm Resources Information Network—(GRIN). [Online Database] National Germplasm Resources Laboratory, Beltsville, Md. (SEQ ID NO: 18) (ii) a fragment of the leader of the phosphorylase L gene (SEQ ID NO: 19), and (iii) a fragment of the leader of the R1 gene (SEQ ID NO: 20).

Employment of this plasmid makes it possible to produce transformed potato plants that only contain native DNA and display the following new traits: (1) bruise tolerance due to silencing of the tuber-expressed PPO gene, (2) reduced cold-induced glucose accumulation due to silencing of the phosphorylase and R1 genes.

Example 6

Highly Effective Promoter Targeting

The following transformation vectors were produced to demonstrate that sequences of the target promoter can be used to silence expression of the target gene (see also FIG. 4):

pSIM773: Vector pSIM773 contains a construct that comprises a first segment comprising the P3 promoter linked to P1, and a second segment, which is oriented in the opposite orientation, and which comprises the P2 linked to P1. The first and second segment are separated by an intron. Thus, this construct contains four functionally active promoters. The two promoters in the middle are identical, represent the target promoter, and are in convergent orientation. The two outside promoters are different to each other and in convergent orientation. All four promoters contain a TATA box and proceed up to a base pair upstream from the transcription start.

pSIM1101: Vector pSIM1101 is identical to pSIM773 except that the P3 promoter was replaced by the nos terminator.

pSIM788: Vector pSIM788 is similar to pSIM773 except that the two central P1 promoters of the target gus gene only contain sequences upstream from the TATA box, (SEQ ID NO: 21), thus representing non-functional promoters.

pSIM1120: Vector pSIM1120 is similar to pSIM773 except that the two central promoters of the target gene lack a TATA box and are not in convergent but divergent orientation.

pSIM1112: Vector pSIM1112 contains a single non-functional P1 promoter inserted between convergent P2 and P3 promoter.

pSIM1113: Vector pSIM1113 contains two convergent P1 promoters separated by an intron.

pSIM754: Control vector pSIM754 contains the P1 promoter driving expression of the P2 promoter, and vice versa.

Retransformation of gus plants with pSIM773 yielded 35 hygromycin resistant plants. PCR analysis confirmed the presence of the transfer DNA of pSIM773. Surprisingly, subsequent gus staining revealed an extremely effective complete silencing of the gus gene (Table 1). Twenty plants (57%) did not display any detectable gus expression. Thus, promoter targeting using the pSIM773 strategy is highly desirable.

Similar results were obtained with the target promoters in divergent orientation inserted between two convergent driver promoters, with 77% of plants that had been retransformed with pSIM1120 displaying full gus gene silencing (Table 1).

Table 1 shows that gene silencing was also accomplished by using a single target promoter inserted between two convergent driver promoters (pSIM1112). However, this method may be less effective than methods that employ two copies of the target promoter oriented as inverted repeat.

Furthermore, efficacy of pSIM1113 demonstrates that driver promoters are not always necessary. It is possible to effectively silencing a gene by simply employing two convergent target promoters (Table 1).

Many (44%) of the plants that were retransformed with pSIM1101 also displayed full gene silencing (Table 1). This finding demonstrates that promoter-based silencing does not require convergent transcription.

Conventional silencing methods have often been found to not provide stable gene silencing in subsequent generations. In contrast, four-promoter constructs represented by pSIM773 gave full silencing that is completely maintained upon transmission of the silencing cassette to the next generation. The enhanced stability was demonstrated by allowing double transformed tobacco plants to mature, and subsequently determining gus expression levels in T1 progenies. This study showed that 100% of the progeny plants that were derived from a pSIM773 plant and contained both gus gene and silencing cassette displayed full gus gene silencing (Table 3). In contrast, none of the T1 plants carrying the gus gene and pSIM374 silencing cassette displayed full gus gene silencing (Table 3). An intermediair phenotype was observed by analyzing the progeny of a plant carrying the gus gene and the silencing cassette of pSIM717 (Table 3).

Example 7

Sequence Requirements for Promoter Targeting

The above experiments demonstrated that promoter sequences can be used to effectively trigger gene silencing. However, they should not be understood to imply that any promoter fragment of the target gene could be employed for this purpose.

To study the sequence requirements for promoter-based silencing, two vectors were created that comprise two copies of only part of the P1 promoter inserted as inverted repeat between the driver promoters.

pSIM1118: Vector pSIM1118 contains two copies of an upstream 300-bp fragment of the promoter shown in SEQ ID NO: 11.

pSIM1119: Vector pSIM1119 contains two copies of a central 300-bp region of the P1 promoter shown in SEQ ID NO: 51.

Retransformation of gus plants with the two different constructs yielded 34 and 20 plants, respectively, that were analyzed histochemically. Interestingly, none of the analyzed plants displayed any reduced gus expression, indicating that the employed promoter fragments did not effectively trigger gene silencing (Table 1).

FIG. 9 shows a sequence analysis of the various promoter fragments. The fragment that facilitates effective gene silencing is present in pSIM773, 788, 1101, and 1120 but not in pSIM1118 and 1119.

Example 8

Reduced Cold-Sweetening in Tubers of Potato Plants Containing a Silencing Construct Comprising Two Copies of a Fragment of the Promoter of the R1 Gene The sequence of the promoter of the potato starch-associated R1 gene, including leader and start codon, is shown in SEQ ID NO: 22. Two copies of a short (342-bp) R1 promoter fragment (SEQ ID NO: 23) were inserted as inverted repeat between either two convergently oriented promoters of the GBSS promoter (in plasmid pSIM1038) or a GBSS and AGP promoter in convergent orientation (in plasmid pSIM1043). The resulting binary vectors were used to produce transformed potato plants. These plants will be allowed to develop tubers, and the tubers will be stored for about a month or longer at 4° C. Glucose analysis of the cold-stored tubers will demonstrate that the transformed plants accumulate less glucose than untransformed control plants. The reduced accumulation of glucose will lower color formation during French fry processing and, thus, make it possible to reduce blanch time and preserve more of the original potato flavor. Furthermore, promoter-mediated R1 gene silencing will limit starch phosphorylation and, therefore, reduce the environmental issues related to the release of waste water containing potato starch. Other benefits of the transformed tubers include: (1) resulting French fries will contain lower amounts of the toxic compound acrylamide, which is formed through a reaction between glucose and asparagine, and (2) resulting fries will display a crisper phenotype, as evaluated by professional sensory panels, due to the slightly altered structure of the starch.

Similar results can be obtained by employing a shorter (151-bp) part of the R1 promoter, shown in SEQ ID NO. 24. Binary vector pSIM1056 comprises two copies of this fragment inserted as inverted repeat between two convergently oriented GBSS promoters; pSIM1062 comprises the fragments inserted between convergently oriented GBSS and AGP promoters. This vector was used to produce 25 transformed plants, which can be shown to display reduced cold-induced glucose accumulation and all benefits associated with that trait.

Example 9

Enhanced Blackspot Bruise Tolerance in Tubers of Potato Plants Containing a Silencing Construct Comprising Two Copies of a Fragment of the Promoter of the Polyphenol Oxidase Gene The sequence of the promoter of the potato tuber-expressed polyphenol oxidase gene is shown in SEQ ID NO: 25. Two copies of a 200-bp PPO promoter fragment (SEQ ID NO: 26) were inserted as inverted repeat between convergent GBSS and AGP promoters. A binary vector comprising this silencing construct, designated pSIM1046, was used to produce twenty-five transformed potato plants. The plants can be allowed to develop tubers, and the tubers can be assayed for polyphenol oxidase activity. Such an analysis will show that the expression level of the targeted PPO gene is reduced if compared to levels in untransformed controls.

In a similar way, plasmid pSIM1045, which contains two copies of a 460-bp PPO promoter fragment (SEQ ID NO: 27) inserted between convergent GBSS and AGP promoters, can be used to lower PPO gene expression.

Similar strategies can be used in other crop species to limit bruise. For instance, the promoter of the leaf-expressed PPO gene of lettuce can be used to reduce bruise in lettuce leaves, the promoter of the fruit-expressed PPO gene of apple can be used to reduce bruise in apple fruit, and the promoter of the seed-expressed PPO gene of wheat can be used to reduce bruise in wheat grains. In all these and other cases, the promoter can be isolated straightforwardly by designing primers that anneal to the known PPO gene sequences, and performing well-known DNA isolation methods such as inverse PCR.

Example 10

Improved Oil Content in Seeds of Canola Plants Containing a Silencing Construct Comprising Two Copies of a Fragment of the Promoter of the Fad2 Gene The sequence of the promoter of the Brassica Fad2 gene, including leader, intron, and start codon, is shown in SEQ ID NO: 28. Two copies of a fragment of this promoter lacking any transcribed sequences such as the 441-bp fragment shown in SEQ ID 29 can be placed as inverted repeat between two convergently oriented promoters that are expressed in Brassica seeds. Examples of 'driver' promoters are: the promoter of a napin (1.7S seed storage protein gene) gene shown in SEQ ID NO: 30 or the promoter of a stearoyl-ACP desaturase gene (SEQ ID NO: 31).

The silencing cassette can be placed within the transfer DNA sequence of a binary vector, and this binary vector can be used to transform Brassica. Some of the resulting plants will produce seed that contains increased amounts of oleic acid.

Other promoters that can be used in silencing constructs to improve oil composition in oilseed crops such as canola, soybean, cotton, and sunflower include promoters of other genes of the fatty acid biosynthesis pathway. For instance, a promoter of a target fatty acid desaturase 12, or microsomal omega-6 fatty acid desaturase, (FAD12) gene (e.g., Genbank Accession Nr. AF243045 for canola and AB188250 for soybean) such as the soybean FAD12 promoter shown in SEQ ID NO: 32 can be used to increase oleic acid levels in crops such as canola and soybean.

Furthermore, promoters of the cotton stearoyl-acyl-carrier protein delta 9-desaturase and oleoyl-phosphatidylcholine omega 6-desaturase genes can be used to increase stearic acid and oleic acid levels, respectively, in cotton. This promoter can be identified by performing methods such as inverse PCR using the known sequence of the target genes (Liu et al., Plant Physiol 129:1732-43, 2002). Two copies of the newly isolated promoter can then be used in strategies similar to that shown for pSIM773 whereby the 'driver' seed-specific promoters can either represent foreign DNA or native DNA.

Example 11

Reduced Lignin Content in the Vascular System of Alfalfa Plants Containing a Silencing Construct Comprising Two Copies of a Fragment of the Promoter of the Comt Gene The promoter of the *Medicago sativa* (alfalfa) caffeic acid/ 5-hydroxyferulic acid 3/5-O-methyltransferase (COMT) gene, including leader, is shown in SEQ ID NO: 33.

Two copies of a 448-bp promoter fragment that lacks transcribed sequences (SEQ ID NO: 34) were inserted as inverted repeat between two convergently oriented driver promoters. The first driver promoter is the promoter of the petE gene shown in SEQ ID NO: 35; the second promoter is the promoter of the Pal gene shown in SEQ ID NO: 36. A binary vector comprising this silencing construct, designated pSIM1117, was used to produce transformed alfalfa plants. Stem tissues of the plants were assayed and shown to contain reduced levels of lignin.

Reduced lignin content can be determined according to the following protocol: (i) cut stem sections and place them on watch glass, (ii) immerse the cut stems in 1% potassium permanganate for 5 min at room temperature, (iii) discard the potassium permanganate solution using a disposable pipette and wash the samples twice with water to remove excess potassium permanganate, (iv) add 6% HCl (V/V) and let the color of the sections turn from black or dark brown to light brown, (v) if necessary, add additional HCl to facilitate the removal of dark color, (vi) discard the HCl and wash the samples twice with water, (vii) add few drops of 15% sodium bicarbonate solution (some times it may not go into solution completely), a dark red or red-purple color develops for hardwoods (higher in S units) and brown color for softwood (higher in G units).

Nineteen transformed alfalfa lines were tested for reduced lignin content, and six plants were found to accumulate reduced amounts of the S-unit of lignin.

Instead of the promoter of the COMT gene, it is also possible to use the promoter of the caffeoyl CoA 3-O-methyltransferase (CCOMT) gene. The sequence of this promoter, together with downstream leader, is shown in SEQ ID NO: 37. A fragment of SEQ ID NO: 29 that lacks transcribed sequences as depicted in SEQ ID NR: 38 can be used to lower lignin content.

Similarly, lignin can be reduced in trees by using promoters of genes involved in lignin biosynthesis. It is also possible to use SEQ ID NO: 59 and reduce lignin content in maize by employing the above-described promoter-based silencing approach.

Example 12

Increased Shelf Life of Fruits of Tomato Plants Containing a Silencing Construct Comprising Two Copies of a Fragment of the Promoter of the Polygalacturonase Gene A promoter of a target polygalacturonase gene such as the tomato promoter shown in SEQ ID NO: 39 can be used to reduce breakdown of pectin, thus slowing cell wall degradation, delaying softening, enhancing viscosity characteristics, and increasing shelf life in tomato by inserting two copies of the promoter fragment as inverted repeat between convergent fruit-specific driver promoters.

Example 13

Reduced Allergenicity of Foods from Plants Containing a Silencing Construct Comprising Two Copies of a Fragment of the Promoter of Genes Encoding Allergens The promoter of the major apple allergen Mal d 1 gene can be isolated by employing inverse PCR methods using the known gene sequence (Gilissen et al., J Allergy Clin Immunol 115:364-9, 2005), and this promoter can then be used to develop apple varieties that contain lower allergenicity levels.

Similarly, the promoter of the major peanut allergen Ara h 2 (Dodo et al., Curr Allergy Asthma Rep 5, 67-73, 2005) can be isolated using inverse PCR methods, and used to develop peanut varieties that contain lower allergenicity levels.

Furthermore, the promoter of the major soybean allergen Gly m Bd 30 K (Herman et al., Plant Physiol 132, 36-43, 2003) can be isolated using inverse PCR methods, and used to develop peanut varieties that contain lower allergenicity levels.

Example 14

Multi-Gene Silencing Approach Based on a Combination of Gene and Promoter Fragments Plasmid pSIM870 (Russet Boise III) comprises an all-native transfer DNA depicted in SEQ ID NO. 40 comprising (1) a first silencing cassette comprising two copies of a DNA segment positioned as inverted repeat between two convergent GBSS promoters whereby the DNA segment comprises (i) a fragment of the trailer of the tuber-expressed polyphenol oxidase gene of *Solanum verrucosum*, (ii) a fragment of the leader of the phosphorylase L gene, and (iii) a fragment of the trailer of the phosphorylase L gene (SEQ ID NO: 41), and (2) a second silencing cassette comprising two copies of the R1 promoter positioned as inverted repeat between the driver promoters of the AGP and GBSS genes, respectively.

Plasmid pSIM899 (Russet Boise IV) comprises an all-native transfer DNA depicted in SEQ ID NO: 42 comprising a first silencing cassette comprising two copies of a DNA segment positioned as inverted repeat between two convergent GBSS promoters whereby the DNA segment comprises (i) a fragment of the trailer of the tuber-expressed polyphenol oxidase gene of *Solanum verrucosum*, and (ii) a fragment of the leader of the phosphorylase L gene, and a second silencing cassette comprising four copies of the leader of the R1 gene operably linked to the AGP promoter and followed by an inverted repeat comprising a sense and antisense fragment of the R1 gene.

Potato transformation with any of these three plasmids will produce plants that, compared to untransformed plants, display the following characteristics: (1) reduced expression of the tuber-expressed polyphenol oxidase gene and, consequently, (i) increased tuber polyphenol content as can be determined by xx, and (ii) enhanced tolerance to tuber black spot bruise as can be determined by xx, and (2) strongly reduced expression of the phosphorylase and R1 genes and, consequently, (i) reduced starch phosphorylation and, consequently, lowered phosphate content of waste waters containing potato starch, and (ii) a reduced conversion of starch into glucose during cold-storage as determined by using the glucose oxidase/peroxidase reagent (Megazyme, Ireland), resulting in (a) less caramelization, and consequently, reduced color formation during frying, which makes it possible to store at higher temperatures and/or blanch for shorter time periods (b) less formation of acrylamide, and (c) increased crispness of fries.

Example 15

Intron Targeting

The polynucleotide used to generate a TFCT construct can contain the intron of a gene that produces the target transcript. The concept of intron-targeted silencing can be demonstrated by using the intron of the gus gene that is expressed in transgenic tobacco.

Figure 5:
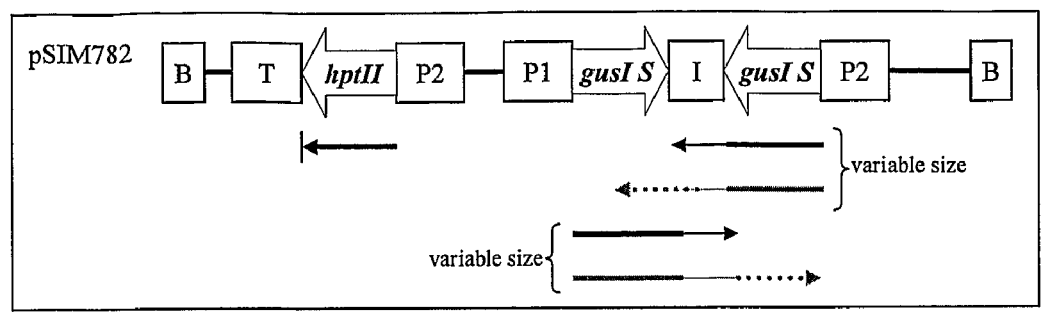
FIG. 5 depicts schematic diagrams for T-DNAs comprising "terminator-free colliding transcription" (TFCT) constructs. Specifically, it illustrates the T-DNAs of pSIM782. The key to the identified elements and solid and dotted arrows is the same as those explained in the legend of FIG. 1. gusI indicates the intronm of the gus gene.

The following transformation vector was produced to demonstrate that sequences of the target intron can be used to silence expression of the target gene (see also FIG. 5):

Vector pSIM782, which contains a construct that comprises a first segment consisting of the intron of the gus gene operationally linked to the promoter (P1) and a second segment in the opposite orientation that consists of the same gus gene intron operationally linked to a second constitutive promoter (P2) whereby the first and second segment are separated by an intron.

An example of an intron that can be used to silence a gene is the intron of the *Solanum vernei* starch-associated R1 gene SEQ ID NO: 44. R1 gene silencing will reduce the extent of cold-induced sweetening in tubers during storage.

Example 16

Terminator Targeting

The polynucleotide used to generate a TFCT construct can comprise sequences downstream from the transcribed sequences of a target gene. This concept can be demonstrated by using the sequences downstream from the gus gene that is expressed in transgenic tobacco.

Example 17

Reduced Lignin Content in the Vascular System of Alfalfa Plants Containing a Silencing Construct Comprising Two Copies of a Fragment of the Comt Gene A binary vector designated pSIM856 was assembled comprising an expression cassette comprising two Comt gene fragments depicted in SEQ ID NOs: 52 and 53, positioned as inverted repeat between two convergent alfalfa promoters shown in SEQ ID NOs: 54 and 55 in such a way that the promoters are operably linked to first the antisense fragment and then the sense fragment. The expression cassette is inserted between alfalfa derived sequences that function as replacement for *Agrobacterium* borders and are shown in SEQ ID NOs: 56 and 57. The entire transfer DNA, depicted in SEQ ID NO: 58 is inserted into a plasmid that carries an expression cassette for the *Agrobacterium* ipt gene in its backbone.

Transformations were carried out as described in Weeks and Rommens, US patent application US20050034188A1, which is incorporated herein by reference. Two transformed plants were tested for lignin content, and both were found to not visibly accumulate the $-unit.

TABLES

TABLE 1

Efficacy of conventional and terminator-free silencing constructs.

| Construct for 2nd transformation | Tobacco plants assayed | gus expression | | | |
|---|---|---|---|---|---|
| | | 50-100% | 10-50% | 1-10% | 0% |
| none | 3 | 3 (100%) | 0 | 0 | 0 |
| PSIM714 | 8 | 8 (100%) | 0 | 0 | 0 |
| PSIM374 | 36 | 13 (36%) | 11 (31%) | 9 (25%) | 3 (8%) |
| PSIM718 | 35 | 33 (95%) | 1 (3%) | 1 (3%) | 0 |
| PSIM728 | 23 | 15 (65%) | 5 (22%) | 3 (13%) | 0 |
| PSIM715 | 37 | 10 (27%) | 11 (30%) | 15 (41%) | 1 (3%) |
| PSIM717 | 35 | 11 (31%) | 3 (9%) | 19 (54%) | 2 (6%) |
| pSIM754 | 38 | 38 (100%) | 0 | 0 | 0 |
| PSIM755 | 36 | 35 (97%) | 0 | 0 | 1 (3%) |
| pSIM756 | 37 | 18 (49%) | 12 (32%) | 5 (14%) | 2 (5%) |
| PSIM758 | 29 | 29 (100%) | 0 | 0 | 0 |
| PSIM770 | 38 | 35 (92%) | 3 (8%) | 0 | 0 |
| PSIM771 | 35 | 20 (57%) | 3 (9%) | 9 (26%) | 3 (9%) |
| PSIM772 | 35 | 34 (97%) | 0 | 1 (3%) | 0 |
| PSIM773 | 35 | 15 (43%) | 0 | 0 | 20 (57%) |
| PSIM774 | 35 | 31 (89%) | 2 (6%) | 2 (6%) | 1 (3%) |
| PSIM775 | 36 | 22 (61%) | 6 (17%) | 7 (19%) | 1 (3%) |
| PSIM777 | 36 | 33 (92%) | 1 (3%) | 1 (3%) | 1 (3%) |
| PSIM778 | 36 | 32 (89%) | 2 (6%) | 2 (6%) | 0 |
| PSIM779 | 36 | 33 (92%) | 1 (3%) | 2 (6%) | 0 |
| PSIM782 | 35 | 34 (97%) | 0 | 1 (3%) | 0 |
| PSIM787 | 32 | 20 (63%) | 7 (22%) | 3 (9%) | 2 (6%) |
| PSIM788 | 35 | 14 (40%) | 0 | 0 | 21 (60%) |
| PSIM789 | 35 | 19 (54%) | 4 (11%) | 6 (17%) | 6 (17%) |
| PSIM1101 | 34 | 14 (41%) | 0 | 5 (15%) | 15 (44%) |
| PSIM1111 | 36 | 21 (58%) | 9 (25%) | 6 (17%) | 0 |
| pSIM1112 | 36 | 33 (92%) | 1 (3%) | 0 | 2 (6%) |
| pSIM1113 | 34 | 24 (71%) | 2 (6%) | 3 (9%) | 5 (15%) |
| PSIM1118 | 34 | 34 (100%) | 0 | 0 | 0 |
| PSIM1119 | 20 | 20 (100%) | 0 | 0 | 0 |
| pSIM1120 | 35 | 8 (23%) | 0 | 0 | 27 (77%) |

TABLE 2

PPO activity in potato mini tubers.

| | rep-1(OD) | rep-2 (OD) | rep-3 (OD) | % of WT | S.E. |
|---|---|---|---|---|---|
| Control | | | | | |
| wt-1 | 0.127 | 0.121 | 0.137 | 87 | 2.6 |
| wt-2 | 0.129 | 0.141 | 0.125 | 89 | 2.7 |
| wt-3 | 0.138 | 0.146 | 0.123 | 92 | 3.7 |
| wt-4 | 0.134 | 0.157 | 0.159 | 101 | 4.4 |
| wt-5 | 0.152 | 0.173 | 0.169 | 111 | 3.6 |

TABLE 2-continued

PPO activity in potato mini tubers.

| | rep-1(OD) | rep-2 (OD) | rep-3 (OD) | % of WT | S.E. |
|---|---|---|---|---|---|
| Wt-6 | 0.153 | 0.152 | 0.151 | 103 | 0.3 |
| Wt-7 | 0.173 | 0.158 | 0.167 | 112 | 2.4 |
| wt-8 | 0.149 | 0.165 | 0.152 | 105 | 2.7 |
| 401-1 | 0.138 | 0.155 | 0.174 | 105 | 5.7 |
| 401-2 | 0.182 | 0.193 | 0.163 | 121 | 4.8 |
| 401-3 | 0.139 | 0.145 | 0.152 | 98 | 2.1 |
| pSIM764 | | | | | |
| 1 | 0.051 | 0.055 | 0.060 | 37 | 1.4 |
| 2 | 0.071 | 0.072 | 0.068 | 48 | 0.7 |
| 3 | 0.063 | 0.070 | 0.075 | 47 | 1.9 |
| 4 | 0.035 | 0.032 | 0.030 | 22 | 0.8 |
| 5 | 0.045 | 0.031 | 0.030 | 24 | 2.7 |
| 6 | 0.053 | 0.056 | 0.056 | 37 | 0.6 |
| 7 | 0.079 | 0.108 | 0.117 | 68 | 6.3 |
| 8 | 0.035 | 0.042 | 0.041 | 27 | 1.2 |
| 9 | 0.039 | 0.042 | 0.043 | 28 | 0.7 |
| 10 | 0.081 | 0.073 | 0.077 | 52 | 1.3 |
| 11 | 0.059 | 0.061 | 0.052 | 39 | 1.5 |
| 12 | 0.055 | 0.046 | 0.053 | 35 | 1.5 |
| 13 | 0.036 | 0.039 | 0.032 | 24 | 1.1 |
| 14 | 0.052 | 0.068 | 0.062 | 41 | 2.6 |
| 15 | 0.037 | 0.033 | 0.034 | 23 | 0.7 |
| 16 | 0.066 | 0.057 | 0.066 | 43 | 1.7 |
| 17 | 0.063 | 0.061 | 0.057 | 41 | 1.0 |
| 18 | 0.063 | 0.041 | 0.047 | 34 | 3.6 |
| 19 | 0.045 | 0.049 | 0.041 | 30 | 1.3 |
| 20 | 0.061 | 0.051 | 0.048 | 36 | 2.2 |
| 21 | 0.043 | 0.039 | 0.039 | 27 | 0.7 |
| 22 | 0.111 | 0.102 | 0.112 | 73 | 1.8 |
| 23 | 0.058 | 0.049 | 0.057 | 37 | 1.6 |
| 24 | 0.043 | 0.041 | 0.042 | 28 | 0.3 |
| 25 | 0.041 | 0.040 | 0.045 | 28 | 0.8 |
| 26 | 0.044 | 0.042 | 0.042 | 29 | 0.4 |
| pSIM765 | | | | | |
| 1 | 0.044 | 0.035 | 0.039 | 27 | 1.4 |
| 2 | 0.041 | 0.048 | 0.055 | 32 | 2.2 |
| 3 | 0.064 | 0.060 | 0.058 | 41 | 1.0 |
| 5 | 0.122 | 0.118 | 0.102 | 77 | 3.4 |
| 10 | 0.042 | 0.066 | 0.059 | 38 | 3.9 |
| 14 | 0.087 | 0.103 | 0.111 | 68 | 3.9 |
| 15 | 0.045 | 0.049 | 0.059 | 34 | 2.3 |
| 16 | 0.033 | 0.042 | 0.035 | 25 | 1.5 |
| 19 | 0.033 | 0.048 | 0.045 | 28 | 2.5 |
| 20 | 0.043 | 0.040 | 0.052 | 30 | 2.0 |
| 21 | 0.044 | 0.035 | 0.033 | 25 | 1.9 |
| 24 | 0.046 | 0.049 | 0.047 | 32 | 0.5 |
| 28 | 0.046 | 0.048 | 0.033 | 29 | 2.6 |
| 29 | 0.071 | 0.082 | 0.078 | 52 | 1.8 |
| 30 | 0.051 | 0.059 | 0.056 | 37 | 1.3 |
| 32 | 0.105 | 0.134 | 0.129 | 83 | 4.9 |
| 34 | 0.045 | 0.047 | 0.038 | 29 | 1.5 |
| 35 | 0.143 | 0.168 | 0.171 | 109 | 4.9 |
| 36 | 0.115 | 0.128 | 0.097 | 77 | 5.0 |
| 37 | 0.057 | 0.049 | 0.040 | 33 | 2.7 |
| 38 | 0.062 | 0.067 | 0.063 | 43 | 0.8 |
| 39 | 0.046 | 0.055 | 0.045 | 33 | 1.8 |
| 40 | 0.040 | 0.036 | 0.036 | 25 | 0.7 |
| 41 | 0.083 | 0.069 | 0.072 | 50 | 2.3 |

'wt' = untransformed wild type plants; '401' = transformed plants carrying a transfer DNA only comprising an expression cassette for the nptII seelectable marker gene, 'OD' = OD260 measurement, 'S.E.' = standard error.

TABLE 3

| Parental line | PCR positive for both gus gene and silencing construct | Partially silenced | Fully silenced |
|---|---|---|---|
| 374-18 | 25/50 (50%) | 24/25 (96%) | 0 |
| 717-54 | 35/50 (70%) | 28/35 (80%) | 3/35 (9%) |
| 773-4 | 23/50 (46%) | 0 | 23/23 (100%) |

SEQUENCES

| SEQ ID NO: | NAME (if any) | SEQUENCE |
|---|---|---|
| 1 | FMV promoter ('P1') | ATTTAGCAGCATTCCAGATTGGGTTCAATCAACAAGGTACGAGCCATATCA CTTTATTCAAATTGGTATCGCCAAAACCAAGAAGGAACTCCCATCCTCAAA GGTTTGTAAGGAAGAATTCTCAGTCAAAGCCTCAACAAGGTCAGGGTACA GAGTCTCCAAACCATTAGCCAAAAGCTACAGGAGATCAATGAAGAATCTTC AATCAAAGTAAACTACTGTTCCAGCACATGCATGCATGGTCAGTAAGTTTCA GAAAAAGACATCCACCGAAGACTTAAAGTTAGTGGGCATCTTTGAAAGTAA TCTTGTCAACATCGAGCAGCTGGCTTGTGGGGACCAGACAAAAAAGGAATG GTGCAGAATTGTTAGGCGCACCTACCAAAAGCATCTTTGCCTTTATTGCAA AGATAAAGCAGATTCCTCTAGTACAAGTGGGGAACAAAATAACGTGGAAAA GAGCTGTCCTGACAGCCCACTCACTAATGCGTATGACGAACGCAGTGACGA CCACAAAAGAATTCCCTCTATATAAGAAGGCATTCATTCCCATTTGAAGGA TCATCAGATACTCAACCAAT |
| 2 | 304-bp gus gene fragment | CAACGCGTAAACTCGACCCGACGCGTCCGATCACCTGCGTCAATGTAATGT TCTGCGACGCTCACACCGATACCATCAGCGATCTCTTTGATGTGCTGTGCC TGAACCGTTATTACGGATGGTATGTCCAAAGCGGCCATTTGGAAACGGCAG AGAAGGTACTGGAAAAGAACTTCTGGCCTGGCAGGAGAAACTGCATCAGC CGATTATCATCACCGAATACGGCGTGGATACGTTAGCCGGGCTGCACTCAA TGTACACCGACATGTGGAGTGAAGAGTATCAGTGTGCATGGCTGGATAT |
| 3 | terminator of pSIM718 | CGTTCAAACATTTGGCAATAAAGTTTCTTAAGATTGAATCCTGTTGCCGGT CTTGCGATGATTATCATATAATTTCTGTTGAATTACGTTAAGCATGTAATA ATTAACATGTAATGCATGACGTTATTTATGAGATGGGTTTTTATGATTAGA GTCCCGCAATTATACATTTAATACGCGATAGAAAACAAAATATAGCGCGCA AACTAGGATAAATTATCGCGCGCGGTGTCATCTATGTTACTAGATCGGG |

| SEQ ID NO: | NAME (if any) | SEQUENCE |
|---|---|---|
| 4 | intron of pSIM374 | GTGGTAACTTTTACTCATCTCCTCCAATTATTTCTGATTTCATGCATGTTT CCCTACATTCTATTATGAATCGTGTTATGGTGTATAAACGTTGTTTCATAT CTCATCTCATCTATTCTGATTTTGATTCTCTTGCCTACTGAATTTGACCCT ACTGTAATCGGTGATAAATGTGAATGCTTCCTCTTCTTCTTCTTCTTCTCA GAAATCAATTTCTGTTTTGTTTTTGTTCATCTGTAGCTTG |
| 5 | 35S promoter of cauliflower mosaic virus ('P2') | TAGCTTCATGGAGTCAAAGATTCAAATAGAGGACCTAACAGAACTCGCCGT AAAGACTGGCGAACAGTTCATACAGAGTCTCTTACGACTCAATGACAAGAA GAAAATCTTCGTCAACATGGTGGAGCACGACACACTTGTCTACTCCAAAAA TATCAAAGATACAGTCTCAGAAGACCAAAGGGCAATTGAGACTTTTCAACA AAGGGTAATATCCGGAAACCTCCTCGGATTCCATTGCCCAGCTATCTGTCA CTTTATTGTGAAGATAGTGGAAAAGGAAGGTGGCTCCTACAAATGCCATCA TTGCGATAAAGGAAAGGCCATCGTTGAAGATGCCTCTGCCGACAGTGGTCC CAAAGATGGACCCCCACCCACGAGGAGCATCGTGGAAAAAGAAGACGTTCC AACCACGTCTTCAAAGCAAGTGGATTGATGTGATATCTCCACTGACGTAAG GGATGACGCACAATCCCACTATCCTTCGCAAGACCCTTCCTCTATATAAGG AAGTTCATTTCATTTGGAGAGAACACGGGGGACTC |
| 6 | promoter of potato Ubiquitin- 7 gene | TCGAGCACATTGATTGAGTTTTATATGCAATATAGTAATAATAATAATATT TCTTATAAAGCAAGAGGTCAATTTTTTTTTATTATACCAACGTCACTAAAT TATATTTGATAATGTAAAACAATTCAATTTTACTTAAATATCATGAAATAA ACTATTTTTATAACCAAATTACTAAATTTTTCCAATAAAAAAAAGTCATTA AGAAGACATAAAATAAATTTGAGTAAAAAGAGTGAAGTCGACTGACTTTTT TTTTTTTATCATAAGAAAATAAATTATTAACTTTAACCTAATAAAACACTA ATATAATTTCATGGAATCTAATACTTACCTCTTAGAAATAAGAAAAGTGT TTCTAATAGACCCTCAATTTACATTAAATATTTTCAATCAAATTTAAATAA CAAATATCAATATGAGGTCAATAACAATATCAAAATAATATGAAAAAAGAG CAATACATAATATAAGAAAGAAGATTTAAGTGCGATTATCAAGGTAGTATT ATATCCTAATTTGCTAATATTTAAACTCTTATATTTAAGGTCATGTTCATG ATAAACTTGAAATGCGCTATATTAGAGCATATATTAAAATAAAAAAATACC TAAATAAAATTAAGTTATTTTTTAGTATATATTTTTTACATGACCTACAT TTTTCTGGGTTTTTCTAAAGGAGCGTGTAAGTGTCGACCTCATTCTCCTAA TTTTCCCCACCACATAAAAATTAAAAAGGAAAGGTAGCTTTTGCGTGTTGT TTTGGTACACTACACCTCATTATTACACGTGTCCTCATATAATTGGTTAAC CCTATGAGGCGGTTTCGTCTAGAGTCGGCCATGCCATCTATAAATGAAGC TTTCTGCACCTCATTTTTTTCATCTTCTATCTGATTTCTATTATAATTTCT CTCAATTGCCTTCAAATTTCTCTTTAAGGTTAGAAATCTTCTCTATTTTTG GTTTTTGTCTGTTTAGATTCTCGAATTAGCTAATCAGGTGCTGTTATAGCC CTTA |
| 7 | antisense gus gene fragment | CCTTCACCCGGTTGCCAGAGGTGCGGATTCACCACTTGCAAAGTCCCGCTA GTGCCTTGTCCAGTTGCAACCACCTGTTGATCCGCATCACGCAGTTCAACG CTGACATCACCATTGGCCACCACCTGCCAGTCAACAGACGCGTGGTTACAG TCTTGCGCGACATGCGTCACCA |
| 8 | PG primer | CAACGCGTAAACTCGACCCGACGCGTC |
| 9 | pIF primer | TTGTTTTTGTTCATCTGTAGCTTCTGC |
| 10 | PIR primer | TGGAGGAGATGAGTAAAAGTTACCACG |
| 11 | 300-bp 5' fragment of P1 promoter | ATTTAGCAGCATTCCAGATTGGGTTCAATCAACAAGGTACGAGCCATATCA CTTTATTCAAATTGGTATCGCCAAAACCAAGAAGGAACTCCCATCCTCAAA GGTTTGTAAGGAAGAATTCTCAGTCCAAAGCCTCAACAAGGTCAGGGTACA GAGTCTCCAAACCATTAGCCAAAAGCTACAGGAGATCAATGAAGAATCTTC AATCAAAGTAAACTACTGTTCCAGCACATGCATCATGGTCAGTAAGTTTCA GAAAAAGACATCCACCGAAGACTTAAAGTTAGTGGGCATCTTTGA |
| 12 | promoter of potato GBSS gene | GAACCATGCATCTCAATCTTAATACTAAAAAATGCAACAAAATTCTAGTGG AGGGACCAGTACCAGTACATTAGATATTATCTTTTATTACTATAATAATAT TTTAATTAACACGAGACATAGGAATGTCAAGTGGTAGCGGTAGGAGGGAGT TGGTTCAGTTTTTTAGATACTAGGAGACAGAACCGGAGGGGCCCATTGCAA GGCCCAAGTTGAAGTCCAGCCGTGAATCAACAAAGAGAGGGCCCATAATAC TGTCGATGAGCATTTCCCTATAATACAGTGTCCACAGTTGCCTTCCGCTAA GGGATAGCCACCCGCTATTCTCTTGACACGTGTCACTGAAACCTGCTACAA ATAAGGCAGGCACCTCCTCATTCTCACACTCACTCACTCACACAGCTCAAC AAGTGGTAACTTTTACTCATCTCCTCCAATTATTTCTGATTTCATGCATGT TCCCTACATTCTATTATGAATCGTGTTATGGTGTATAAACGTTGTTTCAT |

| SEQ ID NO: | NAME (if any) | SEQUENCE |
|---|---|---|
| | | ATCTCATCTCATCTATTCTGATTTTGATTCTCTTGCCTACTGAATTTGACC<br>CTACTGTAATCGGTGATAAATGTGAATGCTTCCTCTTCTTCTTCTTCTTCT<br>CAGAAATCAATTTCTGTTTTGTTTTTGTTCATCTGTAGCTTGGTAG |
| 13 | promoter of potato AGP gene | CCGCAGTGTGCCAGGGCTGTCGGCAGATGGACATAAATGGCACACCGCTCG<br>GCTCGTGGAAAGAGTATGGTCAGTTTCATTGATAAGTATTTACTCGTATTC<br>GGTGTTTACATCAAGTTAATATGTTCAAACACATGTGATATCATACATCCA<br>TTAGTTAAGTATAAATGCCAACTTTTTACTTGAATCGCCGAATAAATTTAC<br>TTACGTCCAATATTTAGTTTTGTGTGTCAAACATATCATGCACTATTTGAT<br>TAAGAATAAATAAACGATGTGTAATTTGAAAACCAATTAGAAAAGAAGTAT<br>GACGGGATTGATGTTCTGTGAAATCACTGGTAAATTGGACGGACGATGAAA<br>TTTGATCGTCCATTTAAGCATAGCAACATGGGTCTTTAGTCATCATCATTA<br>TGTTATAATTATTTTCTTGAAACTTGATACACCAACTTTCATTGGGAAAGT<br>GACAGCATAGTATAAACTATAATATCAATTCTGGCAATTTCGAATTATTCC<br>AAATCTCTTTTGTCATTTCATTTCCTCCCCTATGTCTGCAAGTACCAATTA<br>TTTAAGTACAAAAAATCTTGATTAAACAATTTATTTTCTCACTAATAATCA<br>CATTTAATCATCAACGGTTCATACACGTCTGTCACTCTTTTTTTATTCTCT<br>CAAGCGCATGTGATCATACCAATTATTTAAATACAAAAAATCTTGATTAAA<br>CAATTCAGTTTCTCACTAATAATCACATTTAATCATCAACGGTTCATACAC<br>ATCCGTCACTCTTTTTTTATTCTCTCAAGCGCATGTGATCATACCAATTAT<br>TTAAATACAAAAAATCTTGATTAAACAATTCATTTTCTCACTAATAATCAC<br>ATTTAATCATCAACGGTTTATACACGTCCGCCACTCTTTTTTTATTCTCTC<br>AAGCGTATGTGATCATATCTAACTCTCGTGCAAACAAGTGAAATGACGTTC<br>ACTAATAAATAATCTTTTGAATACTTTGTTCAGTTTAATTTATTTAATTTG<br>ATAA |
| 14 | 154-bp trailer of potato PPO gene | TTAGTCTCTATTGAATCTGCTGAGATTACACTTTGATGGATGATGCTCTGT<br>TTTTGTTTTCTTGTTCTGTTTTTTCCTCTGTTGAAATCAGCTTTGTTGCTT<br>GATTTCATTGAAGTTGTTATTCAAGAATAAATCAGTTACAATTATGTTTGG<br>G |
| 15 | intron of potato ubiquitin-7 gene | GTTAGAAATCTTCTCTATTTTTGGTTTTTGTCTGTTTAGATTCTCGAATTA<br>GCTAATCAGGTGCTGTTATAGCCCTTAATTTTGAGTTTTTTTTCGGTTGTT<br>TTGATGGAAAAGGCCTAAAATTTGAGTTTTTTTACGTTGGTTTGATGGAAA<br>AGGCCTACAATTGGAGTTTTCCCCGTTGTTTTGATGAAAAAGCCCCTAGTT<br>TGAGATTTTTTTTCTGTCGATTCGATTCTAAAGGTTTAAAATTAGAGTTTT<br>TACATTTGTTTGATGAAAAAGGCCTTAAATTTGAGTTTTTCCGGTTGATTT<br>GATGAAAAAGCCCTAGAATTTGTGTTTTTTCGTCGGTTTGATTCTGAAGGC<br>CTAAAATTTGAGTTTCTCCGGCTGTTTTGATGAAAAAGCCCTAAATTTGAG<br>TTTCTCCGGCTGTTTTGATGAAAAAGCCCTAAATTTGAGTTTTTTCCCCGT<br>GTTTTTAGATTGTTTGGTTTTAATTCTCGAATCAGCTAATCAGGGAGTGTGA<br>AAAGCCCTAAATTTGAGTTTTTTCGTTGTTCTGATTGTTGTTTTTATGA<br>ATTTGCAG |
| 16 | fragment of tobacco PPO gene | TTAGTCTCTATTGAATCTGCTGAGATTACACTTTGATGGATGATGCTCTGT<br>TTTTGTTTTCTTGTTCTGTTTTTTCCTCTGTTGAAATCAGCTTTGTTGCTT<br>GATTTCATTGAAGTTGTTATTCAAGAATAAATCAGTTACAATTATGTTTGG<br>G |
| 17 | transfer DNA of Russet Boise II | TGGCAGGATATATACCGGTGTAAACGAAGTGTGTGGTTGATCCAAAATC<br>TATCGTACCTTTAGAAAGTGTAGCTATGAAGGATAGTCTCACTTATGAAGA<br>ACTACCTATTGAGATTCTTGATCGTCAGGTCCGAAGGTTGAGAAAAATAGA<br>AGTCGCTTCAGTTACGGCTTTGTGGAGGAGTAAGGGTACCGAACCATGCAT<br>CTCAATCTTAATACTAAAAAATGCAACAAAATTCTAGTGGAGGGACCAGTA<br>CCAGTACATTAGATATTATCTTTTATTACTATAATAATATTTTAATTAACA<br>CGAGACATAGGAATGTCAAGTGGTAGCGGTAGGAGGGAGTTGGTTCAGTTT<br>TTTAGATACTAGGAGACAGAACCGGAGGGGCCCATTGCAAGGCCCAAGTTG<br>AAGTCCAGCCGTGAATCAACAAAGAGAGGGCCCATAATACTGTCGATGAGC<br>ATTTCCCTATAATACAGTGTCCACAGTTGCCTTCCGCTAAGGGATAGCCAC<br>CCGCTATTCTCTTGACACGTGTCACTGAAACCTGCTACAAATAAGGCAGGC<br>ACCTCCTCATTCTCACACTCACTCACTCACACAGCTCAACAAGTGGTAACT<br>TTTACTCATCTCCTCCAATTATTTCTGATTTCATGCATGTTTCCCTACATT<br>CTATTATGAATCGTGTTATGGTGTATAAACGTTGTTTCATATCTCATCTCA<br>TCTATTCTGATTTTGATTCTCTTGCCTACTGAATTTGACCCTACTGTAATC<br>GGTGATAAATGTGAATGCTTCCTCTTCTTCTTCTTCTTCTCAGAAATCAAT<br>TTCTGTTTTGTTTTGTTCATCTGTAGCTTGGTAGATTCCCCTTTTTGTAG<br>ACCACACATCACGGATCCCCCAAACATAATTGTAACTGATTTATTCTTGAA<br>TAACAACTTCAATGAAATCAAGCAACAAAGCTGATTTCAACATGAAAAAAC<br>AGAACAAGAAAACGAAAACAGAGCATCATCCATCAAAGTGTAATCTCAGCA<br>GATTCAATAGAGACTAACTCGAGGTGCTCTCTATGCAAATCTAGCTTTTCG<br>AATGAGAGTGATAAGAGAGTGAGGATTGTGAATTATTTTATTGATGAAGAT<br>TGGAGAAGTCAATTATTGATTCACACACAGGAATTAAGTGTGTTGTGTTGC<br>GTCCTCTTGTGGAAATTAAATGTCACCCTTTTTTTATTTATCAATAAAAGC |

-continued

SEQUENCES

| SEQ ID NO: | NAME (if any) | SEQUENCE |
|---|---|---|
| | | ACGAAAATCTCCTGCACTACTCCCCTGCACTCTCTTATATTTGTCCATTTC<br>CCACAAATCCCTAACTTAATTACTTACCCACACTCAAGCTTCAACACTGTT<br>GAGGTTAGGAATCCCTGGTACAGCAAGTTATTCCCTAAGGAATTACTCATA<br>TCCTCCCACTGGCTTAATTCACTCAAGTTCAGCTAGAAACGTCGATTTCTA<br>GTGAAGTAACGAGGAAATTAGCGAAGAAGCGTCGAGAAATTCGATGAAGAT<br>GAATTCACGAAGCAAAATGAAGATTGGAGCAGAGAGTATGGGGATTGGAGA<br>GTGGAAAGTGGTAGTGAAATAAGGTCCGCGGGTTAAATTCATGATTTTATG<br>AACTCAATAGCTTTTCATAATGAGCAATATTATCTTTCTTCAGTAGCAAAT<br>CCACATGCTCTTATGCTCGCTGAAATAGTTTTGGCCGTGGAGTTTCACCAT<br>CTATGTTTACAATTGATTCTTGTAGCTGCAGACCTTATTTCACTACCACTT<br>TCCACTCTCCAATCCCCATACTCTCTGCTCCAATCTTCATTTTGCTTCGTG<br>AATTCATCTTCATCGAATTTCTCGACGCTTCTTCGCTAATTTCCTCGTTAC<br>TTCACTAGAAATCGACGTTTCTAGCTGAACTTGAGTGAATTAAGCCAGTGG<br>GAGGATATGAGTAATTCCTTAGGGAATAACTTGCTGTACCAGGGATTCCTA<br>ACCTCAACAGTGTTGAAGCTTGAGTGTGGGTAAGTAATTAAGTTAGGGATT<br>TGTGGGAAATGGACAAATATAAGAGAGTGCAGGGGAGTAGTGCAGGAGATT<br>TTCGTGCTTTTATTGATAAATAAAAAAGGGTGACATTTAATTTCCACAAG<br>AGGACGCAACACAACACACTTAATTCCTGTGTGTGAATCAATAATTGACTT<br>CTCCAATCTTCATCAATAAAATAATTCACAATCCTCACTCTCTTATCACTC<br>TCATTCGAAAAGCTAGATTTGCATAGAGAGCACCTCGAGTTAGTCTCTATT<br>GAATCTGCTGAGATTACACTTTGATGGATGATGCTCTGTTTTCGTTTTCTT<br>GTTCTGTTTTTTCATGTTGAAATCAGCTTTGTTGCTTGATTTCATTGAAGT<br>TGTTATTCAAGAATAAATCAGTTACAATTATGTTTGGGTCTAGAGTGATGT<br>GTGGTCTACAAAAAGGGGAATCTACCAAGCTACAGATGAACAAAAACAAAA<br>CAGAAATTGATTTCTGAGAAGAAGAAGAAGAAGAGGAAGCATTCACATTTA<br>TCACCGATTACAGTAGGGTCAAATTCAGTAGGCAAGAGAATCAAAATCAGA<br>ATAGATGAGATGAGATATGAAACAACGTTTATACACCATAACACGATTCAT<br>AATAGAATGTAGGGAAACATGCATGAAATCAGAAATAATTGGAGGAGATGA<br>GTAAAAGTTACCACTTGTTGAGCTGTGTGAGTGAGTGAGTGTGAGAATGAG<br>GAGGTGCCTGCCTTATTTGTAGCAGGTTTCAGTGACACGTGTCAAGAGAAT<br>AGCGGGTGGCTATCCCTTAGCGGAAGGCAACTGTGGACACTGTATTATAGG<br>GAAATGCTCATCGACAGTATTATGGGCCCTCTCTTTGTTGATTCACGGCTG<br>GACTTCAACTTGGGCCTTGCAATGGGCCCCTCCGGTTCTGTCTCCTAGTAT<br>CTAAAAAACTGAACCAACTCCCTCCTACCGCTACCACTTGACATTCCTATG<br>TCTCGTGTTAATTAAAATATTATTATAGTAATAAAAGATAATATCTAATGT<br>ACTGGTACTGGTCCCTCCACTAGAATTTTGTTGCATTTTTTAGTATTAAGA<br>TTGAGATGCATGGTTCGAGCTCCTTCAACATGTTATAAACTTCACATATTC<br>AGTTGGGAATAGGCTTTATAATGAGTTGGACTACGTTATGTCCCCCTCAAG<br>TCCCAGAATTATGTGCCCCCGTATGTTATAAGTCCCCTCTGCGGGCATCAA<br>TTTAGTGATCACGCCAGACATGCCTCTATACCTCGGCCAGGATATATTTGT<br>TGGTAATG |
| 18 | fragment of trailer of the *Solanum verrucosum* tuber-expressed PPO gene | CCCAAACATAATTGTAACTGATTTATTCTTGAATAACAACTTCAATGAAAT<br>CAAGCAACAAAGCTGATTTCAACATGAAAAAACAGAACAAGAAAACGAAAA<br>CAGAGCATCATCCATCAAAGTGTAATCTCAGCAGATTCAATAGAGACTAA |
| 19 | fragment of phosphorylase leader | GTGCTCTCTATGCAAATCTAGCTTTTCGAATGAGAGTGATAAGAGAGTGAG<br>GATTGTGAATTATTTTATTGATGAAGATTGGAGAAGTCAATTATTGATTCA<br>CACACAGGAATTAAGTGTGTTGTGTTGCGTCCTCTTGTGGAAATTAAATGT<br>CACCCTTTTTTTATTTATCAATAAAAGCACGAAAATCTCCTGCACTACTCC<br>CCTGCACTCTCTTATATTTGTCCATTTCCCACAAATCCCTAACTTAATTAC<br>TTACCCACACTC |
| 20 | fragment of R1 leader | CAACACTGTTGAGGTTAGGAATCCCTGGTACAGCAAGTTATTCCCTAAGGA<br>ATTACTCATATCCTCCCACTGGCTTAATTCACTCAAGTTCAGCTAGAAACG<br>TCGATTTCTAGTGAAGTAACGAGGAAATTAGCGAAGAAGCGTCGAGAAATT<br>CGATGAAGATGAATTCACGAAGCAAAATGAAGATTGGAGCAGAGAGTATGG<br>GGATTGGAGAGTGGAAAGTGGTAGTGAAATAAGGT |
| 21 | non-functional P1 promoter without TATA box of pSIM788 | ATTTAGCAGCATTCCAGATTGGGTTCAATCAACAAGGTACGAGCCATATCA<br>CTTTATTCAAATTGGTATCGCCAAAACCAAGAAGGAACTCCCATCCTCAAA<br>GGTTTGTAAGGAAGAATTCTCAGTCCAAAGCCTCAACAAGGTCAGGGTACA<br>GAGTCTCCAAACCATTAGCCAAAAGCTACAGGAGATCAATGAAGAATCTTC<br>AATCAAAGTAAACTACTGTTCCAGCACATGCATCATGGTCAGTAAGTTTCA<br>GAAAAAGACATCCACCGAAGACTTAAAGTTAGTGGGCATCTTTGAAAGTAA<br>TCTTGTCAACATCGAGCAGCTGGCTTGTGGGGACCAGACAAAAAAGGAATG<br>GTGCAGAATTGTTAGGCGCACCTACCAAAAGCATCTTTGCCTTTATTGCAA |

| SEQ ID NO: | NAME (if any) | SEQUENCE |
|---|---|---|
| | | AGATAAAGCAGATTCCTCTAGTACAAGTGGGGAACAAAATAACGTGGAAAA GAGCTGTCCTGACAGCCCACTCACTAATGCGTATGACGAACGCAGTGACGA CCACAAAAGA |
| 22 | promoter of potato R1 gene | TTCAAATTTCATTTGTGTCATATAAATTGAGACATATAATTGTCGGCACAT GCTCATGTATCCAAACAAGGATAATTTGATCATCTATTCTTATATATTTGA AAATTACGATAATAATACTTTAAATCACAATAATTAACAAGTTAAAATATT TAAAAGTCATATAAAAAATTAATTGACTCTCAAAATTCTGTAAGTACTATA AATTAAAATAAATAACAACTTAAGAATTTCAAAGTCATAAAAAATTTGGTG GCTCTCTAAAATATATCAATGTCACATAAAAAGTAACATATATTATTCAGA AATTACGTAAAAGATACCACAAATTACAATAATTAACAACTTGAAATATTT AAAATACATAAAAATAATTAATTTTAGAAATTCCAGGCGTGCCACATAAAT TGGGACAACGAAATAATATATACTATTATTTTAAAATTATGTAAAAAAATA ATTCTAAATCATGATAATTAATAACTTAAAATATTATTAAAAATCATATAA AAATTTAAATAATTGCTCAGGTTTCAGCCGTATTACATAAATTAGGATAAA AAATAATATATATTGGGCCCCGTGCTGGCACGGGGGCCCGTATCTAGTTTA TATAATAAATATCGTTTCTAGTCTATCTCTTCTGATGCTAAATAAAGTCTG TGATTATCTTTTAATTTTTTCTACTCAGCATGGGGTGCCGTATCTAGTTTA TATAATAAATATCGTTTCTAGTCTATCTCTTCTGATGCTAAATAAAGTCAG TGATTATTTTTAATTTTTTCTACTAGGTAATGTAAAATTCTTATGTTAAC CAAATAAATTGAGACAAATTAATTCAGTTAACCAGAGTTAAGAGTAAAGTA CTATTGCAAGAAAATATCAAAGGCAAAGAAAAGATCATGAAAGAAAATAT CAAAGAAAAAGAAGAGGTTACAATCAAACTCCCATAAAACTCCAAAAATAA ACATTCAAATTGCAAAAACATCCAATCAAATTGCTCTACTTCACGGGGCCC ACGC |
| 23 | 342-bp fragment of promoter of R1 gene | AAAATTCTTATGTTAACCAAATAAATTGAGACAAATTAATTCAGTTAACCA GAGTTAAGAGTAAAGTACTATTGCAAGAAAATATCAAAGGCAAAGAAAAG ATCATGAAAGAAAATATCAAAGAAAAGAAGAGGTTACAATCAAACTCCCA TAAAACTCCAAAATAAACATTCAAATTGCAAAAACATCCAATCAAATTGC TCTACTTCACGGGGCCCACGCCGGCTGCATCTCAAACTTTCCCACGTGACA TCCCATAACAAATCACCACCGTAACCCTTCTCAAAACTCGACACCTCACTC TTTTTCTCTATATTACAATAAAAAATATACGTGTCC |
| 24 | 151-bp fragment of promoter of R1 gene | CATTCAAATTGCAAAAACATCCAATCAAATTGCTCTACTTCACGGGGCCCA CGCCGGCTGCATCTCAAACTTTCCCACGTGACATCCCATAACAAATCACCA CCGTAACCCTTCTCAAAACTCGACACCTCACTCTTTTTCTCTATATTAC |
| 25 | promoter of potato tuber-expressed PPO gene | TAATATAACATACCATGGGTGGAGCTAGAAGTCTGATTACAAATTTCGTCA AATTCAACAATATTTGCTTAAATAATATATTTGTATAGTAATTTTTTTTAC AAAATATATACAAATTTAGGTCAAGGATTCAGTTATTAACCCTTTAAAATC GTGTCATAAAATTCAATGTTAAAATTCTGACTTTCCCCGTGCTTAACATTA CTTATCAAATTTATGTTTCTGTGTAGAAAAGTACTAGTACTACTCTTTGAC TCGTCTAGACGTCTACTATAGATCTCCTTAGATTAAAAACTCCAGTTTTAA TATTTTCCTCACAATTATTATTCTTAATCTACCACCTACCGGAGTCACAAA TATATTAAATGAAAATATTCTATCTATTAATTTATGATCTACCTATTGATA ATTTGTAATCTAGTCAAAATGATGGCAAAAAAAATATAATATCTAGACTGA AGTTCTTAGTCAATAGCGTAAATGAAAGAAAAAAAAAAAAGCTCAAGAAGA AACATGATATCTTTGTTGCTCTGATTCGTAAAAAAAAAACATAGTAACTT CATAAAATATCTTATCCTTTGGACAGAGCGATGAAAAAAATATATTACTAG TAATACTGAGATTAGTTACCTGAGACTATTTCCTATCTTCTGTTTTGATTT GATTTATTAAGGAAAATTATGTTTCAACGGCCATGCTTATCCATGCATTAT TAATGATCAATATATTACTAAATGCTATTACTATAGGTTGCTTATATGTTC TGTAATACTGAATATGATGTATAACTAATACATACATTAAATTCTCTAATA AATCTATCAACGAAGCCTAAGAGATTAACAAATACTACTATTATCCAGAC TAAGTTATTTTTCTGTTTACTACAGATCCTTCCAAGAACAAAAACTTAATA ATTGTATGGCTGCTATACATAATTCCCCACCTACCGCTTCCTGGAATAATT GATATGGAAGCCGCCTCTAAAATTGAATAATTATACTGTTTTACATATTAT ATAA |
| 26 | 200-bp fragment of promoter of PPO gene | AAGTTATTTTTCTGTTTACTACAGATCCTTCCAAGAACAAAAACTTAATAA TTGTATGGCTGCTATACATAATTCCCCACCTACCGCTTCCTGGAATAATTG ATATGGAAGCCGCCTCTAAAATTGAATAATTATACTGTTTTACATATTATA TAAAGCAAGGTATAGCCCAATGAATTTTCATTCAAAAGCTAGCAATA |
| 27 | 460-bp fragment of promoter | CTAGTAATACTGAGATTAGTTACCTGAGACTATTTCCTATCTTCTGTTTTG ATTTGATTTATTAAGGAAAATTATGTTTCAACGGCCATGCTTATCCATGCA TTATTAATGATCAATATATTACTAAATGCTATTACTATAGGTTGCTTATAT GTTCTGTAATACTGAATATGATGTATAACTAATACATACATTAAATTCTCT |

| SEQ ID NO: | NAME (if any) | SEQUENCE |
|---|---|---|
| | of PPO gene | AATAAATCTATCAACAGAAGCCTAAGAGATTAACAAATACTACTATTATCC AGACTAAGTTATTTTTCTGTTTACTACAGATCCTTCCAAGAACAAAAACTT AATAATTGTATGGCTGCTATACATAATTCCCCACCTACCGCTTCCTGGAAT AATTGATATGGAAGCCGCCTCTAAAATTGAATAATTATACTGTTTTACATA TTATATAAAGCAAGGTATAGCCCAATGAATTTTCATTCAAAAGCTAGCAAT A |
| 28 | promoter of *Brassica* Fad2 gene | ATTGAGCTTGAAGGAACATTCGAGCAGATAAACGAAGCGAGCGCAATGGTT AGAGAGCTGATTGGGAGGCTTAATTCCGCATCTAGGAGACCACCTGGTGGC GGTGGTGGCGGGGGTGGGCTTGGTTCTGAAGGGAAACCACATCCAGGAAGC AACTTCAAGACGAAGATGTGTGAGAGATTCTCTAAAGGAAGCTGTACATTT GGTGATAGATGTCACTTTGCTCACGGGGAAGCAGAGCTACGCAGGTCATGA ATTGCGCCTAGAGTTACTGGTGAAACAAGTCTCTTTCATTTGTTGTGGTGA TTCCTAATATCATCTTCTCCTACTTGTTTTTAGTTGTCTTCGTTTTTTGAA ACTACAATGTTTAGTTTTCATTGTCAGTGTAAGTTTTCCCCATTTGGTGTT TTTTTAGAATCTAGTTTGAATTTGAGATGGGGCAAGCTTGATGAATGATTG GCAAAACAGTGGTTAGGATTTGTGTGCTGTCTCACTTAATATTTCATGTT TTATCTACTTTATTTTGGTCAGCAAGTTGATGTGTTTCTCTGATGTGTGTG TGATTATCAGCTTAGATTATTTTGTGAGTATGCTAGACTGTATAACTAATC GTTGTCGATGTTATAGTTCTCTTATAATGTTTGATAGACTATATAACTAAA AATTCATGTTATTAATAGCCGTCGCTGATAGTAACAGCTGAATAAATGAAA TGAAATCATGGTAGGTGATGATCTTTAAAGAATGTTAAAAATAATGTGTCG TTATAAGCGGTAATGCATAGAAAAACTCTAATCATCTTAACATAAGAGAGA GCGATAGCTTTAATAAAGTACTTAAATTAATTACTAGTCGGCAGTCGCTGC CTACTTGTGTACCACCTAAATTAATTTATTATAATATGACGAATCTCCA AAGTACATCACACACACTCGGGGCTATTCACGTGATCTCAACCACAATGTC TGCAGATATTTTTTAAGTTTTCTTCTCACATGGGAGAAGAAGAAGCCAAG CACG |
| 29 | 441-bp fragment of Fad2 promoter | CCGGCTACCACTAACTTCTACAGTTCTACTTGTGAGTCGGCAAGGACGTTT CCTCATATTAAAGTAAAGACATCAAATACCATAATCTTAATGCTAATTAAC GTAACGGATGAGTTCTATAACATAACCCAAACTAGTCTTTGTGAACATTAG GATTGGGTAAACCAATATTTACATTTTAAAACAAAATACAAAAAGAAACG TGATAAACTTTATAAAAGCAATTATATGATCACGGCATCTTTTTCACTTTT CCGTAAATATATATAAGTGGTGTAAATATCAGATATTTGGAGTAGAAAAAA AAAAAAAGAAAAAAGAAATATGAAGAGAGGAAATAATGGAGGGGCCCACTT GTAAAAAGAAAGAAAAGAGATGTCACTCAATCGTCTCACACGGGCCCCCG TCAATTTAAACGGCCTGCCTTCTGCCCAATCGC |
| 30 | seed-specific promoter of napin gene | AAGCTTTCTTCATCGGTGATTGATTCCTTTAAAGACTTATGTTTCTTATCT TGCTTCTGAGGCAAGTATTCAGTTACCACTTATATTCTGGACTTTCTGACT GCATCCTCATTTTTCCAACATTTTAAATTTCACTATTGGCTGAATGCTTCT TCTTTGAGGAAGAAACAATTCAGATGGCAGAAATGTATCAACCAATGCATA TATACAAATGTACCTCTTGTTCTCAAAACATCTATCGGATGGTTCATTTG CTTTGTCATCCAATTAGTGACTACTTTATATTATTCACTCCTCTTTATTAC TATTTTCATGCGAGGTTGCCATGTACATTATATTTGTAAGGATTGACGCTA TTGAGCGTTTTTCTTCAATTTTCTTTATTTTAGACATGGGTATGAAATGGT TGTTAGAGTTGGGTTGAATGAGATATACGTTCAAGTGAATGGCATACCGTT CTCGAGTAAGGATGACCTACCCATTCTTGAGACAAATGTTACATTTTAGTA TCAGAGTAAAATGTGTACCTATAACTCAAATTCGATTGACATGTATCCATT CAACATAAAATTAAACCAGCCTGCACCTGCATCCACATTTCAAGTATTTTC AAACCGTTCGGCTCCTATCCACCGGGTGTAACAAGACGGATTCCGAATTTG GAAGATTTTGACTCAAATTCCCAATTTATATTGACCGTGACTAAATCAACT TTAACTTCTATAATTCTGATTAAGCTCCCAATTTATATTCCCAACGGCACT ACCTCCAAAATTTATAGACTCTCATCCCCTTTTAAACCAACTTAGTAAACG TTTTTTTTTTTAATTTTATGAAGTTAAGTTTTTACCTTGTTTTTAAAAAGA ATCGTTCATAAGATGCCATGCCAGAACATTAGCTACACGTTACACATAGCA TGCAGCCGCGGAGAATTGTTTTTCTTCGCCACTTGTCACTCCCTTCAAACA CCTAAGAGCTTCTCTCTCACAGCACACACATACAATCACATGCGTGCATGC ATTA |
| 31 | seed-specific promoter of *Brassica napus* | CTGCACGTACAAAGAGGAGCTCTACTTAGTTTATGACTTTATGCCCAGTGG AAGCCTTGACAAGTACCTCTACACCGAATCAGATCAAGAATATATGAAGTT CACAAGAAAAATCTTAGTATTTGTTTACTCTATCTTTCTATGTAAATGTGT TTTTGCTTTTCAAAAAAGAGCTTTGAGAAAAATTAAAGAAGATAACTTGTC TTAACCTATTTTGGTTCGGGTTTTGCGGAGAACTTTTGAAAATAATGACA ACTAGGTGTTTTGCCCTCGATGCGGATTTAAACATTTTCATAATTTTTGAA AAGTTCTTTGTACACTATATTCATTATACTAAAATAAATCTTAAAATAATT TAATATTATATTTTAAATTATATAATTAAAAAACAATTATTTGATTAATAT TTAATTATATAATTTATGTTTTAACTTTTTACTAAATACTTTTTCAGATAA CAATACAATACATATATATAGAAATTATCTTTTTTTAAATTATATTTTA GATCTTGGATAATTTAATATTATATTTTATTATATAATTAAGAATTTTAT TTGATTAATATTTAGTTATATAATTCATGTTTTAAACTTTATATATATAAT TCATGTTTTTAACTTTTTACTAAAATACTTTTTCAGATAACAATACAATAT |

| SEQ ID NO: | NAME (if any) | SEQUENCE |
|---|---|---|
| | | ATACATAAATTATCTCTTTTTAAAATTATATTTTCAGATTTTGGATAATGC TTACTATTATTAATTTTAATCAATTATCTAATCAAATAAATTAAAATTTTG TTTTATAGGATATAAACGATATTAATCATTCTAATTTTTAACGTGAGAGTT CGATTCCAAAAATTTACTTCGCAAATAATAGTATATATCTAGCTTATTAGG GCTTTAAAAGGTTTAGGTTTCTTTACGCTTTAATTGTTTTTTTTAACTATA ATTGTAAACGTGTTAAACATAACTAATCAGTGTTAAAACTTGCTTTATTTT ATTTTTCCAACTTTTAGATTAAAGCATAAAGTGTTACCATAAAAAAGAAGA TTAAAGCATAAAGAGATATCATTTGGTATAATATTTATGCCAACGTATAAT TTGTTTTTATCTTTTATGCAAACGCATACACATGTGGACTTGAAAGAAACG ACAATGAGGACACTTAACACAAACTCCCAAAATGTCACTTAAAGCTATAGT TCTGTCACGGTCTCTCAATGGAAAATCGTGGTGCTATCAATGAAAAAACGT TGTGCTGAAACTGGCAGAGCACAAAACTATAGTCTAAAAAGGATTGAATGA AGCAAAAAATGCAAGAACCAAAGGCACAACGATTCTCACATTTGAATGATA TTAGAAATATTAGTTTCATTTGCCAAGTGGACACATCCACGTGGTAGAGGA GCCATGCCACTTGTCTCTTTCGTGGGTTCTCACGCCCGAGTTACATTTGAA AATTACAAAATAAAAGAACATTTTGTATATGTATTGACATTTTTACCCTTG CATATACATGTGTTTAGATCTAAATTCACAACTAATCCATCTCTTATCATT TTTAGTTAACTAAGAGCATCAATGTTAACCATGATTCTAATTTGAAATTAA TTCATGATTTGATATTTTATTATTTTATTTTTATATTTTTGGTTAAAAAC AGACTCTTATATCTTTTATTTAAGAGATAGTTCTTAATTTTCTTAATTAAA AGTTAAGAAACGGTTCTTAACCAAATGTAAAAACCATATTGTAAGAGCTCG GATTTATTATGATCTAAGGAACTCACGAGTCAATTCACCTAATCAAATCTA AAATATAGTAATTATAGCTTTACCGACATGTGATACTGCCAAAAATAATAA ATAATATATAGACACAAGAAGGATGTGATAGTGAGGAATCTGGAGGGCATT TTAGAACTGATGCTCGATTAAAAACAGAAAATAATCTTCAAAATTTTAATT TACACGATAGATGACGTCATTTTTCCATTTGTTTTGTTAATTAGTTATTTA TTTCCTTCTCTCTTTCCTCCGAGTGTAGACTCTTCCCTCAAACCGCTGT TTCTCATAACCATATTCTCTTTCTGTGGACGAAACTCAACCTTAAGAGACC AGAGAGAGCATTAGCCTAGAGAGCTCGTCGTGTCTGAAAGAACATCAA ACCTCGTATCAAAAAAAAGAAA |
| 32 | promoter of soybean Fad12 gene | CAGAAAAAGGGAATAGTTTGGATAAAATAGATTTTAGGTCTCTCAATTCCT AGTCAAAATTAGTCTCAATCATTATGCTTTAAAAATGATGATTTTGACACT TGGGAGATAACAATATTTCTTAAAGTTTGATTCTCAAGTTNGTATATATGA AATAGTGTGTTGGGAGAAGTAAACTCTTAAAATAAATTTTTATATTTTAGA GATGATTCTCTCATTCTTATGAAGGAGATATACTAGAAAAAAAATGATTTT TATTTTTTATTTTTATTATGAAACTTAAGAATTAAGATACCAGGATGAG GGACAAAAGTCATTAATTATTAAAAAAAAATACAAGAATCAAGATTATTAT TTTTAAAATATAAAAAAACTAATTTTGATATATAAAGAAATCCAGGGGAT ATAATACACACTCTATCCCAAATATTTGGTTAAACCCCCAGGGGCCCAATG TTTCGTCTTTCCTCAACAGTATAAATTGCTAATGATATTATTTGTCTTGAA TTGGTTCCTGTGGCTAGCATATCTCTGCAACTTGTGCAACCATTTGGTAAT TCAATTAAGAATATATAATATACTTTAAATTTACTAGGATGCATAAAAAAC CCTGTGACTTGTCTGACCAAGACTTGCCAAATTTTTTTATCATGCATTACA AAAACCAGCCATTTGTTTTTATTTTTTGGATTTCTATTCTTTCCAAATGAA GGCCTAACAGATAAATTGCATGTCTAATTTCCCCTTGTTATTAGAGAAATA AGAAATTATAAGCTTTTGCTTTGACTTTTGAACATATTTTACACTCTTTGC AGGTTGCTTTTTATCTTGGAAGACCAGAGGAGTCAAAATAACAGTGTCGCG GTAAGTAAGTGCTCGACATTCTGGAATAGTCTCTTATTGCGTATTGTGCCA TCATTTTGAGGCCTTGTGGCTTGCATCACCATTGAAAGAAATTAGTTTGA TGGTTAAAATGGTATACCTTTTGTCTTCATTATTACTCGAATTACATTTAG AAAG |
| 33 | promoter of alfalfa Comt gene | AAATGAAAGAGAGTTAAGGATTGAAATGAAACTGGTAAAAAACAGCTTATT TTAAAACATCTTATTCAAACAACTTATTTTATTTAAAACAATTTATTTTA TTCAAAACATGTTTTGAATAAGTTGTTTTTTGAAAATAAGCTGTTTTGAAT AAGCTGTTTTTAAAATAAGGTGTTTTTCATAAAATAAGTTGTTTTTTGTTAA AATAAGTTGTTTTTCAAATAAGCTGTTTTGAATAAGCTGTTTTTTTTAA ATAAGTTGTTTTGAATAAGCTGTTTTTTTTAAATAAGTGTTTTTTTAAAT AAGCTGTTTTGAATAAGTTGTTTTAAATAAGGTGTTTGCATAAAATAAG CTGTTTTGAATAAGTTGTTTTGAATAAGTTGTTTTGAATAAGCTGTTTTTT TTAAAAATAAATTGTTTTCATAAAATAAGCTGTTTTTAAAATAAGGTGTTT TGTATAAATAAGCTTTTAAAATAAGCTATTCAAATAAGTTGTTTTTTTGG AAAGATCCAACAAAGAGTTCAAGTGGTTTCTTTAAAATAAAATAAAAAGTT CAAGTGGTTTGGTTCGGTTCAAACGGTTCGGTTCGGTTCAAGATGGTTCGG TTATGGTTCAAGAACTGTTAATAAATTAACGGTTCGGTTCGTGAACCATTA TAACGATTCGGTTATTTTGGTTCGGTTCGGTTCGCGGTTCGGTTCGGT TCATGGTTCTTTTTGCCCACCCCTAAAGAAAATAAATGAATGGTGGTTGAG TATTCTTAAAATGATTTGTTTTCTAGAATAAAGAGTTAATAAGGGGTCAA AAGAGCAACCATCTAAGGTAAACTCTCACATTTAGAGTTGATGCGGTTAAA ATTTGGATATAACACTTTTGTTGACCAAAATGTCTCTTATGAATAAGACTG AAAGAGTAATAATTTAAAAAAAAAAAATCCGGCTGTTGCATTTTTTAAAA CATTAATCCGAAGAAAAGATGTTTGAAAATTGTTTATAATGAGAAGTTATT TTGAGTTTTTTTTCCTTCTAAAAAAATAATGTTATTTTCATTATGTTTAAC |

| SEQ ID NO: | NAME (if any) | SEQUENCE |
|---|---|---|
| | | ACCCATAAAACTACTTCTGTTTTTTAAAGAATCTCTAAAAATCAATTTCT AAACGTCAAAAGTTTTTTATACAATTAGTTTAGGGTGTTTCTATGAGGGTT TGATAATATTTCTACGACTATATATATTTTTTTTTAAGGAAATTCTACGA CTACTTGTAGTTGGAATATGGGAATACGACTACTTTTCTATGAAGAGCAGG TTACGGTAGACACAAAAGCTGACTCTTGCGCAAAGCTTGTTCAACCCAATA GTGACATATTAGGAAATGAAAAATACCCTAATGCCTCCTTTTCAATACTCA AGAAAAGTCCTCCTTACCATATTGTCCCATTTTCTTTAAGAGCAGAGAAGA ACACATTTGTTCACACCAACATGATTTTTGTATGCTTGTAAATGAAAAGCT TCTAGTTATCCAGCTCAACCCGTGACTAAGGTCTATTCAATTTGCTTAGAA ATGAGGCATCAATTATGATGCAAATTTTTGTACTCATTACTCAATTCAAAA ACTATATGAACTTGTGGTGTCACGTAAGTGAATAACACTATCTAAATTTGA GTACAGTACTTCTCCTGTCACGGGGAGAAAAACACTCAAAATCAATTGTTA GAGATAAATTTTGTATCATAAATTAATTAATTTTACAATTACATCAATAAA TGTCATTGTTTAATCAAATAATATATGACAAAACTTCTTTGAAAATATACT GAGCAAAAACAAAACTATTAATTGCATGCAACGGCAACACATTTCTGTTTA CAATTATATTCGGTGAGTACTCAGTCAGTATAACCCAATTACCACATATGC ACGAATTCTCTTAGTGGGTCCACATTGTGGTGTTGAGTGGGACCCAATTG TAATGGATGGCCCACATACACCAAACTCAACCAAACAATTTCTCATAAAGT TCTATATAATAGCAATCCACTTTGCATCATTGAGG |
| 34 | 448-bp fragment of Comt promoter | CACCAACATGATTTTTGTATGCTTGTAAATGAAAAGCTTCTAGTTATCCAG CTCAACCCGTGACTAAGGTCTATTCAATTTGCTTAGAAATGAGGCATCAAT TATGATGCAAATTTTTGTACTCATTACTCAATTCAAAACTATATGAACTT ATGGTGTCACGTAAGTGAATAACACTATCTAAATTTGAGTACTTCTCCTGT CACGGGGAGAAAAACACTCAAAATCAATTGCATGCAACGGCAACACATTTC TGTTTACAATTATATTCGGTGAGTACTCAGTCAGTATAACCCAATTACCAC ATATGCACGAATTCTCTTAGTGGGTCCACATTGTGGTGTTGAGTGGGACC CAATTGTAATGGATGGCCCACATACACCAAACTCAACCAAACAATTTCTCA TAAAGTTCTATATAATAGCAATCCACTTTGCATCATTGAG |
| 35 | promoter of alfalfa Pet gene | ATAGTGGACCAGTTAGGTAGGTGGAGAAAGAAATTATTAAAAAAATATATT TATATGTTGTCAAATAACTCAAAAATCATAAAAGTTTAAGTTAGCAAGTGT GCACATTTTTATTTGGACAAAAGTATTCACCTACTACTGTTATAAATCATT ATTAAACATTAGAGTAAAGAAATATGGATGATAAGAATAAGAGTAGTGATA TTTTGACAACAATTTTGTTACAACATTTGAGAAAATTTTGTTGTTCTCTCT TTTCATTGGTCAAAAACAATAGAGAGAGAGAGAGAAAAAGGAAGAGGGAGA ATAAAAACATAATGTGAGTATGAGAGAGAAAGTTGTACAAAAGTTGTACCA AAATGGTTGTACAAATATCATTGAGGAATTTGACAAAAGCTACACAAATAA GGGTTAATTGCTGTAAATAAATAAGGATGACGCATTAGAGAGATGTACCAT TAGAGAATTTTTGGCAAGTCATTAAAAAGAAAGAATAAATTATTTTTAAAA TTAAAAGTTGAGTCATTTGATTAAACATGTGATTATTTAATGAATTGATGA GAGAGTTGGATTAAAGTTGTATTAATGATTAGAATTTGGTGTCAAATTTAA TTTGACATTTGATCTTTTCCTATATATTGCCCCATAGAGTCATTTAACTCA TTTTTTATATTTCATAGATCAAATAAGAGAAATAACGGTATATTAATCCCTC CAACAAAAAAAAAAAAAAACGGTATATTTACTAAAAAATCTAAGCCACGT AGGAGGATAACATCCAATCCAACCAATCACAACCTGATGAGATAACC CACTTTAAGCCCACGCACTCTGTGGCACATCTACATTATCTAAATCACACA TTCTTCCACACATCTGAGCCACACAAAAACCAATCCACATCTTTATCATCC ATTCTATAAAAAATCACACTTTGTGAGTCTACACTTTGATTCCCTTCAAAC ACATACAAAGAGAAGAGACTAATTAATTAATTAATCATCTTGAGAGAAAGC C |
| 36 | promoter of alfalfa Pal gene | AGAGAGGAGGCAGTGTACACAGGGGCAGAGAGAGGTGAGTCGTCTTTCTGG TAGGGCTGGTGTTGGGGATAGTGGTTGGTTTGAGAGTCAGGTGGTGAGGAG GGTTGGCGATGGGGTTGATACGTTGTTTTGGTTGGATAGGTGGTTAGGAGA TGCTCCTTTTTGTGTTTGTTCAGGAGGTTGTTTGAGTTAACAGAGAACAA ATTTGTGTCTGTGGCTAATTTGTTATCTGTTGACTCGGAGCAGTGGGGGGA GGTCTTGAGGTGAAGCGTATGGTGGCAGAGGTGGTGGCAGAGGTGAAGCGT ATGGTGGCAGCTGACGGAGGCAGTGTACACAGAGGTGGAGAGAGAGGAGAG AGAAGAGAAGAGAGAAAATGGAGAAGAGAGAAGAGAAGAGAGAGAAG ACAAATTTTGTGTGTGTGACCAAACCAAAATTCTTGGTCCTGGTCCACAC AAGATTTTCTCCCAACCAAGGTACAAGAATACCACGATCCAAGAGTGCCAC GTTGCAACATCATAACCGTTCAATAGTAAGAGATAATCGAACGGCCATAAT TAATTTTCAACAAACCCACTTTTTTCCTCCACTTTTGCAACTTGTCCCTC ATCACCTACCAAACACACATAGCACACCAACACACATAATAATATTATAAT AATTGTAAATATATGTAGCCTCCAAATTAGAAAGAAACCTCTATATAAAGC CTAACTACTTCCTTCACAAATCAGGAAATTCACAACTCTAATATTCATTTC TTTCCTAATCATTAGAATTTCCATTCTTATAAAATTCTAGGTACCACCACA CAACAAATAAAGGAACATTAATCAATACTATTAAGATGGATC |

| SEQ ID NO: | NAME (if any) | SEQUENCE |
|---|---|---|
| 37 | promoter of alfalfa Ccomt gene | CTTCTATTAATGATTTAATCAACCTTTTTAAAATACGAAGGTGACCTTAT<br>TTTGCAAATAATCCATCCATGGAAATGCATCATCCTTTTGAAAATGGGATT<br>ATCTGAATTCTTAAGTTACGTGAAAATTTAATACATTTCATTTTAGATAAA<br>TTTATTATTAAAATTCACACTTAGATGGCCTAAAAATTAACACTTATTTTT<br>AACAATTCAAATAAAATATACGACGAAATGAGTGTAATTTAGTTGGTTAAG<br>CATCCTCAAGCTTGGAGAGAAAGATCATAGTTTGATCTTTGAAAACTACAC<br>TATTGAAAAGGGTGAAGATATCTAAACATCCAAACAAAATTTATTTTGATA<br>GTCGATTCAAATTATCAAAATTTGTGAAAATATTTTGTAAATTGTTAAGTT<br>GGCAAAAATATGTTAATTTTCAAATTACCATTTGCACATTTTTCTAATCTC<br>AAATCACATTTAAGGGATGTTGACTACTTTAGTTTTGTACAAATCTTTACA<br>ATTTTAACATTTATAAAATGTGTTTCGGTAGATAAAAAGTGTGAGTATTGT<br>TTATAAGAGATTGTGTTTTTCTTTTGTTTAAACTTATAAAATAAATATATA<br>TTTTATTTTATTTTAATGTGAGATTGTAAGAATTCATTATAAGATTATGTC<br>ATTCCCTCAAAAGAAAATTAGATGATGTCATTTTCATAACTCATTTTCTAT<br>AAATACAGAAAATCCTCAAAAATGAAAAACCTCAGTCAAAAAATAAAAGAA<br>AAACATCAATAGTGGACTGGCCCACACTCATTGCTTTGCTTTAGTATAAGA<br>AAGTAGACCTCACCAACCACGAACCGGACGCCAACCGGTTCAACCAAACAT<br>TACACCAATTTTCCTTAACCATACCGGTTTTTCCCTCCCTTATATAACCAT<br>CTTCCTACCTCTTATCTAACCAAGCTCCATTCAACTCTTCAACACATATCA<br>GAAACAGAAAAAGAAGCAAAACATTCCAAGAATTTAACA |
| 38 | 171-bp fragment of Ccomt promoter | CATCAATAGTGGACTGGCCCACACTCATTGCTTTGCTTTAGTATAAGAAAG<br>TAGACCTCACCAACCACGAACCGGACGCCAACCGGTTCAACCAAACATTAC<br>ACCAATTTTCCTTAACCATACCGGTTTTTCCCTCCCTTATATAACCATCTT<br>CCTACCTCTTATCTAACC |
| 39 | promoter of tomato polygalac-turonase gene | AAGCTTCTTAAAAAGGCAAATTGATTAATTTGAAGTCAAAATAATTAATTA<br>TAACAATGGTAAAGCACCTTAAGAAACCATAGTTTGAAAGGTTACCAATGC<br>GCTATATATTAATCAACTTGATAATATAAAAAAAATTTCAATTCGAAAAGG<br>GCCTAAAATATTCTCAAAGTATTCGAAATGGTACAAAACTACCATCCGTCC<br>ACCTATTGACTCCAAAATAAAATTATTATCCACCTTTGAGTTTAAAATTGA<br>CTACTTATATAACAATTCTAAATTTAAACTATTTTAATACTTTTAAAAATA<br>CATGGCGTTCAAATATTTAATATAATTTAATTTATGAATATCATTTATAAA<br>CCAACCAACTACCAACTCATTAATCATTAAATCCCACCCAAATTCTACTAT<br>CAAAATTGTCCTAAACACTACTAAAACAAGACGAAATTGTTCGAGTCCGAA<br>TCGAAGCACCAATCTAATTTAGGTTGAGCCGCATATTTAGGAGGACACTTT<br>CAATAGTATTTTTTTCAAGCATGAATTTGAAATTTAAGATTAATGGTAAAG<br>AAGTAGTACACCCGAATTAATTCATGCCTTTTTTAAATATAATTATATAAA<br>TATTTATGATTTGTTTTAAATATTAAAACTTGAATATATTATTTTTAAAAA<br>AATTATCTATTAAGTACCATCACATAATTGAGACGAGGAATAATTAAGATG<br>AACATAGTGTTTAATTAGTAATGGATGGGTAGTAAATTTATTTATAAATTA<br>TATCAATAAGTTAAATTATAACAAATATTTGAGCGCCATGTATTTTAAAAA<br>ATATTAAATAAGTTTGAATTTAAAACCGTTAGATAAATGGTCAATTTTGAA<br>CCCAAAAGTGGATGAGAAGGGTATTTTAGAGCCAATAGGGGGATGAGAAGG<br>ATATTTTGAAGCCAATATGTGATGGATGGAGGATAATTTTGTATCATTTCT<br>AATACTTTAAAGATATTTTAGGTCATTTTCCCTTCTTTAGTTTATAGACTA<br>TAGT |
| 40 | transfer DNA of pSIM870 (Russet Boise III) | TGGCAGGATATATACCGGTGTAAACGAAGTGTGTGGTTGATCCAAAATC<br>TATCGTACCTTTAGAAAGTGTAGCTATGAAGGATAGTCTCACTTATGAAGA<br>ACTACCTATTGAGATTCTTGATCGTCAGGTCCGAAGGTTGAGAAAAATAGA<br>AGTCGCTTCAGTTACGGCTTTGTGGAGGAGTAAGGGTACCGAACCATGCAT<br>CTCAATCTTAATACTAAAAAATGCAACAAAATTCTAGTGGAGGGACCAGTA<br>CCAGTACATTAGATATTATCTTTTATTACTATAATAATATTTTAATTAACA<br>CGAGACATAGGAATGTCAAGTGGTAGCGGTAGGAGGGAGTTGGTTCAGTTT<br>TTTAGATACTAGGAGACAGAACCGGAGGGGCCCATTGCAAGGCCCAAGTTG<br>AAGTCCAGCCGTGAATCAACAAAGAGAGGGCCCATAATACTGTCGATGAGC<br>ATTTCCCTATAATACAGTGTCCACAGTTGCCTTCCGCTAAGGGATAGCCAC<br>CCGCTATTCTCTTGACACGTGTCACTGAAACCTGCTACAAATAAGGCAGGC<br>ACCTCCTCATTCTCACACTCACTCACTCACACAGCTCAACAAGTGGTAACT<br>TTTACTCATCTCCTCCAATTATTTCTGATTTCATGCATGTTTCCCTACATT<br>CTATTATGAATCGTGTTATGGTGTATAAACGTTGTTTCATATCTCATCTCA<br>TCTATTCTGATTTTGATTCTCTTGCCTACTGAATTTGACCCTACTGTAATC<br>GGTGATAAATGTGAATGCTTCCTCTTCTTCTTCTTCTCAGAAATCAAT<br>TTCTGTTTTGTTTTTGTTCATCTGTAGCTTGGTAGATTCCCCTTTTTGTAG<br>ACCACACATCACGGATCCCCAAACATAATTGTAACTGATTATTCTTGAA<br>TAACAACTTCAATGAAATCAAGCAACAAAGCTGATTTCAACATGAAAAAAC<br>AGAACAAGAAAACGAAAACAGAGCATCATCCATCAAAGTGTAATCTCAGCA<br>GATT |

| SEQ ID NO: | NAME (if any) | SEQUENCE |
|---|---|---|
| 41 | fragment of trailer of phosphorylase gene | GAGGGGGAAGTGAATGAAAAATAACAAAGGCACAGTAAGTAGTTTCTCTTT TTATCATGTGATGAAGGTATATAATGTATGTGTAAGAGGATGATGTTATTA CCACATAATAAGAGATGAAGAGTCTCATTTTCTGCTT |
| 42 | transfer DNA of pSIM870 (Russet Boise IV) | TGGCAGGATATATACCGGTGTAAACGAAGTGTGTGTGGTTGATCCAAAATC TATCGTACCTTTAGAAAGTGTACCTATGAAGGATAGTCTCACTTATGAAGA ACTACCTATTGAGATTCTTGATCGTCAGGTCCGAAGGTTGAGAAAAATAGA AGTCGCTTCAGTTACGGCTTTGTGGAGGAGTAAGGGTACCGAACCATGCAT CTCAATCTTAATACTAAAAAATGCAACAAAATTCTAGTGGAGGGACCAGTA CCAGTACATTAGATATTATCTTTTATTACTATAATAATATTTTAATTAACA CGAGACATAGGAATGTCAAGTGGTAGCGGTAGGAGGGAGTTGGTTCAGTTT TTTAGATACTAGGAGACAGAACCGGAGGGGCCCATTGCAAGGCCCAAGTTG AAGTCCAGCCGTGAATCAACAAAGAGAGGGCCCATAATACTGTCGATGAGC ATTTCCCTATAATACAGTGTCCACAGTTGCCTTCCGCTAAGGGATAGCCAC CCGCTATTCTCTTGACACGTGTCACTGAAACCTGCTACAAATAAGGCAGGC ACCTCCTCATTCTCACACTCACTCACTCACACAGCTCAACAAGTGGTAACT TTTACTCATCTCCTCCAATTATTTCTGATTTCATGCATGTTTCCCTACATT CTATTATGAATCGTGTTATGGTGTATAAACGTTGTTTCATATCTCATCTCA TCTATTCTGATTTTGATTCTCTTGCCTACTGAATTTGACCCTACTGTAATC GGTGATAAATGTGAATGCTTCCTCTTCTTCTTCTTCTCAGAAATCAAT TTCTGTTTTGTTTTTGTTCATCTGTAGCTTGGTAGATTCCCCTTTTTGTAG ACCACACATCACGGATCCCCCAAACATAATTGTAACTGATTTATTCTTGAA TAACAACTTCAATGAAATCAAGCAACAAAGCTGATTTCAACATGAAAAAAC AGAACAAGAAAACGAAAACAGAGCATCATCCATCAAAGTGTAATCTCAGCA GATTCAATAGAGACTAACTCGAGGTGCTCTCTATGCAAATCTAGCTTTTCG AATGAGAGTGATAAGAGAGTGAGGATTGTGAATTATTTTATTGATGAAGAT TGGAGAAGTCAATTATTGATTCACACACAGGAATTAAGTGTGTTGTTGTGC GTCCTCTTGTGGAAATTAAATGTCACCCTTTTTTTATTTATCAATAAAAGC ACGAAAATCTCCTGCACTACTCCCCTGCACTCTCTTATATTTGTCCATTTC CCACAAATCCCTAACTTAATTACTTACCCACACTCAAGCTTAAGCAGAAAA TGAGACTCTTCATCTCTTATTATGTGGTAATAACATCATCCTCTTACACAT ACATTATATACCTTCATCACATGATAAAAAGAGAAACTACTTACTGTGCCT TTGTTATTTTTCATTCACTTCCCCCTCCCGCGGGTTAAATTCATGATTTTA TGAACTCAATAGCTTTTCATAATGAGCAATATTATCTTTCTTCAGTAGCAA ATCCACATGCTCTTATGCTCGCTGAAATAGTTTTGGCCGTGGAGTTTCACC ATCTATGTTTACAATTGATTCTTGTAGCTGCAGGAGGGGAAGTGAATGAA AAATAACAAAGGCACAGTAAGTAGTTTCTCTTTTTATCATGTGATGAAGGT ATATAATGTATGTGTAAGAGGATGATGTTATTACCACATAATAAGAGATGA AGAGTCTCATTTTCTGCTTAAGCTTGAGTGTGGGTAAGTAATTAAGTTAGG GATTTGTGGGAAATGGACAAATATAAGAGAGTGCAGGGGAGTAGTGCAGGA GATTTTCGTGCTTTTATTGATAAATAAAAAAAGGGTGACATTTAATTTCCA CAAGAGGACGCAACACAACACACTTAATTCCTGTGTGTGAATCAATAATTG ACTTCTCCAATCTTCATCAATAAAATAATTCACAATCCTCACTCTCTTATC ACTCTCATTCGAAAAGCTAGATTTGCATAGAGAGCACCTCGAGTTAGTCTC TATTGAATCTGCTGAGATTACACTTTGATGGATGATGCTCTGTTTTCGTTT TCTTGTTCTGTTTTTTCATGTTGAAATCAGCTTTGTTGCTTGATTTCATTG AAGTTGTTATTCAAGAATAAATCAGTTACAATTATGTTTGGGTCTAGAGTG ATGTGTGGTCTACAAAAAGGGGAATCTACCAAGCTACAGATGAACAAAAAC AAAACAGAAATTGATTTCTGAGAAGAAGAAGAAGAGGAAGCATTCACA TTTATCACCGATTACAGTAGGGTCAAATTCAGTAGGCAAGAGAATCAAAAT CAGAATAGATGAGATGAGATATGAAACAACGTTTATACACCATAACACGAT TCATAATAGAATGTAGGGAAACATGCATGAAATCAGAAATAATTGGAGGAG ATGAGTAAAAGTTACCACTTGTTGAGCTGTGTGAGTGAGTGAGTGTGAGAA TGAGGAGGTGCCTGCCTTATTTGTAGCAGGTTTCAGTGACACGTGTCAAGA GAATAGCGGGTGGCTATCCCTTAGCGGAAGGCAACTGTGGACACTGTATTA TAGGGAAATGCTCATCGACAGTATTATGGGCCCTCTCTTTGTTGATTCACG GCTGGACTTCAACTTGGGCCTTGCAATGGGCCCCTCCGGTTCTGTCTCCTA GTATCTAAAAAACTGAACCAACTCCCTCCTACCGCTACCACTTGACATTCC TATGTCTCGTGTTAATTAAAATATTATTATAGTAATAAAAGATAATATCTA ATGTACTGGTACTGGTCCCTCCACTAGAATTTGTTGCATTTTTTAGTATT AAGATTGAGATGCATGGTTCGAGCTCCCGCAGTGTGCCAGGGCTGTCGGCA GATGGACATAAATGGCACACCGCTCGGCTCGTGGAAAGAGTATGGTCAGTT TCATTGATAAGTATTTACTCGTATTCGGTGTTTACATCAAGTTAATATGTT CAAACACATGTGATATCATACATCTAGTTAAGTATAAATGCCAACTTT TTACTTGAATCGCCGAATAAATTTACTTACGTCCAATATTTAGTTTTGTGT GTCAAACATATCATGCACTATTTGATTAAGAATAAATAAACGATGTGTAAT TTGAAAACCAATTAGAAAAGAAGTATGACGGGATTGATGTTCTGTGAAATC ACTGGTAAATTGGACGGACGATGAAATTTGATCGTCCATTTAAGCATAGCA ACATGGGTCTTTAGTCATCATCATTATGTTATAATTATTTTCTTGAAACTT |

| SEQ ID NO: | NAME (if any) | SEQUENCE |
|---|---|---|
| | | GATACACCAACTTTCATTGGGAAAGTGACAGCATAGTATAAACTATAATAT |
| | | CAATTCTGGCAATTTCGAATTATTCCAAATCTCTTTTGTCATTTCATTTCC |
| | | TCCCCTATGTCTGCAAGTACCAATTATTTAAGTACAAAAAATCTTGATTAA |
| | | ACAATTTATTTTCTCACTAATAATCACATTTAATCATCAACGGTTCATACA |
| | | CGTCTGTCACTCTTTTTTTATTCTCTCAAGCGCATGTGATCATACCAATTA |
| | | TTTAAATACAAAAAATCTTGATTAAACAATTCAGTTTCTCACTAATAATCA |
| | | CATTTAATCATCAACGGTTCATACACATCCGTCACTCTTTTTTTATTCTCT |
| | | CAAGCGCATGTGATCATACCAATTATTTAAATACAAAAAATCTTGATTAAA |
| | | CAATTCATTTCTCACTAATAATCACATTTAATCATCAACGGTTTATACAC |
| | | GTCCGCCACTCTTTTTTTATTCTCTCAAGCGTATGTGATCATATCTAACTC |
| | | TCGTGCAAACAAGTGAAATGACGTTCACTAATAAATAATCTTTTGAATACT |
| | | TTGTTCAGTTTAATTTATTTAATTTGATAAGAATTTTTTTATTATTGAATT |
| | | TTTATTGTTTTAAATTAAAAATAAGTTAAATATATCAAAATATCTTTTAAT |
| | | TTTATTTTGAAAAATAACGTAGTTCAAACAAATTAAAATTGAGTAACTGT |
| | | TTTTCGAAAAATAATGATTCTAATAGTATATTCTTTTTCATCATTAGATAT |
| | | TTTTTTTAAGCTAAGTACAAAAGTCATATTTCAATCCCCAAAATAGCCTCA |
| | | ATCACAAGAAATGCTTAAATCCCCAAAATACCCTCAATCACAAGACGTGTG |
| | | TACCAATCATACCTATGGTCCTCTCGTAAATTCCGACAAAATCAGGTCTAT |
| | | AAAGTTACCCTTGATATCAGTATTATAAAACTAAAAATCTCAGCTGTAATT |
| | | CAAGTGCAATCACACTCTACCACACACTCTCTAGTAGAGAGATCAGTTGAT |
| | | AACAAGCTTGTTAACGGATCCAAAATTCTTATGTTAACCAAATAAATTGAG |
| | | ACAAATTAATTCAGTTAACCAGAGTTAAGAGTAAAGTACTATTGCAAGAAA |
| | | ATATCAAAGGCAAAGAAAAGATCATGAAAGAAATATCAAAGAAAAAGAA |
| | | GAGGTTACAATCAAACTCCCATAAAACTCCAAAAATAAACATTCAAATTGC |
| | | AAAAACATCCAATCAAATTGCTCTACTTCACGGGGCCCACGCCGGCTGCAT |
| | | CTCAAACTTTCCCACGTGACATCCCATAACAAATCACCACCGTAACCCTTC |
| | | TCAAAACTCGACACCTCACTCTTTTTCTCTATATTACAATAAAAAATATAC |
| | | GTGTCCCCGCGGGTTAAATTCATGATTTTATGAACTCAATAGCTTTTCATA |
| | | ATGAGCAATATTATCTTTCTTCAGTAGCAAATCCACATGCTCTTATGCTCG |
| | | CTGAAATAGTTTTGGCCGTGGAGTTTCACCATCTATGTTTACAATTGATTC |
| | | TTGTAGCTGCAGGGACACGTATATTTTTATTGTAATATAGAGAAAAAGAG |
| | | TGAGGTGTCGAGTTTTGAGAAGGGTTACGGTGGTGATTTGTTATGGGATGT |
| | | CACGTGGGAAAGTTTGAGATGCAGCCGGCGTGGGCCCCGTGAAGTAGAGCA |
| | | ATTTGATTGGATGTTTTTGCAATTTGAATGTTTATTTTTGGAGTTTTATGG |
| | | GAGTTTGATTGTAACCTCTTCTTTTTCTTTGATATTTTCTTTCATGATCTT |
| | | TTCTTTTGCCTTTGATATTTTCTTGCAATAGTACTTTTACTCTTAACTCTGG |
| | | TTAACTGAATTAATTTGTCTCAATTTATTTGGTTAACATAAGAATTTTTCT |
| | | AGAGTGATGTGTGGTCTACAAAAAGGGGAATCTACCAAGCTACAGATGAAC |
| | | AAAAACAAAACAGAAATTGATTTCTGAGAAGAAGAAGAAGAAGAGGAAGCA |
| | | TTCACATTTATCACCGATTACAGTAGGGTCAAATTCAGTAGGCAAGAGAAT |
| | | CAAAATCAGAATAGATGAGATGAGATATGAAACAACGTTTATACACCATAA |
| | | CACGATTCATAATAGAATGTAGGGAAACATGCATGAAATCAGAAATAATTG |
| | | GAGGAGATGAGTAAAAGTTACCACTTGTTGAGCTGTGTGAGTGAGTGAGTG |
| | | TGAGAATGAGGAGGTGCCTGCCTTATTTGTAGCAGGTTTCAGTGACACGTG |
| | | TCAAGAGAATAGCGGGTGGCTATCCCTTAGCGGAAGGCAACTGTGGACACT |
| | | GTATTATAGGGAAATGCTCATCGACAGTATTATGGGCCCTCTCTTTGTTGA |
| | | TTCACGGCTGGACTTCAACTTGGGCCTTGCAATGGGCCCCTCCGGTTCTGT |
| | | CTCCTAGTATCTAAAAAACTGAACCAACTCCCTCCTACCGCTACCACTTGA |
| | | CATTCCTATGTCTCGTGTTAATTAAAATATTATTATAGTAATAAAAGATAA |
| | | TATCTAATGTACTGGTACTGGTCCCTCCACTAGAATTTTGTTGCATTTTTT |
| | | AGTATTAAGATTGAGATGCATGGTTCGAGCTCCTTCAACATGTTATAAACT |
| | | TCACATATTCAGTTGGGAATAGGCTTTATAATGAGTTGGACTACGTTATGT |
| | | CCCCCTCAAGTCCCAGAATTATGTGCCCCCGTATGTTATAAGTCCCCTCTG |
| | | CGGGCATCAATTTAGTGATCACGCCAGACATGCCTCTATACCTCGGCCAGG |
| | | ATATATTTGTTGGTAATG |
| 43 | R1 intron | GTAAATTTCTAGTGATTATACTGTACATTTCGCATAATTTAGGATCGTATT |
| | | TGATATGTTTTACGCTTGATTGATCGAGAACTTAAAGCTTTTCTGATCTGA |
| | | AATTTGTTTTTTGGCATACTCGAGTTGAGATCCTGGTTAAATCAGTGTTAT |
| | | TTCGATTGAATTTTAGCAAAATTTGGTGTTGATTTTCAGTATTTTCATGGT |
| | | TTAATGTATATAAACAAGCTTAATTTTTCAAATTCAAGCTCGTTTAACCTT |
| | | TTAATTACAGCTATTTCTGGAAAAAAGTTTGGTGATTTCTCTAGATGTTT |
| | | TATTCGAGAAAAAAACAAAAACGAAAAAAGGGGAAATGCTGTTCTGTATGT |
| | | ACAAAAAGTGATTGATCAGCTTTTGGTCACCGACATACATTTGATTAGTAC |
| | | ATACACGAGTCATACGAGTATATTTCCGTGTGCACTTTATTGTTTTGAAGG |
| | | AATTCTGGATTTGGTTGATTCCTTTTAAAACTTCTAAGTTTTTTTGTTA |
| | | CATTTTACTCTAATTAAGTCTTCTCTGTGAACTGACAAATACTCACCAGGC |
| | | ACACATTACAACCTTCATTTGATTATCCGCGAACGATCCATTGCTTTTGTG |
| | | TATATTGCTTTTGTATTGACTGATTTTGTATTGTATTAGCAG |

| SEQ ID NO: | NAME (if any) | SEQUENCE |
|---|---|---|
| 44 | potato border St02 | CATTACCAACAAATATATCCTGGCC |
| 45 | tomato border Le01 | CATTACCAACAAATATATCCTGGCC |
| 46 | tomato border | CTCTACCTCTGAATATATCCTGCGG |
| 47 | pepper border Ca01 | CATTACCAACAAATATATCCTGGCC |
| 48 | alfalfa border Ms01 | GTATACCTCTGTATACATCCTGCCG |
| 49 | barley border Hv01 | ATATACCAAATGATACATCCTGCCC |
| 50 | rice border Os01 | ACTTACTCAAGGATATATCCTGGCT |
| 51 | 300-bp central fragment of P1 promoter | GCCTCAACAAGGTCAGGGTACAGAGTCTCCAAACCATTAGCCAAAAGCTACAGGAGATCAATGAAGAATCTTCAATCAAAGTAAACTACTGTTCCAGCACATGCATCATGGTCAGTAAGTTTCAGAAAAAGACATCCACCGAAGACTTAAAGTTAGTGGGCATCTTTGAAAGTAATCTTGTCAACATCGAGCAGCTGGCTTGTGGGGACCAGACAAAAAAGGAATGGTGCAGAATTGTTAGGCGCACCTACCAAAAGCATCTTTGCCTTTATTGCAAAGATAAAGCAGATTCCTCTAGTA |
| 52 | Comt gene fragment | AATGCCCCCATCAAGGACTGCATCTTTTAGGTGGTACCAGCTTTCCATGAGCACTTTATCCTGATTCATGAGATTAAGAGCAGAAATGGATACACCATCTTCATTCTTAACCAAATACTTAGCAACAGTAGCCAAACCATAAAGTCTCTGAACCTTTCCATCTTGTTGAGTACGAACTGAACAAGTGAGGATATTGTAACAAGCCAAGAGACGCAACATTCGGTCCAACATAACTGGTGCATCAGGGTTAGTTGTTGGTAGCTGAGAACCAATTTCAATAGGTGAAATTTGAGCACCAGGTCCA |
| 53 | Comt gene fragment | AATGCCCCCATCAAGGACTGCATCTTTTAGGTGGTACCAGCTTTCCATGAGCACTTTATCCTGATTCATGAGATTAAGAGCAGAAATGGATACACCATCTTCATTCTTAACCAAATACTTAGCAACAGTAGCCAAACCATAAAGTCTCTGAACCTTTCCATCTTGTTGAGTACGAACTGAACAAGTGAGGATATTGTAACAAGCCAAGAGACGCAACATTCGGTCCAACATAACTGGTGCATCAGGGTTAGTTGTTGGTAGCTGAGAAGCAATTTCAATAGGTGAAATTTGAGCACCAGGTCCAGAATTCAATCTCACAAAAACCTCATCAATCACAACCATGGGTTCAACAGGTGAAACTCAAATAACACCAACCCACATATCAGATGAAGAAGCAAACCTCTTCGCCATGCAACTAGCAAGTGCTTCAGTTCTTCCCATGATTTTGAAATCAGCTCTTGAACTTGATCTCTTAGAAATCATTGCTAAAGC |
| 54 | Alfalfa promoter | GGGCCCATAGTGGACCAGTTAGGTAGGTGGAGAAAGAAATTATTAAAAAAATATATTTATATGTTGTCAAATAACTCAAAAATCATAAAAGTTTAAGTTAGCAAGTGTGCACATTTTTATTTGGACAAAAGTATTCACCTACTACTGTTATAAATCATTATTAAACATTAGAGTAAAGAAATATGGATGATAAGAATAAGAGTAGTGATATTTTGACAACAATTTTGTTACAACATTTGAGAAAATTTTGTTGTTCTCTCTTTTCATTGGTCAAAAACAATAGAGAGAGAGAGAGAAAAAGGAAGAGGGAGAATAAAAACATAATGTGAGTATGAGAGAGAAAGTTGTACAAAAGTTGTACCAAAATGGTTGTACAAATATCATTGAGGAATTTGACAAAAGCTACACAAATAAGGGTTAATTGCTGTAAATAAATAAGGATGACGCATTAGAGAGATGTACCATTAGAGAATTTTTGGCAAGTCATTAAAAAGAAAGAATAAATTATTTTTAAAATTAAAAGTTGAGTCATTTGATTAAACATGTGATTATTTAATGAATTGATGAGAGAGTTGGATTAAAGTTGTATTAATGATTAGAATTTGGTGTCAAATTTAATTTGACATTTGATCTTTTCCTATATATTGCCCCATAGAGTCATTTAACTCATTTTTATATTTCATAGATCAAATAAGAGAAATAACGGTATATTAATCCCTCCAACAAAAAAAAAAAAAAACGGTATATTTACTAAAAAATCTAAGCCACGTAGGAGGATAACATCCAATCCAACCAATCACAACAATCCTGATGAGATAACCCACTTTAAGCCCACGCACTCTGTGGCACATCTACATTATCTAAATCACACATTCTTCCACACATCTGAGCCACACAAAACCAATCCACATCTTTATCATCCATTCTATAAAAAATCACACTTTGTGAGTCTACACTTTGATTCCCTTCAAACACATACAAAGAGAAGAGACTAATTAATTAATTAATCATCTTGAGAGAAAGCC |

| SEQ ID NO: | NAME (if any) | SEQUENCE |
|---|---|---|
| 55 | Alfalfa promoter | AGAGAGGAGGCAGTGTACACAGGGGCAGAGAGAGGTGAGTCGTCTTTCTGG<br>TAGGGCTGGTGTTGGGGATAGTGGTTGGTTTGAGAGTCAGGTGGTGAGGAG<br>GGTTGGCGATGGGGTTGATACGTTGTTTTGGTTGGATAGGTGGTTAGGAGA<br>TGCTCCTTTTTGTGTTTGTTTCAGGAGGTTGTTTGAGTTAACAGAGAACAA<br>ATTTGTGTCTGTGGCTAATTTGTTATCTGTTGACTCGGAGCAGTGGGGGGA<br>GGTGTTGAGGTGAAGCGTATGGTGGCAGAGGTGGTGGCAGAGGTGAAGCGT<br>ATGGTGGCAGCTGAGGGAGGCAGTGTACACAGAGGTGGAGAGAGAGGAGAG<br>AGAAGAGAGAAGAGAGAGAAATGGAGAAGAGAGAAGAGAAGAGAGAGAAG<br>ACAAATTTTTGTGTGTGTGACCAAACCAAAATTCTTGGTCCTGGTCCACAC<br>AAGATTTTCTCCCAACCAAGGTACAAGAATACCACGATCCAAGAGTGCCAC<br>GTTGCAACATCATAACCGTTCAATAGTAAGAGATAATCGAACGGCCATAAT<br>TAATTTTCAACAAACCCACTTTTTTCCTCCTACTTTTGCAACTTGTCCCTC<br>ATCACCTACCAAACACACATAGCACACCAACACACATAATAATATTATAAT<br>AATTGTAAATATATGTAGCCTCCAAATTAGAAAGAAACCTCTATATAAAGC<br>CTAACTACTTCCTTCACAAATCAGGAAATTCACAACTCTAATATTCATTTC<br>TTTCCTAATCATTAGAATTTCCATTCTTATAAAATTCTAGGTACCACCACA<br>CAACAAATAAAGGAACATTAATCAATACTATTAAGAT |
| 56 | Alfalfa DNA fragment that functions as alternative to the Agrobacterium left border | CGGCAGGATGTATACAGAGGTATACAATTTTATATTACATTTATATTTGTG<br>TTAATTCATTGAATTTTCACTTTTATTTTTACTTTGATAATCAACTGTGT<br>AAAGAATTATTTGAAAAATATATATAATTTATAGAATTTTTTTTGTTATG |
| 57 | Alfalfa DNA fragment that v functions as alternative to the Agrobacterium right border | CTAGATTATGCGGGCTAACGGGCTGCCCGCGGCCCTTTCGGGCTAGCCCTA<br>ACGGGTACCGGGCCCCGGCAGGATGTATACAGAGGTATAC |
| 58 | Entire transfer DNA of pSIM856 | CGGCAGGATGTATACAGAGGTATACAATTTTATATTACATTTATATTTGTG<br>TTAATTCATTGAATTTTCACTTTTATTTTTACTTTGATAATCAACTGTGT<br>AAAGAATTATTTGAAAAATATATATAATTTATAGAATTTTTTTTGTTATG<br>GGGCCCATAGTGGACCAGTTAGGTAGGTGGAGAAAGAAATTATTAAAAAAA<br>TATATTTATATGTTGTCAAATAACTCAAAAATCATAAAAGTTTAAGTTAGC<br>AAGTGTGCACATTTTTATTTGGACAAAAGTATTCACCTACTACTGTTATAA<br>ATCATTATTAAACATTAGAGTAAAGAAATATGGATGATAAGAATAAGAGTA<br>GTGATATTTTGACAACAATTTTGTTACAACATTTGAGAAAATTTTGTTGTT<br>CTCTCTTTTCATTGGTCAAAAACAATAGAGAGAGAGAGAGAAAAAGGAAGA<br>GGGAGAATAAAAACATAATGTGAGTATGAGAGAGAAAGTTGTACAAAAGTT<br>GTACCAAAATGGTTGTACAAATATCATTGAGGAATTTGACAAAAGCTACAC<br>AAATAAGGGTTAATTGCTGTAAATAAATAAGGATGACGCATTAGAGAGATG<br>TACCATTAGAGAATTTTTGGCAAGTCATTAAAAAGAAAGAATAAATTATTT<br>TTAAAATTAAAAGTTGAGTCATTTGATTAAACATGTGATTATTTAATGAAT<br>TGATGAGAGAGTTGGATTAAAGTTGTATTAATGATTAGAATTTGGTGTCAA<br>ATTTAATTTGACATTTGATCTTTTCCTATATATTGCCCCATAGAGTCATTT<br>AACTCATTTTTATATTTCATAGATCAAATAAGAGAAATAACGGTATATTAA<br>TCCCTCCAACAAAAAAAAAAAAAAAACGGTATATTTACTAAAAAATCTAAG<br>CCACGTAGGAGGATAACATCCAATCCAACCAATCACAACAATCCTGATGAG<br>ATAACCCACTTTAAGCCCACGCACTCTGTGGCACATCTACATTATCTAAAT<br>CACACATTCTTCCACACATCTGAGCCACACAAAAACCAATCCACATCTTTA<br>TCATCCATTCTATAAAAAATCACACTTTGTGAGTCTACACTTTGATTCCCT<br>TCAAACACATACAAAGAAGAGACTAATTAATTAATTAATCATCTTGAGA<br>GAAAGCCCTGCAGAATGCCCCCATCAAGGACTGCATCTTTTAGGTGGTACC<br>AGCTTTCCATGAGCACTTTATCCTGATTCATGAGATTAAGAGCAGAAATGG<br>ATACACCATCTTCATTCTTAACCAAATACTTAGCAACAGTAGCCAAACCAT<br>AAAGTCTCTGAACCTTTCCATCTTGTTGAGTACGAACTGAACAAGTGAGGA<br>TATTGTAACAAGCCAAGAGACGCAACATTCGGTCCAACATAACTGGTGCAT<br>CAGGGTTAGTTGTTGGTAGCTGAGAAGCAATTTCAATAGGTGAAATTTGAG<br>CACCAGGTCCAGCTTTAGCAATGATTTCTAAGAGATCAAGTTCAAGAGCTG<br>ATTTCAAAATCATGGGAAGAACTGAAGCACTTGCTAGTTGCATGGCGAAGA |

| SEQ ID NO: | NAME (if any) | SEQUENCE |
|---|---|---|
| | | GGTTTGCTTCTTCATCTGATATGTGGGTTGGTGTTATTTGAGTTTCACCTG<br>TTGAACCCATGGTTGTGATTGATGAGGTTTTTGTGAGATTGAATTCTGGAC<br>CTGGTGCTCAAATTTCACCTATTGAAATTGCTTCTCAGCTACCAACAACTA<br>ACCCTGATGCACCAGTTATGTTGGACCGAATGTTGCGTCTCTTGGCTTGTT<br>ACAATATCCTCACTTGTTCAGTTCGTACTCAACAAGATGGAAAGGTTCAGA<br>GACTTTATGGTTTGGCTACTGTTGCTAAGTATTTGGTTAAGAATGAAGATG<br>GTGTATCCATTTCTGCTCTTAATCTCATGAATCAGGATAAAGTGCTCATGG<br>AAAGCTGGTACCACCTAAAAGATGCAGTCCTTGATGGGGGCATTGGATCCA<br>TCTTAATAGTATTGATTAATGTTCCTTTATTTGTTGTGTGGTGGTACCTAG<br>AATTTTATAAGAATGGAAATTCTAATGATTAGGAAAGAAATGAATATTAGA<br>GTTGTGAATTTCCTGATTTGTGAAGGAAGTAGTTAGGCTTTATATAGAGGT<br>TTCTTTCTAATTTGGAGGCTACATATATTTACAATTATTATAATATTATTA<br>TGTGTGTTGGTGTGCTATGTGTGTTTGGTAGGTGATGAGGGACAAGTTGCA<br>AAAGTAGGAGGAAAAAAGTGGGTTTGTTGAAATTAATTATGGCCGTTCGA<br>TTATCTCTTACTATTGAACGGTTATGATGTTGCAACGTGGCACTCTTGGAT<br>CGTGGTATTCTTGTACCTTGGTTGGGAGAAAATCTTGTGTGGACCAGGACC<br>AAGAATTTTGGTTTGCTCACACACACAAAAATTTGTCTTCTCTCTCTTCTC<br>TTCTCTCTTCTCCATTTTCTCTCTCTTCTCTCTTCTCTCTCCTCTCTCTCC<br>ACCTCTGTGTACACTGCCTCCCTCAGCTGCCACCATACGCTTCACCTCTGC<br>CACCACCTCTGCCACCATACGCTTCACCTCAACACCTCCCCCCACTGCTCC<br>GAGTCAACAGATAACAAATTAGCCACAGACACAAATTTGTTCTCTGTTAAC<br>TCAAACAACCTCCTGAAACAAACACAAAAAGGAGCATCTCCTAACCACCTA<br>TCCAACCAAAACAACGTATCAACCCCATCGCCAACCCTCCTCACCACCTGA<br>CTCTCAAACCAACCACTATCCCCAACACCAGCCCTACCAGAAAGACGACTC<br>ACCTCTCTCTGCCCCTGTGTACACTGCCTCCTCTCTCTAGATTATGCGGGC<br>TAACGGGCTGCCCGCGGCCCTTTCGGGCTAGCCCTAACGGGTACCGGGCCC<br>CGGCAGGATGTATACAGAGGTATAC |
| 59 | COMT promoter from maize | TTCCACGGCAGCTGCCACCGTCGCTATCGCTGACCAACCCGGCTGGTCGCC<br>TCTGTGCTCCATCCATGCATGTTACAACTATGCAGATGCAGCCGAAACAAA<br>CACTGGCTAGAAAGGCAGCCCAACGGGCCTACTGTCATTCGCTCCGGCATC<br>CTACTGGTGGGCCCACTTGCACCGGCCGATGACCAGTTCATCATTTTTCTC<br>GACGAATTTGTGCACAGAATTTGCTAAAAATTCTTCGCACGTGGCAAAACC<br>AGGGGGAAAATCGACAACTAGTCGGGGTTTTTTTAATTCCCTGATAGAATA<br>GTCCCTGCTAATCATCCATGAAAACCAAACACGTACTCTACGTCACCGTCA<br>TGGATGGAGCGAGTGAACTGATGATTTTTTCCCCATCCCGCACGCAACAGC<br>ATGGGTGACAACAACCACTCCCGCTGCGGTTGGGCGAGCACATCTCTACGC<br>ACTTGACACTCACGCAAACCTAACGCATACTAGAGTAATCATCGCCACCAA<br>CTATCGGCGACAGAAACGATCGGCCCCGCTTCTCTTAATCACGGTGCTTGA<br>ATTAGTGCGCGCATAGTAGTGAAAAATAATAGTGAAAAATAAGCAGTGCGT<br>GTTTTGGTGTGGTGGTTGGTGAGCCGTCCGCCCCAATAAAAACCCCTCGCA<br>CCACCTCGTCCCT |

What is claimed is:

1. A construct, comprising an expression cassette which comprises convergently-oriented first and second promoters, wherein (i) the first promoter is operably linked to a first polynucleotide and (ii) the second promoter is operably linked to a second polynucleotide, wherein (a) neither the first nor the second polynucleotide is operably linked to a terminator, and (b) the second polynucleotide and the first polynucleotide are fully identical in sequence over at least 23 nucleotides, wherein the second polynucleotide is positioned within the cassette in a different orientation to the first polynucleotide, and wherein the direction of transcription initiated from the first promoter is toward the second promoter and the direction of transcription initiated from the second promoter is toward the first promoter.

2. The construct of claim 1, wherein at least part of the second polynucleotide is oriented as perfect or imperfect an inverse complement copy of at least part of the first polynucleotide.

3. The construct of claim 1, wherein neither the first nor the second polynucleotide is operably linked to (i) a nos gene terminator, (ii) the 3' untranslated sequence of T-DNA gene 7, (iii) the 3' untranslated sequences of the major inclusion body protein gene of cauliflower mosaic virus, (iv) the 3' untranslated sequences of the pea ribulose 1,5-bisphosphate carboxylase small subunit, (v) the 3' untranslated sequences of the potato ubiquitin-3 gene, (vi) the 3' untranslated sequences of the potato proteinase inhibitor II gene, (vii) the 3' untranslated sequences of opine genes, or (viii) the 3' untranslated sequences of endogenous genes.

4. The construct of claim 1, wherein the first polynucleotide comprises a sequence that shares sequence identity with a target gene or at least one of a regulatory element that is associated with the target gene, an exon of the target gene, an intron of the target gene, the 5'-untranslated region of the target gene, or the 3'-untranslated region of the target gene.

5. The construct of claim 4, wherein the target gene is a COMT gene involved in lignin biosynthesis, a CCOMT gene involved in lignin biosynthesis, any other gene involved in lignin biosynthesis, an R1 gene involved in starch phosphorylation, a phosphorylase gene involved in starch phosphorylation, a PPO gene involved in oxidation of polyphenols, a polygalacturonase gene involved in pectin degradation, a gene involved in the production of allergens, or a gene involved in fatty acid biosynthesis.

6. The construct of claim 1, wherein the first and second promoters are functional in a plant and wherein the expression cassette is located between transfer-DNA border sequences of a plasmid that is suitable for bacterium-mediated plant transformation, wherein the bacterium is a strain of Agrobacterium, Rhizobium, or Phyllobacterium.

7. The construct of claim 1, further comprising a spacer polynucleotide positioned between the first and second polynucleotides, wherein the spacer polynucleotide is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, 200, 300, 400, 500, or more than 500 nucleotides long.

8. The construct of claim 1, wherein the first promoter is a constitutive promoter, a tissue-specific promoter, or an inducible promoter and wherein the second promoter is a constitutive promoter, a near-constitutive promoter, a tissue-specific promoter, or an inducible promoter.

9. A transformation plasmid, comprising an expression cassette, which comprises in the 5' to 3' orientation (1) a first promoter that is operably linked to (2) a first desired polynucleotide, which abuts (3) at least one optional spacer polynucleotide, where the 3'-end of one of the spacer polynucleotides abuts a (4) a second desired polynucleotide, which is operably linked to (5) a second promoter, wherein neither desired polynucleotide in the expression cassette is operably linked to any known transcription terminator, and wherein the second desired polynucleotide and the first desired polynucleotide are fully identical in sequence over at least 23 nucleotides.

10. The transformation plasmid of claim 9, wherein (a) at least part of the first desired polynucleotide is in the antisense orientation and wherein at least part of the second desired polynucleotide is oriented as the perfect or imperfect inverse complement of the first desired polynucleotide; or (b) at least part of the first desired polynucleotide is in the sense orientation and wherein at least part of the second desired polynucleotide is oriented as the perfect or imperfect inverse complement of the first desired polynucleotide; or (c) at least part of the first desired polynucleotide of (a) or (b) is a promoter sequence or shares sequence identity with a promoter sequence.

11. The transformation plasmid of claim 10, wherein the sequence of (c) shares sequence identity with a promoter that is associated with an endogenous gene and selected from the group consisting of (1) a starch-associated R1 gene promoter, (2) a polyphenol oxidase gene promoter, (3) a fatty acid desaturase 12 gene promoter, (4) a microsomal omega-6 fatty acid desaturase gene promoter, (5) a cotton stearoyl-acyl-carrier protein delta 9-desaturase gene promoter, (6) an oleoyl-phosphatidylcholine omega 6-desaturase gene promoter, (7) a Medicago truncatula caffeic acid/5-hydroxyferulic acid 3/5-O-methyltransferase (COMT) gene promoter, (8) a Medicago sativa (alfalfa) caffeic acid/5-hydroxyferulic acid 3/5-O-methyltransferase (COMT) gene promoter, (9) a Medicago truncatula caffeoyl CoA 3-O-methyltransferase (CCOMT) gene promoter, (10) a Medicago sativa (alfalfa) caffeoyl CoA 3-O-methyltransferase (CCOMT) gene promoter, (11) a Zea mays (maize) COMT gene, (12) a major apple allergen Mal d 1 gene promoter, (13) a major peanut allergen Ara h 2 gene promoter, (14) a major soybean allergen Gly m Bd 30 K gene promoter, (15) a polygalacturonase gene promoter, (16) any other endogenous promoter.

12. The transformation plasmid of claim 10, wherein (1) (i) at least one of the first and second promoters is a GBSS promoter and (ii) the first desired polynucleotide is a sequence that shares sequence identity with at least a part of a promoter associated with a polyphenol oxidase gene; (2) both the first and second promoters are GBSS promoters; or (3) the first promoter is a GBSS promoter and the second promoter is an AGP promoter.

13. A method of reducing expression of a gene normally capable of being expressed in a plant cell, comprising exposing a plant cell to the construct of claim 1, wherein the construct is maintained in a bacterium strain, selected from the group consisting of *Agrobacterium tumefaciens, Rhizobium trifolii, Rhizobium leguminosarum, Phyllobacterium myrsinacearum, SinoRhizobium meliloti*, and *MesoRhizobium loti*, wherein the desired polynucleotide comprises a sequence that shares sequence identity to a target sequence in the plant cell genome.

14. A method for enhancing tolerance to black spot bruising in a tuber, comprising expressing the construct of claim 1 in a cell of a tuber, wherein (a) the first polynucleotide comprises the sequence that shares sequence identity with at least a part of a tuber-expressed polyphenol oxidase gene a tuber-expressed polyphenol oxidase gene promoter, (b) the second polynucleotide is the inverse complement of the first polynucleotide or an imperfect inverse complement of the first polynucleotide, (c) one or both of the first and second promoters are GBSS or AGP, and (d) expression of the construct in the cell reduces transcription and/or translation of a polyphenol oxidase gene in the tuber cell genome, thereby enhancing the tolerance of the tuber to black spot bruising.

15. The method of claim 14, wherein the first polynucleotide comprises the sequence of SEQ ID NO: 26 or 27.

16. The construct of claim 5, wherein the gene involved in fatty acid biosynthesis is FAD2.

* * * * *